(12) United States Patent
Papadopoulos et al.

(10) Patent No.: US 10,683,354 B2
(45) Date of Patent: *Jun. 16, 2020

(54) ANTIBODY-DRUG CONJUGATES COMPRISING ANTI-PROLACTIN RECEPTOR (PRLR) ANTIBODIES AND METHODS OF USE THEREOF TO KILL PRLR-EXPRESSING CELLS

(71) Applicant: Regeneron Pharmaceuticals, Inc., Tarrytown, NY (US)

(72) Inventors: Nicholas J. Papadopoulos, LaGrangeville, NY (US); Gavin Thurston, Briarcliff Manor, NY (US); Jessica R. Kirshner, New York, NY (US); Marcus P. Kelly, New York, NY (US); Thomas Nittoli, Pearl River, NY (US); Frank J. Delfino, Poughquag, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/134,838

(22) Filed: Sep. 18, 2018

(65) Prior Publication Data

US 2019/0241667 A1 Aug. 8, 2019

Related U.S. Application Data

(63) Continuation of application No. 15/601,884, filed on May 22, 2017, now Pat. No. 10,106,616, which is a continuation of application No. 15/051,580, filed on Feb. 23, 2016, now Pat. No. 9,688,764, which is a continuation of application No. 14/464,297, filed on Aug. 20, 2014, now Pat. No. 9,302,015.

(60) Provisional application No. 62/026,088, filed on Jul. 18, 2014, provisional application No. 62/012,440, filed on Jun. 16, 2014, provisional application No. 61/868,185, filed on Aug. 21, 2013.

(51) Int. Cl.
| | |
|---|---|
| *C07K 16/28* | (2006.01) |
| *A61K 47/68* | (2017.01) |
| *A61K 31/537* | (2006.01) |
| *A61K 39/00* | (2006.01) |

(52) U.S. Cl.
CPC ........ *C07K 16/2866* (2013.01); *A61K 31/537* (2013.01); *A61K 47/6803* (2017.08); *A61K 47/6849* (2017.08); *C07K 16/2869* (2013.01); *A61K 2039/505* (2013.01); *C07K 2317/21* (2013.01); *C07K 2317/24* (2013.01); *C07K 2317/52* (2013.01); *C07K 2317/56* (2013.01); *C07K 2317/565* (2013.01); *C07K 2317/73* (2013.01); *C07K 2317/76* (2013.01); *C07K 2317/77* (2013.01); *C07K 2317/92* (2013.01); *C07K 2317/94* (2013.01)

(58) Field of Classification Search
CPC ............ C07K 16/2866; C07K 16/2869; C07K 2317/21; C07K 2317/24; C07K 2317/52; C07K 2317/56; C07K 2317/565; C07K 2317/73; C07K 2317/76; C07K 2317/77; C07K 2317/92; C07K 2317/94; A61K 47/6803; A61K 47/6849; A61K 31/537; A61K 2039/505

See application file for complete search history.

(56) References Cited

U.S. PATENT DOCUMENTS

| | | |
|---|---|---|
| 5,208,020 A | 5/1993 | Chari et al. |
| 5,416,064 A | 5/1995 | Chari et al. |
| 6,429,186 B1 | 8/2002 | Fuh et al. |
| 6,441,163 B1 | 8/2002 | Chari et al. |

(Continued)

FOREIGN PATENT DOCUMENTS

| | | |
|---|---|---|
| CN | 102746402 A | 10/2012 |
| EP | 1079851 B1 | 7/2007 |

(Continued)

OTHER PUBLICATIONS

Damiano and Wasserman, "Molecular Pathways: Blockade of the PRLR Signaling Pathway as a Novel Antihormonal Approach for the Treatment of Breast and Prostate Cancer," Clin. Cancer Res., Apr. 1, 2013, 19(7):1644-1650.

(Continued)

*Primary Examiner* — Robert S Landsman
(74) *Attorney, Agent, or Firm* — Squire Patton Boggs (US) LLP

(57) ABSTRACT

The present invention provides antibodies that bind to prolactin receptor (PRLR) and methods of using the same. According to certain embodiments, the antibodies of the invention bind human PRLR with high affinity. In certain embodiments, the invention includes antibodies that bind PRLR and block prolactin-mediated cell signaling. In other embodiments, the invention includes antibodies that bind PRLR but do not block prolactin-mediated cell signaling. The antibodies of the invention may be fully human antibodies. The invention includes anti-PRLR antibodies conjugated to a cytotoxic agent, radionuclide, or other moiety detrimental to cell growth or proliferation. The antibodies of the invention are useful for the treatment of various cancers as well as other PRLR-related disorders. The present invention also includes antibody drug conjugates comprising an antibody or antigen-binding fragment thereof that specifically binds a class I cytokine receptor, wherein the antibody or antigen-binding fragment thereof is conjugated to a cytotoxic agent.

26 Claims, No Drawings

Specification includes a Sequence Listing.

(56) References Cited

U.S. PATENT DOCUMENTS

| | | |
|---|---|---|
| 6,867,187 B2 | 3/2005 | Clevenger et al. |
| 7,115,556 B2 | 10/2006 | Chen et al. |
| 7,422,899 B2 | 9/2008 | Elenbaas et al. |
| 7,867,493 B2 | 1/2011 | Damiano et al. |
| 8,198,417 B2 | 6/2012 | Steeves et al. |
| 2003/0022833 A1 | 1/2003 | Chen et al. |
| 2005/0271626 A1 | 12/2005 | Chen et al. |
| 2007/0060520 A1 | 3/2007 | Chen et al. |
| 2007/0092920 A1 | 4/2007 | Clevenger et al. |
| 2007/0269438 A1 | 11/2007 | Elenbaas et al. |
| 2008/0292620 A1 | 11/2008 | Damiano et al. |
| 2009/0017044 A1 | 1/2009 | Elenbaas et al. |
| 2011/0150760 A1 | 6/2011 | Damiano et al. |
| 2012/0315276 A1 | 12/2012 | Otto et al. |
| 2012/0321632 A1 | 12/2012 | Otto et al. |
| 2013/0022606 A1 | 1/2013 | Otto et al. |
| 2013/0129739 A1 | 5/2013 | Otto et al. |
| 2014/0065158 A1 | 3/2014 | Ma et al. |
| 2014/0141003 A1 | 5/2014 | Freiberg et al. |
| 2014/0227294 A1 | 8/2014 | Anderson et al. |
| 2014/0271659 A1 | 9/2014 | Ma et al. |
| 2015/0056222 A1 | 2/2015 | Papadopoulos et al. |
| 2018/0244789 A1 | 8/2018 | Reilly et al. |

FOREIGN PATENT DOCUMENTS

| | | |
|---|---|---|
| WO | WO-1999/058142 A1 | 11/1999 |
| WO | WO-2005/058232 A2 | 6/2005 |
| WO | WO-2008/022295 A1 | 2/2008 |
| WO | WO-2009/010398 A1 | 1/2009 |
| WO | WO-2009/134976 A1 | 11/2009 |
| WO | WO-2011/069794 A1 | 6/2011 |
| WO | WO-2011/069795 A1 | 6/2011 |
| WO | WO-2011/069796 A1 | 6/2011 |
| WO | WO-2011/069797 A1 | 6/2011 |
| WO | WO-2011/069798 A1 | 6/2011 |
| WO | WO-2011/069799 A1 | 6/2011 |
| WO | WO-2012/136519 A1 | 10/2012 |
| WO | WO-2012/163932 A1 | 12/2012 |
| WO | WO-2014/105810 A1 | 7/2014 |
| WO | WO-2014/143909 A1 | 9/2014 |
| WO | WO-2014/145090 A1 | 9/2014 |
| WO | WO 2015/026907 A1 | 2/2015 |

OTHER PUBLICATIONS

Damiano et al., "Neutralization of Prolactin Receptor Function by Monoclonal Antibody LFA102, a Novel Potential for the Treatment of Breast Cancer," Mol. Cancer Ther., Mar. 2013, 12(3):295-305.

Invitation to Respond to Written Opinion together with Written Opinion and Search report in Singapore application No. 11201601211T dated Mar. 2, 2017; 12 pages.

International Search Report and Written Opinion dated Nov. 26, 2014 of PCT/US2014/051831.

Okamura et al., (1989) "Characterization and Applications of Monoclonal Antibodies to the Prolactin Receptor," *Endocrinology*, 124(4):2499-2508.

Sissom et al., (1988) "Anti-Growth Action on Mouse Mammary and Prostate Glands of a Monoclonal Antibody to Prolactin Receptor," *American Journal of Pathology*, 133(3):589-595.

Otto et al., "A Neutralizing Prolactin Receptor Antibody Whose In Vivo Application Mimics the Phenotype of Female Prolactin Receptor-Deficient Mice", Endocrinology, vol. 156, No. 11, Nov. 1, 2015, pp. 4365-4373, XP055444583.

Lynn, "Fulvestrant ('Faslodex') a new hormonal treatment for advanced breast cancer", European Journal of Oncology Nursing, 2004, 8S, pp. S83-S88.

Jacobson et al., "Unexploited therapies in breast and prostate cancer: blockade of the prolactin receptor", Trends in Endocrinology and Metabolism, Nov. 2010, vol. 21, No. 11, pp. 691-698.

Kelly et al., "Preclinical Activity of the Novel Anti-Prolactin Receptor (PRLR) Antibody-Drug Conjugate REGN2878-DM1 in PRLR-Positive Breast Cancers", Molecular Cancer Therapeutics, vol. 16, No. 7, Apr. 4, 2017, pp. 1299-1311, XP055443941.

Mohamed et al., "Breast Cancer Theme Issue: Review: Targeted Therapy for Breast Cancer", The American Journal of Pathology, Oct. 2013, vol. 183, No. 4, pp. 1096-1112.

O'Sullivan et al., "Targeting Prolactin Receptor (PRLR) Signaling in PRLR-Positive Breast and Prostate Cancer", The Oncologist, 2016, vol. 21, pp. 523-526.

Singh et al., "HER2-positive advanced breast cancer: optimizing patient outcomes and opportunities for drug development", British Journal of Cancer, vol. 111, No. 10, Jul. 15, 2014, pp. 1888-1898, XP055251792.

Swaminathan et al., "Regulation of prolactin receptor levels and activity in breast cancer", J Mammary Gland Biol Neoplasia, Mar. 2008, vol. 13, No. 1, pp. 81-91.

ANTIBODY-DRUG CONJUGATES COMPRISING ANTI-PROLACTIN RECEPTOR (PRLR) ANTIBODIES AND METHODS OF USE THEREOF TO KILL PRLR-EXPRESSING CELLS

CROSS-REFERENCE TO RELATED APPLICATION

This application is a continuation of U.S. application Ser. No. 15/601,884, filed on May 22, 2017 now issued as U.S. Pat. No. 10,106,616 which is a continuation of U.S. application Ser. No. 15/051,580, filed on Feb. 23, 2016, now issued as U.S. Pat. No. 9,688,764, which is a continuation of U.S. application Ser. No. 14/464,297, filed on Aug. 20, 2014, now issued as U.S. Pat. No. 9,302,015, which in turn claims the benefit under 35 U.S.C. § 119(e) of U.S. Provisional application No. 61/868,185, filed on Aug. 21, 2013; 62/012,440, filed on Jun. 16, 2014; and 62/026,088, filed on Jul. 18, 2014, the disclosures of which are herein incorporated by reference in their entireties.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "114581.00222 Sequence listing.txt," created Sep. 18, 2018, and is 140 kilobytes in size. The sequence listing contained in this .txt file is part of the specification and is incorporated herein by reference in its entirety.

FIELD OF THE INVENTION

The present invention relates to antibodies, and antigen-binding fragments thereof, which specifically bind prolactin receptor (PRLR), as well as antibody-drug conjugates comprising such antibodies, and methods of use thereof.

BACKGROUND

Prolactin is a polypeptide growth hormone that exerts its activity by interacting with the prolactin receptor (PRLR). PRLR is a single transmembrane receptor belonging to the class 1 cytokine receptor superfamily. The binding of prolactin to PRLR leads to receptor dimerization and intracellular signaling. Signaling through PRLR is associated with various processes such as mammary gland development, lactation, reproduction and immunomodulation. Moreover, high levels of PRLR expression have been detected in breast, prostate and other tumor types.

Blockade of PRLR signaling has been suggested as a means for treating breast and prostate cancer. (See, e.g., Damiano and Wasserman, April 2013, Clin. Cancer Res. 19(7):1644-1650). Anti-PRLR antibodies are mentioned, e.g., in U.S. Pat. Nos. 7,867,493 and 7,422,899. Nonetheless, there is a need in the art for novel PRLR antagonists, such as anti-PRLR antibodies, for the treatment of cancer and other disorders associated with PRLR expression and/or signaling.

BRIEF SUMMARY OF THE INVENTION

The present invention provides antibodies and antigen-binding fragments thereof that bind human prolactin receptor (PRLR). The antibodies of the invention are useful, inter alia, for targeting tumor cells that express PRLR. The anti-PRLR antibodies of the invention, and antigen-binding portions thereof, may be used alone in unmodified form, or may be included as part of an antibody-drug conjugate or a bispecific antibody.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

Exemplary anti-PRLR antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-PRLR antibodies. Table 2 sets forth the nucleic acid sequence identifiers of the HCVRs, LCVRs, HCDR1, HCDR2 HCDR3, LCDR1, LCDR2 and LCDR3 of the exemplary anti-PRLR antibodies.

The present invention provides antibodies or antigen-binding fragments thereof that specifically bind PRLR, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind PRLR, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind PRLR, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-PRLR antibodies listed in Table 1. In certain embodiments, the HCVR/LCVR amino acid sequence pair is selected from the group consisting of: 18/26; 66/74; 274/282; 290/298; and 370/378.

The present invention also provides antibodies or antigen-binding fragments thereof that specifically bind PRLR, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind PRLR, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind PRLR, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind PRLR, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind PRLR, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind PRLR, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind PRLR, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-PRLR antibodies listed in Table 1. In certain embodiments, the HCDR3/LCDR3 amino acid sequence pair is selected from the group consisting of: 24/32; 72/80; 280/288; 296/304; and 376/384.

The present invention also provides antibodies or antigen-binding fragments thereof that specifically bind PRLR, comprising a set of six CDRs HCDR1-HCDR2-HCDR3-LCDR1-LCDR2-LCDR3) contained within any of the exemplary anti-PRLR antibodies listed in Table 1. In certain embodiments, the HCDR1-HCDR2-HCDR3-LCDR1-LCDR2-LCDR3 amino acid sequences set is selected from the group consisting of: 20-22-24-28-30-32; 68-70-72-76-78-80; 276-278-280-284-286-288; 292-294-296-300-302-304; and 372-374-376-380-382-384.

In a related embodiment, the present invention provides antibodies, or antigen-binding fragments thereof that specifically bind PRLR, comprising a set of six CDRs (i.e., HCDR1-HCDR2-HCDR3-LCDR1-LCDR2-LCDR3) contained within an HCVR/LCVR amino acid sequence pair as defined by any of the exemplary anti-PRLR antibodies listed in Table 1. For example, the present invention includes antibodies or antigen-binding fragments thereof that specifically bind PRLR, comprising the HCDR1-HCDR2-HCDR3-LCDR1-LCDR2-LCDR3 amino acid sequences set contained within an HCVR/LCVR amino acid sequence pair selected from the group consisting of: 18/26; 66/74; 274/282; 290/298; and 370/378. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-PRLR antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-PRLR antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-PRLR antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-PRLR antibody listed in Table 1.

The present invention also provides recombinant expression vectors capable of expressing a polypeptide comprising a heavy or light chain variable region of an anti-PRLR antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-PRLR antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds PRLR and a pharmaceutically acceptable carrier. In a related aspect, the invention features a composition which is a combination of an anti-PRLR antibody and a second therapeutic agent. In one embodiment, the second therapeutic agent is any agent that is advantageously combined with an anti-PRLR antibody. The present invention also provides antibody-drug conjugates (ADCs) comprising an anti-PRLR antibody conjugated to a cytotoxic agent. Exemplary combination therapies, co-formulations, and ADCs involving the anti-PRLR antibodies of the present invention are disclosed elsewhere herein.

In yet another aspect, the invention provides therapeutic methods for killing tumor cells or for inhibiting or attenuating tumor cell growth using an anti-PRLR antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by targeting PRLR and/or by inhibiting prolactin-mediated cell signaling through PRLR.

Other embodiments will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression prolactin receptor, "PRLR," and the like, as used herein, refers to the human prolactin receptor, comprising the amino acid sequence as set forth in SEQ ID NO:404. The expression "PRLR" includes both monomeric and multimeric PRLR molecules. As used herein, the expression "monomeric human PRLR" means a PRLR protein or portion thereof that does not contain or possess any multimerizing domains and that exists under normal conditions as a single PRLR molecule without a direct physical connection to another PRLR molecule. An exemplary monomeric PRLR molecule is the molecule referred to herein as "hPRLR.mmh" comprising the amino acid sequence of SEQ ID NO:401 (see, e.g., Example 3, herein). As used herein, the expression "dimeric human PRLR" means a construct comprising two PRLR molecules connected to one another through a linker, covalent bond, non-covalent bond, or through a multimerizing domain such as an antibody Fc domain. An exemplary dimeric PRLR molecule is the molecule referred to herein as "hPRLR.mFc" comprising the amino acid sequence of SEQ ID NO:402 (see, e.g., Example 3, herein).

All references to proteins, polypeptides and protein fragments herein are intended to refer to the human version of the respective protein, polypeptide or protein fragment unless explicitly specified as being from a non-human species. Thus, the expression "PRLR" means human PRLR unless specified as being from a non-human species, e.g., "mouse PRLR," "monkey PRLR," etc.

As used herein, the expression "cell surface-expressed PRLR" means one or more PRLR protein(s), or the extracellular domain thereof, that is/are expressed on the surface of a cell in vitro or in vivo, such that at least a portion of a PRLR protein is exposed to the extracellular side of the cell membrane and is accessible to an antigen-binding portion of an antibody. A "cell surface-expressed PRLR" can comprise or consist of a PRLR protein expressed on the surface of a cell which normally expresses PRLR protein. Alternatively, "cell surface-expressed PRLR" can comprise or consist of PRLR protein expressed on the surface of a cell that normally does not express human PRLR on its surface but has been artificially engineered to express PRLR on its surface.

As used herein, the expression "anti-PRLR antibody" includes both monovalent antibodies with a single specificity, as well as bispecific antibodies comprising a first arm that binds PRLR and a second arm that binds a second (target) antigen, wherein the anti-PRLR arm comprises any of the HCVR/LCVR or CDR sequences as set forth in Table 1 herein. The expression "anti-PRLR antibody" also includes antibody-drug conjugates (ADCs) comprising an anti-PRLR antibody or antigen-binding portion thereof conjugated to a drug or toxin (i.e., cytotoxic agent). The expression "anti-PRLR antibody" also includes antibody-radionuclide conjugates (ARCs) comprising an anti-PRLR antibody or antigen-binding portion thereof conjugated to a radionuclide.

The term "antibody", as used herein, means any antigen-binding molecule or molecular complex comprising at least one complementarity determining region (CDR) that specifically binds to or interacts with a particular antigen (e.g., PRLR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PRLR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-PRLR antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-PRLR antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-PRLR antibodies comprising variants of any of the HCVR, LCVR, and/or CDR amino acid sequences disclosed herein having one or more conservative substitutions. For example, the present invention includes anti-PRLR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 pH-Dependent Binding

The present invention includes anti-PRLR antibodies with pH-dependent binding characteristics. For example, an anti-PRLR antibody of the present invention may exhibit reduced binding to PRLR at acidic pH as compared to neutral pH. Alternatively, anti-PRLR antibodies of the invention may exhibit enhanced binding to PRLR at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PRLR at acidic pH as compared to neutral pH" is expressed in terms of a ratio of the $K_D$ value of the antibody binding to PRLR at acidic pH to the $K_D$ value of the antibody binding to PRLR at neutral pH (or vice versa). For example, an antibody or antigen-binding fragment thereof may be regarded as exhibiting "reduced binding to PRLR at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Anti-PRLR Antibodies Comprising Fc Variants

According to certain embodiments of the present invention, anti-PRLR antibodies are provided comprising an Fc domain comprising one or more mutations which enhance or diminish antibody binding to the FcRn receptor, e.g., at acidic pH as compared to neutral pH. For example, the present invention includes anti-PRLR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-PRLR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies

The present invention includes antibodies and antigen-binding fragments thereof that bind monomeric human PRLR with high affinity. For example, the present invention includes anti-PRLR antibodies that bind monomeric human PRLR (e.g., hPRLR.mmh) with a $K_D$ of less than about 4.0 nM as measured by surface plasmon resonance at 25° C. or 37° C., e.g., using an assay format as defined in Example 3 herein, or a substantially similar assay. According to certain embodiments, anti-PRLR antibodies are provided that bind monomeric human PRLR at 37° C. with a $K_D$ of less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, or less than about 300 pM, as measured by surface plasmon resonance, e.g., using an assay format as defined in Example 3 herein, or a substantially similar assay.

The present invention also includes antibodies and antigen-binding fragments thereof that bind monomeric human PRLR (e.g., hPRLR.mmh) with a dissociative half-life (t ½) of greater than about 5 minutes as measured by surface plasmon resonance at 25° C. or 37° C., e.g., using an assay format as defined in Example 3 herein, or a substantially similar assay. According to certain embodiments, anti-PRLR antibodies are provided that bind monomeric human PRLR at 37° C. with a t½ of greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, or longer, as measured by surface plasmon resonance, e.g., using an assay format as defined in Example 3 herein, or a substantially similar assay.

The present invention also includes antibodies and antigen-binding fragments thereof that bind dimeric human PRLR (e.g., hPRLR.mFc) with high affinity. For example, the present invention includes anti-PRLR antibodies that bind dimeric human PRLR with a $K_D$ of less than about 250 pM as measured by surface plasmon resonance at 25° C. or 37° C., e.g., using an assay format as defined in Example 3 herein, or a substantially similar assay. According to certain embodiments, anti-PRLR antibodies are provided that bind dimeric human PRLR at 37° C. with a $K_D$ of less than about 250 pM, less than about 200 pM, less than about 180 pM, less than about 160 pM, less than about 140 pM, less than about 120 pM, less than about 100 pM, less than about 80 pM, less than about 70 pM, or less than about 60 pM, as measured by surface plasmon resonance, e.g., using an assay format as defined in Example 3 herein, or a substantially similar assay.

The present invention also includes antibodies and antigen-binding fragments thereof that bind dimeric human PRLR (e.g., hPRLR.mFc) with a dissociative half-life (t ½) of greater than about 55 minutes as measured by surface plasmon resonance at 25° C. or 37° C., e.g., using an assay format as defined in Example 3 herein, or a substantially similar assay. According to certain embodiments, anti-PRLR antibodies are provided that bind dimeric human PRLR at 37° C. with a t ½ of greater than about 55 minutes, greater than about 60 minutes, greater than about 65 minutes, greater than about 70 minutes, greater than about 75 minutes, greater than about 80 minutes, greater than about 85 minutes, greater than about 90 minutes, greater than about 95 minutes, greater than about 100 minutes, greater than about 120 minutes, greater than about 140 minutes, greater than about 160 minutes, or longer, as measured by surface plasmon resonance, e.g., using an assay format as defined in Example 3 herein, or a substantially similar assay.

The present invention also includes antibodies and antigen-binding fragments thereof that bind PRLR and block prolactin-mediated signaling in cells expressing human PRLR. For example, the present invention includes anti-PRLR antibodies that block prolactin-mediated signaling in cells that express human PRLR, with an $IC_{50}$ of less than about 1.3 nM as measured using a prolactin signaling blocking assay, e.g., using an assay format as defined in Example 5 herein, or a substantially similar assay. According to certain embodiments, anti-PRLR antibodies are provided that block prolactin-mediated signaling in cells expressing human PRLR, with an $IC_{50}$ of less than about 1.3 nM, less than about 1.2 nM, less than about 1.0 nM, less than about 900 pM, less than about 800 pM, less than about 600 pM, less than about 400 pM, less than about 200 pM, less than about 100 pM, less than about 80 pM, less than about 60 pM, less than about 40 pM, less than about 20 pM as measured using a prolactin signaling blocking assay, e.g., using an assay format as defined in Example 5 herein, or a substantially similar assay.

The present invention also includes antibodies and antigen-binding fragments thereof that bind PRLR but do not block prolactin-mediated signaling in cells expressing human PRLR. As used herein, an antibody or antigen-binding fragment thereof "does not block" prolactin-mediated signaling if, when tested in a prolactin signaling blocking assay such as the assay defined in Example 5 herein or a substantially similar assay, the antibody exhibits no or only negligible blocking activity. According to certain embodiments, an antibody or antigen-binding fragment "does not block" prolactin-mediated signaling if the antibody exhibits an $IC_{50}$ value of greater than about 10 nM, or greater than about 100 nM when tested in a prolactin signaling blocking assay such as the assay defined in Example 5 herein or a substantially similar assay.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Antibody-Drug Conjugates (ADCs)

The present invention provides antibody-drug conjugates (ADCs) comprising an anti-PRLR antibody or antigen-binding fragment thereof conjugated to a therapeutic moiety such as a cytotoxic agent, a chemotherapeutic drug, or a radioisotope.

Cytotoxic agents include any agent that is detrimental to the growth, viability or propagation of cells. Examples of suitable cytotoxic agents and chemotherapeutic agents that can be conjugated to anti-PRLR antibodies in accordance with this aspect of the invention include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins, camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing. According to certain embodiments, the cytotoxic agent that is conjugated to an anti-PRLR antibody is a maytansinoid such as DM1 or DM4, a tomaymycin derivative, or a dolastatin derivative. According to certain embodiments, the cytotoxic agent that is conjugated to an anti-PRLR antibody is an auristatin such as MMAE, MMAF, or derivatives thereof. Other cytotoxic agents known in the art are contemplated within the scope of the present invention, including, e.g., protein toxins such ricin, *C. difficile* toxin, *pseudomonas* exotoxin, ricin, diphtheria toxin, botulinum toxin, bryodin, saporin, pokeweed toxins (i.e., phytolaccatoxin and phytolaccigenin), and others such as those set forth in Sapra et al., Pharmacol. & Therapeutics, 2013, 138:452-469.

The present invention also includes antibody-radionuclide conjugates (ARCs) comprising anti-PRLR antibodies conjugated to one or more radionuclides. Exemplary radionuclides that can be used in the context of this aspect of the invention include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In certain embodiments of the present invention, ADCs are provided comprising an anti-PRLR conjugated to a cytotoxic agent (e.g., any of the cytotoxic agents disclosed above) via a linker molecule. Any linker molecule or linker technology known in the art can be used to create or construct an ADC of the present invention. In certain embodiments, the linker is a cleavable linker. According to other embodiments, the linker is a non-cleavable linker. Exemplary linkers that can be used in the context of the present invention include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present invention are disclosed, e.g., in U.S. Pat. No. 7,754,681 and in Ducry, Bioconjugate Chem., 2010, 21:5-13, and the references cited therein, the contents of which are incorporated by reference herein in their entireties.

The present invention comprises ADCs in which a linker connects an anti-PRLR antibody or antigen-binding molecule to a drug or cytotoxin through an attachment at a particular amino acid within the antibody or antigen-binding molecule. Exemplary amino acid attachments that can be used in the context of this aspect of the invention include, e.g., lysine (see, e.g., U.S. Pat. No. 5,208,020; US 2010/0129314; Hollander et al., Bioconjugate Chem., 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., Proc. Natl. Acad. Sci., USA, 2008, 105:12451-12456), formyl glycine (see, e.g., Carrico et al., Nat. Chem. Biol., 2007, 3:321-322; Agarwal et al., Proc. Natl. Acad. Sci., USA, 2013, 110:46-51, and Rabuka et al., Nat. Protocols, 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., Food & Agriculture Immunol., 2001, 13:127-130) and disulfide linkers (see, e.g., WO 2013/085925, WO 2010/010324, WO 2011/018611, and Shaunak et al., Nat. Chem. Biol., 2006, 2:312-313).

According to certain embodiments, the present invention provides ADCs, wherein an anti-PRLR antibody as described herein is conjugated to a linker-drug composition as set forth in International Patent Application No. PCT/US14/29757, filed on Mar. 14, 2014 (e.g., compound "7," also referred to herein as "M0026"), the disclosure of which is hereby incorporated by reference herein in its entirety.

Any method known in the art for conjugating a chemical moiety to a peptide, polypeptide or other macromolecule can be used in the context of the present invention to make an anti-PRLR ADC as described herein. An exemplary method for antibody-drug conjugation via a linker is set forth in Example 6 herein. Variations on this exemplary method will be appreciated by persons of ordinary skill in the art and are contemplated within the scope of the present invention.

Targeting ADCs to Cells Expressing Low Levels of PRLR

It was surprisingly discovered by the present inventors that ADCs comprising an anti-PRLR antibody conjugated to a cytotoxic agent are able to specifically target and kill cells that express relatively low levels of cell surface PRLR. For example, in Example 7 herein, it is shown that an ADC comprising anti-PRLR antibody H1H6953N conjugated to DM1 was able to inhibit the growth of T47D cells (expressing PRLR at only 12× above background) with an $IC_{50}$ of 1.3 nM and showed 78% killing. By contrast, ADCs against other tumor-associated antigens such as ErbB2 typically require much higher expression levels of the target antigen on cells for comparable killing potencies. For example, cell killing in the sub-nanomolar $IC_{50}$ range was obtained with an anti-ErbB2-DM1 ADC only with cells that express ErbB2 at levels of greater than about 200× to about 400× above background (see, e.g., Tables 14-17 herein). The ability to kill tumor cells that express relatively low levels of tumor-associated antigen such as PRLR means that the anti-PRLR ADCs of the present invention can provide significant therapeutic benefits with a lower dose and/or less frequent dosing than is required for ADCs that target other tumor antigens such as ErbB2.

Accordingly, the present invention provides antibody-drug conjugates (ADCs) comprising an antibody or antigen-binding fragment thereof that specifically binds human PRLR conjugated to a cytotoxic agent, wherein the ADCs effectively kill cells (e.g., tumor cells) that express low levels of PRLR. In related embodiments, the present invention includes methods for effectively killing cells that express low levels of PRLR. The methods according to this aspect of the invention comprise contacting the cells with an antibody-drug conjugate (ADC) comprising an anti-PRLR antibody conjugated to a cytotoxic agent. "Contacting the cells" can be carried out in vitro, or in vivo, e.g., by administering an anti-PRLR ADC to a subject in need thereof, wherein the administration causes the ADC to come into contact with cells expressing PRLR.

According to certain contexts envisioned within the scope of the present invention, a "low level of PRLR" means an expression level of less than about 30-fold above background. According to certain embodiments, anti-PRLR ADCs are provided which effectively kill cells that express PRLR at an expression level of less than about 30-fold, 25-fold, 20-fold, 18-fold, 16-fold, 14-fold, 12-fold, 10-fold, 8-fold, or less, above background. As used herein, the term "background" means the (non-specific) signal produced when cells are treated with an isotype control antibody (i.e., not specific for PRLR).

In certain other contexts, a "low level of PRLR" can be expressed in terms of the number of PRLR molecules per cell. For example, as used herein, a cell that expresses a "low level" of PRLR expresses less than about 1 million copies of PRLR per cell. In specific embodiments, a "low level" of PRLR means less than about 900,000 copies, less than about 800,000 copies, less than about 700,000 copies, less than about 600,000 copies, less than about 500,000 copies, less than about 400,000 copies, less than about 300,000 copies, less than about 200,000 copies, less than about 100,000 copies, less than about 90,000 copies, less than about 80,000 copies, less than about 70,000 copies, less than about 60,000 copies, less than about 50,000 copies, less than about 40,000 copies, less than about 30,000 copies, less than about 20,000 copies, or less than about 10,000 copies of PRLR per cell.

As used herein, "effective killing" means that the ADC exhibits an $IC_{50}$ of less than about 20 nM, or less than about 1 nM (e.g., less than about 0.9 nM, less than about 0.8 nM, less than about 0.7 nM, less than about 0.6 nM, less than about 0.5 nM, less than about 0.4 nM, or less than about 0.3 nM) in a tumor cell killing assay, such as the assay defined in Example 7 herein, or a substantially similar assay. According to this aspect of the invention, the anti-PRLR antibody component of the ADC can be any anti-PRLR antibody including anti-PRLR antibodies comprising any of the CDR or HCVR/LCVR amino acid sequences as set forth in Table 1 herein. Additionally, the cytotoxic agent component of the ADC can be any cytotoxic agent, such as DM1, or any other cytotoxic agent mentioned herein.

ADCs of the present invention are able to inhibit tumor growth and/or reduce tumor size in PRLR+ tumor-bearing animals. For example, as shown in Example 8 herein, anti-PRLR-DM1 ADCs were shown to reduce tumors to undetectable levels in mice bearing PRLR+ breast cancer xenografts. Thus, the present invention includes anti-PRLR antibodies and ADCs comprising such antibodies, wherein the antibodies or ADCs, when administered to a PRLR+ tumor-bearing animal (e.g., at a frequency of about once a week, and a dose of about 1 to 15 mg/kg), inhibit tumor growth and/or reduce tumor size (e.g., tumor growth inhibition of 100% or greater) by Day 52 post-administration or sooner.

Class I Cytokine Receptor Targeting

PRLR belongs to the class I cytokine receptor family. As explained above and demonstrated in the working examples herein, it was unexpectedly discovered that antibody-drug conjugates (ADCs) comprising anti-PRLR antibodies can effectively target and kill cells that express low levels of PRLR (see Example 7 herein). Furthermore, it was shown that ADCs against other class I cytokine receptors (IL-4R and IL-6R) also are able to potently kill cell lines expressing relatively low levels of target antigen (see Example 9 herein). This property is in contrast to ADCs against other cell surface-expressed proteins, such as ErbB2, wherein effective cell killing requires high target expression. Moreover, it was also surprisingly discovered that anti-PRLR antibodies are internalized substantially faster than anti-Her2 antibodies on tumor cells (e.g., T47D tumor cells), and that this property is correlated with faster internalization and degradation of cell surface PRLR compared to cell surface Her2.

In view of the results set forth herein, the present inventors conceived that the ability to target and kill cells that express low levels of cell surface antigen may be a common property shared by ADCs directed against class I cytokine receptors in general, and in particular class I cytokine receptors that are rapidly internalized. Thus, the present invention includes methods for targeting class I cytokine receptors (e.g., rapidly internalizing class I cytokine receptors), and methods for killing cells that express class I cytokine receptors such as cells that express low levels of class I cytokine receptors.

The methods according to this aspect of the invention comprise contacting a cell that expresses a class I cytokine receptor with an ADC comprising an antibody or antigen-binding fragment thereof that specifically binds the class I cytokine receptor. According to certain embodiments, the cell to be targeted expresses low levels (as that expression is defined elsewhere herein) of a class I cytokine receptor and/or a class I cytokine receptor that is rapidly internalized and degraded (e.g., internalized faster than a reference cell surface molecule such as Her2). Also included within the present invention are ADCs comprising an antibody or antigen-binding fragment thereof that specifically binds a class I cytokine receptor, conjugated to a cytotoxic agent. Any of the cytotoxic agents, linkers, and/or ADC-related technologies described elsewhere herein can be used in the context of this aspect of the invention.

As used herein a "class I cytokine receptor" (also sometimes referred to as a "type I cytokine receptor") means a transmembrane receptor expressed on the surface of cells that recognizes and responds to cytokines with four alpha-helical strands. As explained below, class I cytokine receptors can be heterodimeric or homodimeric. As used herein, the term "class I cytokine receptor" includes both heterodimeric and homodimeric receptors.

Heterodimeric class I cytokine receptors consist of a cytokine-specific chain and a "common chain." Accordingly, such heterodimeric class I cytokine receptors can be classified based on the type of common chain used by the receptor for signaling. Exemplary categories of heterodimeric class I cytokine receptors include: (i) common gamma chain-containing heterodimeric receptors such as IL-2R, IL-4R, IL-7R, IL-9R, IL-13R and IL-15R; (ii) common beta chain-containing heterodimeric receptors such as GM-CSF receptor, IL-3R and IL-5R; and (iii) gp130-containing heterodimeric receptors such as IL-6R, IL-11R, CNTF receptor, leukemia inhibitory factor (LIF) receptor, oncostatin M (OSM) receptor, and IL-12 receptor.

Homodimeric class I cytokine receptors include growth hormone (GH) receptor, erythropoietin (EPO) receptor, G-CSF receptor, leptin receptor, and PRLR.

In certain embodiments of this aspect of the invention, the ADC comprises an antibody or antigen-binding fragment thereof that specifically binds a heterodimeric class I cytokine receptor. According to other embodiments of this aspect of the invention, the ADC comprises an antibody or antigen-binding fragment thereof that specifically binds a homodimeric class I cytokine receptor.

The present invention includes methods for killing a cell that expresses low levels of a heterodimeric class I cytokine receptor. The methods according to this aspect of the invention comprise contacting a cell that expresses a low level of a heterodimeric class I cytokine receptor with an ADC comprising an antibody or antigen-binding fragment thereof that specifically binds the heterodimeric class I cytokine receptor.

Alternatively, the present invention includes methods for killing a cell that expresses low levels of a homodimeric class I cytokine receptor. The methods according to this aspect of the invention comprise contacting a cell that expresses a low level of a homodimeric class I cytokine receptor with an ADC comprising an antibody or antigen-binding fragment thereof that specifically binds the homodimeric class I cytokine receptor.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a PRLR protein. Alternatively, the epitope may consist of a plurality of non-contiguous amino acids (or amino acid sequences) of PRLR. In some embodiments, the epitope is located on or near the prolactin-binding domain of PRLR. In other embodiments, the epitope is located outside of the prolactin-binding domain of PRLR, e.g., at a location on the surface of PRLR at which an antibody, when bound to such an epitope, does not interfere with prolactin binding to PRLR.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-PRLR antibodies that bind to the same epitope as any of the specific exemplary antibodies described herein (e.g. antibodies comprising any of the amino acid sequences as set forth in Table 1 herein). Likewise, the present invention also includes anti-PRLR antibodies that compete for binding to PRLR with any of the specific exemplary antibodies described herein (e.g. antibodies comprising any of the amino acid sequences as set forth in Table 1 herein).

One can easily determine whether an antibody binds to the same epitope as, or competes for binding with, a reference anti-PRLR antibody by using routine methods known in the art and exemplified herein. For example, to determine if a test antibody binds to the same epitope as a reference anti-PRLR antibody of the invention, the reference antibody is allowed to bind to a PRLR protein. Next, the ability of a test antibody to bind to the PRLR molecule is assessed. If the test antibody is able to bind to PRLR following saturation binding with the reference anti-PRLR antibody, it can be concluded that the test antibody binds to a different epitope than the reference anti-PRLR antibody. On the other hand, if the test antibody is not able to bind to the PRLR molecule following saturation binding with the reference anti-PRLR antibody, then the test antibody may bind to the same epitope as the epitope bound by the reference anti-PRLR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-PRLR antibody, the above-described binding methodology is performed in two orientations: In a first orientation, the reference antibody is allowed to bind to a PRLR protein under saturating conditions followed by assessment of binding of the test antibody to the PRLR molecule. In a second orientation, the test antibody is allowed to bind to a PRLR molecule under saturating conditions followed by assessment of binding of the reference antibody to the PRLR molecule. If, in both orientations, only the first (saturating) antibody is capable of binding to the PRLR molecule, then it is concluded that the test antibody and the reference antibody compete for binding to PRLR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-PRLR antibodies of the present invention can be fully human antibodies. Methods for generating monoclonal antibodies, including fully human monoclonal antibodies are known in the art. Any such known methods can be used in the context of the present invention to make human antibodies that specifically bind to human PRLR.

Using VELOCIMMUNE™ technology, for example, or any other similar known method for generating fully human monoclonal antibodies, high affinity chimeric antibodies to PRLR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-PRLR antibody. While the constant region selected may vary according to specific use, high affinity antigen-binding and target specificity characteristics reside in the variable region. In certain instances, fully human anti-PRLR antibodies are isolated directly from antigen-positive B cells.

Bioequivalents

The anti-PRLR antibodies and antibody fragments of the present invention encompass proteins having amino acid sequences that vary from those of the described antibodies but that retain the ability to bind human PRLR. Such variant antibodies and antibody fragments comprise one or more additions, deletions, or substitutions of amino acids when compared to parent sequence, but exhibit biological activity that is essentially equivalent to that of the described antibodies. Likewise, the anti-PRLR antibody-encoding DNA sequences of the present invention encompass sequences that comprise one or more additions, deletions, or substitutions of nucleotides when compared to the disclosed sequence, but that encode an anti-PRLR antibody or antibody fragment that is essentially bioequivalent to an anti-PRLR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PRLR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-PRLR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-PRLR antibodies that bind to human PRLR but not to PRLR from other species. The present invention also includes anti-PRLR antibodies that bind to human PRLR and to PRLR from one or more non-human species. For example, the anti-PRLR antibodies of the invention may bind to human PRLR and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee PRLR. According to certain exemplary embodiments of the present invention, anti-PRLR antibodies are provided which specifically bind human PRLR and cynomolgus monkey (e.g., *Macaca fascicularis*) PRLR. Other anti-PRLR antibodies of the invention bind human PRLR but do not bind, or bind only weakly, to cynomolgus monkey PRLR.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-PRLR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human PRLR, and the other arm of the immunoglobulin is specific for a second antigen. The PRLR-binding arm can comprise any of the HCVR/LCVR or CDR amino acid sequences as set forth in Table 1 herein. In certain embodiments, the PRLR-binding arm binds human PRLR and blocks prolactin binding to PRLR. In other embodiments, the PRLR-binding arm binds human PRLR but does not block prolactin binding to PRLR.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-PRLR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-PRLR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-PRLR antibody or an antibody-drug conjugate comprising an anti-PRLR antibody (e.g., an anti-PRLR antibody or ADC comprising any of the HCVR/LCVR or CDR sequences as set forth in Table 1 herein). The therapeutic composition can comprise any of the anti-PRLR antibodies, antigen-binding fragments thereof, or ADCs disclosed herein, and a pharmaceutically acceptable carrier or diluent.

The antibodies and ADCs of the invention are useful, inter alia, for the treatment, prevention and/or amelioration of any disease or disorder associated with or mediated by PRLR expression or activity, or treatable by blocking the interaction between PRLR and prolactin or otherwise inhibiting PRLR activity and/or signaling, and/or promoting receptor internalization and/or decreasing cell surface receptor number. For example, the antibodies and ADCs of the present invention are useful for the treatment of tumors that express PRLR and/or that respond to prolactin-mediated signaling, e.g., breast tumors. The antibodies and antigen-binding fragments of the present invention may also be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and ADCs of the invention are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, or melanoma.

The anti-PRLR antibodies of the present invention are also useful for the treatment or prevention of one or more diseases or disorders selected from the group consisting of endometriosis, adenomyosis, non-hormonal female fertility contraception, benign breast disease and mastalgia, lactation inhibition, benign prostate hyperplasia, fibroids, hyper- and normoprolactinemic hair loss, and as part of hormone therapy to inhibit mammary epithelial cell proliferation.

In the context of the methods of treatment described herein, the anti-PRLR antibody may be administered as a monotherapy (i.e., as the only therapeutic agent) or in combination with one or more additional therapeutic agents (examples of which are described elsewhere herein).

The present invention includes methods for identifying patients who are treatable with an antibody or ADC of the present invention by assaying for high levels of PRLR expression in one or more tissues of the patient such as a tumor tissue. In a related embodiment, the present invention includes methods for treating cancers characterized by high level expression of PRLR. For example, the present invention includes methods of treatment comprising administering an anti-PRLR antibody of the invention, or ADC thereof (e.g., any of the anti-PRLR ADCs described elsewhere herein), to a subject with a tumor, wherein the tumor has been identified as expressing high levels of PRLR. In certain embodiments, the tumor is identified as expressing high levels of PRLR by immunohistochemistry of a biopsy sample or other imaging techniques such as, e.g., immuno-PET imaging, etc.

Combination Therapies and Formulations

The present invention includes compositions and therapeutic formulations comprising any of the anti-PRLR antibodies described herein in combination with one or more additional therapeutically active components, and methods of treatment comprising administering such combinations to subjects in need thereof.

The anti-PRLR antibodies of the present invention may be co-formulated with and/or administered in combination with one or more additional therapeutically active component(s) selected from the group consisting of: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), etc. Other agents that may be beneficially administered in combination with antibodies of the invention include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention includes compositions and therapeutic formulations comprising any of the anti-PRLR antibodies described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The anti-PRLR antibodies of the invention may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-PRLR antibody of the present invention; (for purposes of the present disclosure, such administration regimens are considered the administration of an anti-PRLR antibody "in combination with" an additional therapeutically active component). The present invention includes pharmaceutical compositions in which an anti-PRLR antibody of the present invention is co-formulated with one or more of the additional therapeutically active component(s) as described elsewhere herein.

Administration Regimens

According to certain embodiments of the present invention, multiple doses of an anti-PRLR antibody (or a pharmaceutical composition comprising a combination of an anti-PRLR antibody and any of the additional therapeutically active agents mentioned herein) may be administered to a subject over a defined time course. The methods according to this aspect of the invention comprise sequentially administering to a subject multiple doses of an anti-PRLR antibody of the invention. As used herein, "sequentially administering" means that each dose of anti-PRLR antibody is administered to the subject at a different point in time, e.g., on different days separated by a predetermined interval (e.g., hours, days, weeks or months). The present invention includes methods which comprise sequentially administering to the patient a single initial dose of an anti-PRLR antibody, followed by one or more secondary doses of the anti-PRLR antibody, and optionally followed by one or more tertiary doses of the anti-PRLR antibody.

The terms "initial dose," "secondary doses," and "tertiary doses," refer to the temporal sequence of administration of the anti-PRLR antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PRLR antibody, but generally may differ from one another in terms of frequency of administration. In certain embodiments, however, the amount of anti-PRLR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-PRLR antibody which is administered to a patient prior to the administration of the very next dose in the sequence with no intervening doses.

The methods according to this aspect of the invention may comprise administering to a patient any number of secondary and/or tertiary doses of an anti-PRLR antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.

Diagnostic Uses of the Antibodies

The anti-PRLR antibodies of the present invention may also be used to detect and/or measure PRLR, or PRLR-expressing cells in a sample, e.g., for diagnostic purposes. For example, an anti-PRLR antibody, or fragment thereof, may be used to diagnose a condition or disease characterized by aberrant expression (e.g., over-expression, under-expression, lack of expression, etc.) of PRLR. Exemplary diagnostic assays for PRLR may comprise, e.g., contacting a sample, obtained from a patient, with an anti-PRLR antibody of the invention, wherein the anti-PRLR antibody is labeled with a detectable label or reporter molecule. Alternatively, an unlabeled anti-PRLR antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure PRLR in a sample include enzyme-linked immunosorbent assay (ELISA), radioimmunoassay (RIA), immuno-PET (e.g., $^{89}$Zr, $^{64}$Cu, etc.), and fluorescence-activated cell sorting (FACS).

Samples that can be used in PRLR diagnostic assays according to the present invention include any tissue or fluid sample obtainable from a patient which contains detectable quantities of PRLR protein, or fragments thereof, under normal or pathological conditions. Generally, levels of PRLR in a particular sample obtained from a healthy patient (e.g., a patient not afflicted with a disease or condition associated with abnormal PRLR levels or activity) will be measured to initially establish a baseline, or standard, level of PRLR. This baseline level of PRLR can then be compared against the levels of PRLR measured in samples obtained from individuals suspected of having a PRLR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-PRLR Antibodies

Anti-PRLR antibodies were obtained by immunizing a VELOCIMMUNE® mouse (i.e., an engineered mouse comprising DNA encoding human immunoglobulin heavy and kappa light chain variable regions) with an immunogen comprising a soluble dimeric ecto domain of human PRLR. The antibody immune response was monitored by a PRLR-specific immunoassay. When a desired immune response was achieved splenocytes were harvested and fused with mouse myeloma cells to preserve their viability and form hybridoma cell lines. The hybridoma cell lines were screened and selected to identify cell lines that produce PRLR-specific antibodies. Using this technique several anti-PRLR chimeric antibodies (i.e., antibodies possessing human variable domains and mouse constant domains) were obtained. In addition, several fully human anti-PRLR antibodies were isolated directly from antigen-positive B cells without fusion to myeloma cells, as described in US 2007/0280945A1.

Certain biological properties of the exemplary anti-PRLR antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-PRLR antibodies of the invention. The corresponding nucleic acid sequence identifiers are set forth in Table 2.

TABLE 1

| | Amino Acid Sequence Identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H6762P | 2 | 4 | 6 | 8 | 10 | 12 | 14 | 16 |
| H1H6765P | 18 | 20 | 22 | 24 | 26 | 28 | 30 | 32 |
| H1H6774P | 34 | 36 | 38 | 40 | 42 | 44 | 46 | 48 |
| H1H6781P | 50 | 52 | 54 | 56 | 58 | 60 | 62 | 64 |
| H1H6782P | 66 | 68 | 70 | 72 | 74 | 76 | 78 | 80 |
| H1H6783P | 82 | 84 | 86 | 88 | 90 | 92 | 94 | 96 |
| H1H6785P | 98 | 100 | 102 | 104 | 106 | 108 | 110 | 112 |
| H1H6790P | 114 | 116 | 118 | 120 | 122 | 124 | 126 | 128 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H6792P | 130 | 132 | 134 | 136 | 138 | 140 | 142 | 144 |
| H1H6793P | 146 | 148 | 150 | 152 | 154 | 156 | 158 | 160 |
| H1H6795P | 162 | 164 | 166 | 168 | 170 | 172 | 174 | 176 |
| H1H6797P | 178 | 180 | 182 | 184 | 186 | 188 | 190 | 192 |
| H1H6800P | 194 | 196 | 198 | 200 | 202 | 204 | 206 | 208 |
| H1H6801P | 210 | 212 | 214 | 216 | 218 | 220 | 222 | 224 |
| H1H6803P | 226 | 228 | 230 | 232 | 234 | 236 | 238 | 240 |
| H1H6804P | 242 | 244 | 246 | 248 | 250 | 252 | 254 | 256 |
| H1H6807P | 258 | 260 | 262 | 264 | 266 | 268 | 270 | 272 |
| H1M6953N | 274 | 276 | 278 | 280 | 282 | 284 | 286 | 288 |
| H2M6958N2 | 290 | 292 | 294 | 296 | 298 | 300 | 302 | 304 |
| H2M6959N2 | 306 | 308 | 310 | 312 | 314 | 316 | 318 | 320 |
| H2M6960N | 322 | 324 | 326 | 328 | 330 | 332 | 334 | 336 |
| H2M6966N | 338 | 340 | 342 | 344 | 346 | 348 | 350 | 352 |
| H2M6967N | 354 | 356 | 358 | 360 | 362 | 364 | 366 | 368 |
| H2M6975N | 370 | 372 | 374 | 376 | 378 | 380 | 382 | 384 |
| H2M6976N | 386 | 388 | 390 | 392 | 394 | 396 | 398 | 400 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H6762P | 1 | 3 | 5 | 7 | 9 | 11 | 13 | 15 |
| H1H6765P | 17 | 19 | 21 | 23 | 25 | 27 | 29 | 31 |
| H1H6774P | 33 | 35 | 37 | 39 | 41 | 43 | 45 | 47 |
| H1H6781P | 49 | 51 | 53 | 55 | 57 | 59 | 61 | 63 |
| H1H6782P | 65 | 67 | 69 | 71 | 73 | 75 | 77 | 79 |
| H1H6783P | 81 | 83 | 85 | 87 | 89 | 91 | 93 | 95 |
| H1H6785P | 97 | 99 | 101 | 103 | 105 | 107 | 109 | 111 |
| H1H6790P | 113 | 115 | 117 | 119 | 121 | 123 | 125 | 127 |
| H1H6792P | 129 | 131 | 133 | 135 | 137 | 139 | 141 | 143 |
| H1H6793P | 145 | 147 | 149 | 151 | 153 | 155 | 157 | 159 |
| H1H6795P | 161 | 163 | 165 | 167 | 169 | 171 | 173 | 175 |
| H1H6797P | 177 | 179 | 181 | 183 | 185 | 187 | 189 | 191 |
| H1H6800P | 193 | 195 | 197 | 199 | 201 | 203 | 205 | 207 |
| H1H6801P | 209 | 211 | 213 | 215 | 217 | 219 | 221 | 223 |
| H1H6803P | 225 | 227 | 229 | 231 | 233 | 235 | 237 | 239 |
| H1H6804P | 241 | 243 | 245 | 247 | 249 | 251 | 253 | 255 |
| H1H6807P | 257 | 259 | 261 | 263 | 265 | 267 | 269 | 271 |
| H1M6953N | 273 | 275 | 277 | 279 | 281 | 283 | 285 | 287 |
| H2M6958N2 | 289 | 291 | 293 | 295 | 297 | 299 | 301 | 303 |
| H2M6959N2 | 305 | 307 | 309 | 311 | 313 | 315 | 317 | 319 |
| H2M6960N | 321 | 323 | 325 | 327 | 329 | 331 | 333 | 335 |
| H2M6966N | 337 | 339 | 341 | 343 | 345 | 347 | 349 | 351 |
| H2M6967N | 353 | 355 | 357 | 359 | 361 | 363 | 365 | 367 |
| H2M6975N | 369 | 371 | 373 | 375 | 377 | 379 | 381 | 383 |
| H2M6976N | 385 | 387 | 389 | 391 | 393 | 395 | 397 | 399 |

Antibodies are typically referred to herein according to the following nomenclature: Fc prefix (e.g. "H1H," "H1M," "H2M," etc.), followed by a numerical identifier (e.g. "6762," "6953," "6958," etc.), followed by a "P" or "N" suffix, as shown in Tables 1 and 2. Thus, according to this nomenclature, an antibody may be referred to herein as, e.g., "H1H6762P," "H1M6953N," "H2M6958N," etc. The H1H, H1M and H2M prefixes on the antibody designations used herein indicate the particular Fc region isotype of the antibody. For example, an "H1H" antibody has a human IgG1 Fc, an "H1M" antibody has a mouse IgG1 Fc, and an "H2M" antibody has a mouse IgG2 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Control Constructs Used in the Following Examples

Control constructs were included in the following experiments for comparative purposes: Control I: a human anti-PRLR antibody with heavy and light chain variable domains having the amino acid sequences of the corresponding domains of "he.06.642-2," as set forth in WO2008/02295A2; and Control II: a human anti-ErbB2 antibody with

Example 3. Surface Plasmon Resonance Derived Binding Affinities and Kinetic Constants of Human Monoclonal Anti-PRLR Antibodies Binding affinities and kinetic constants of human monoclonal anti-PRLR antibodies were determined by surface plasmon resonance at 25° C. and 37° C. Antibodies, expressed as human IgG1 Fc "H1H" designations), were captured onto an anti-human Fc sensor surface (mAb-capture format), and soluble monomeric (hPRLR.mmh; SEQ ID NO:401, or *Macaca fascicularis* (mf) PRLR.mmh; SEQ ID NO:403) or dimeric (hPRLR.mFc; SEQ ID NO:402) PRLR protein was injected over the sensor surface. Measurements were conducted on a T200 Biacore instrument. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(ln 2/(60*$k_d$). Results are summarized in Tables 3 and 4.

TABLE 3

Biacore Binding Affinities of Human Fc mAbs at 25° C.
Binding at 25° C./Antibody-Capture Format

| Antibody | Analyte | ka (Ms$^{-1}$) | kd (s$^{-1}$) | $K_D$ (Molar) | T½ (min) |
|---|---|---|---|---|---|
| H1H6953N | hPRLR.mmh | 7.92E+05 | 2.12E−04 | 2.68E−10 | 54.5 |
|  | hPRLR.mFc | 7.11E+05 | 4.77E−05 | 6.70E−11 | 242.2 |
|  | mfPRLR.mmh | 7.27E+05 | 3.19E−04 | 4.38E−10 | 36.3 |
| H1H6958N2 | hPRLR.mmh | 2.33E+05 | 2.72E−04 | 1.17E−09 | 42.5 |
|  | hPRLR.mFc | 4.22E+05 | 3.66E−05 | 8.67E−11 | 315.8 |
|  | mfPRLR.mmh | 1.95E+05 | 2.80E−04 | 1.44E−09 | 41.3 |
| H1H6959N2 | hPRLR.mmh | 1.79E+05 | 3.60E−02 | 2.02E−07 | 0.3 |
|  | hPRLR.mFc | 3.59E+05 | 5.18E−04 | 1.45E−09 | 22.3 |
|  | mfPRLR.mmh | 1.29E+05 | 1.67E−02 | 1.29E−07 | 0.7 |
| H1H6960N | hPRLR.mmh | 1.08E+05 | 7.29E−04 | 6.74E−09 | 15.8 |
|  | hPRLR.mFc | 2.52E+05 | 3.56E−05 | 1.41E−10 | 324.4 |
|  | mfPRLR.mmh | 9.40E+04 | 5.83E−04 | 6.20E−09 | 19.8 |
| H1H6966N | hPRLR.mmh | 8.52E+05 | 2.57E−04 | 3.02E−10 | 44.9 |
|  | hPRLR.mFc | 9.31E+05 | 4.08E−05 | 4.39E−11 | 282.9 |
|  | mfPRLR.mmh | 7.82E+05 | 3.25E−04 | 4.16E−10 | 35.6 |
| H1H6967N | hPRLR.mmh | 2.46E+05 | 3.32E−04 | 1.35E−09 | 34.8 |
|  | hPRLR.mFc | 4.07E+05 | 4.45E−05 | 1.10E−10 | 259.3 |
|  | mfPRLR.mmh | 1.90E+05 | 5.85E−04 | 3.08E−09 | 19.7 |
| H1H6975N | hPRLR.mmh | 1.50E+05 | 7.35E−05 | 4.90E−10 | 157.1 |
|  | hPRLR.mFc | 2.87E+05 | 1.97E−05 | 6.84E−11 | 587.8 |
|  | mfPRLR.mmh | 1.15E+05 | 1.31E−04 | 1.14E−09 | 88.2 |
| H1H6976N | hPRLR.mmh | 5.44E+05 | 8.64E−04 | 1.59E−09 | 13.4 |
|  | hPRLR.mFc | 1.12E+06 | 1.01E−04 | 9.06E−11 | 114.4 |
|  | mfPRLR.mmh | 4.66E+05 | 8.14E−04 | 1.75E−09 | 14.2 |
| H1H6762P | hPRLR.mmh | 6.92E+05 | 1.79E−04 | 2.59E−10 | 64 |
|  | hPRLR.mFc | 6.51E+05 | 6.45E−05 | 9.92E−11 | 179 |
|  | mfPRLR.mmh | 4.08E+05 | 2.08E−04 | 5.11E−10 | 55 |
| H1H6765P | hPRLR.mmh | 9.07E+05 | 1.13E−04 | 1.24E−10 | 102 |
|  | hPRLR.mFc | 8.69E+05 | 3.41E−05 | 3.92E−11 | 339 |
|  | mfPRLR.mmh | 5.27E+05 | 1.34E−04 | 2.54E−10 | 86 |
| H1H6774P | hPRLR.mmh | 7.15E+05 | 8.18E−04 | 1.14E−09 | 14 |
|  | hPRLR.mFc | 7.98E+05 | 8.94E−05 | 1.12E−10 | 129 |
|  | mfPRLR.mmh | 4.95E+05 | 8.75E−04 | 1.77E−09 | 13 |
| H1H6781P | hPRLR.mmh | 2.08E+05 | 1.27E−04 | 6.10E−10 | 91 |
|  | hPRLR.mFc | 2.57E+05 | 6.05E−05 | 2.36E−10 | 191 |
|  | mfPRLR.mmh | 1.43E+05 | 1.41E−04 | 9.86E−10 | 82 |
| H1H6782P | hPRLR.mmh | 3.60E+05 | 2.47E−04 | 6.85E−10 | 47 |
|  | hPRLR.mFc | 3.17E+05 | 7.13E−05 | 2.25E−10 | 162 |
|  | mfPRLR.mmh | 2.66E+05 | 2.79E−04 | 1.05E−09 | 41 |
| H1H6783P | hPRLR.mmh | 2.88E+05 | 4.13E−04 | 1.43E−09 | 28 |
|  | hPRLR.mFc | 2.64E+05 | 8.77E−05 | 3.32E−10 | 132 |
|  | mfPRLR.mmh | 1.89E+05 | 3.41E−04 | 1.81E−09 | 34 |
| H1H6785P | hPRLR.mmh | 3.01E+05 | 1.71E−04 | 5.67E−10 | 68 |
|  | hPRLR.mFc | 2.63E+05 | 6.07E−05 | 2.31E−10 | 190 |
|  | mfPRLR.mmh | 2.27E+05 | 1.67E−04 | 7.38E−10 | 69 |
| H1H6790P | hPRLR.mmh | 5.65E+05 | 7.99E−04 | 1.41E−09 | 14 |
|  | hPRLR.mFc | 5.42E+05 | 1.04E−04 | 1.92E−10 | 111 |
|  | mfPRLR.mmh | 3.89E+05 | 7.93E−04 | 2.04E−09 | 15 |
| H1H6792P | hPRLR.mmh | 3.24E+05 | 7.94E−04 | 2.45E−09 | 15 |
|  | hPRLR.mFc | 3.03E+05 | 9.48E−05 | 3.13E−10 | 122 |
|  | mfPRLR.mmh | 2.36E+05 | 9.83E−04 | 4.17E−09 | 12 |
| H1H6793P | hPRLR.mmh | 2.35E+05 | 3.32E−04 | 1.41E−09 | 35 |
|  | hPRLR.mFc | 2.29E+05 | 7.57E−05 | 3.31E−10 | 153 |
|  | mfPRLR.mmh | 1.77E+05 | 3.93E−04 | 2.22E−09 | 29 |
| H1H6795P | hPRLR.mmh | 1.17E+06 | 1.77E−03 | 1.52E−09 | 7 |
|  | hPRLR.mFc | 1.54E+06 | 8.41E−05 | 5.45E−11 | 137 |
|  | mfPRLR.mmh | 8.44E+05 | 1.97E−03 | 2.33E−09 | 6 |
| H1H6797P | hPRLR.mmh | 1.13E+06 | 1.96E−03 | 1.73E−09 | 6 |
|  | hPRLR.mFc | 9.82E+05 | 1.19E−04 | 1.22E−10 | 97 |
|  | mfPRLR.mmh | 6.70E+05 | 2.09E−03 | 3.12E−09 | 6 |
| H1H6800P | hPRLR.mmh | 4.21E+05 | 4.09E−04 | 9.72E−10 | 28 |
|  | hPRLR.mFc | 4.73E+05 | 8.69E−05 | 1.84E−10 | 133 |
|  | mfPRLR.mmh | 3.03E+05 | 3.80E−04 | 1.25E−09 | 30 |
| H1H6801P | hPRLR.mmh | 8.46E+05 | 7.56E−04 | 8.94E−10 | 15 |
|  | hPRLR.mFc | 6.75E+05 | 1.09E−04 | 1.61E−10 | 106 |
|  | mfPRLR.mmh | 6.57E+05 | 1.23E−03 | 1.88E−09 | 9 |
| H1H6803P | hPRLR.mmh | 8.24E+04 | 1.37E−04 | 1.67E−09 | 84 |
|  | hPRLR.mFc | 1.04E+05 | 6.29E−05 | 6.07E−10 | 184 |
|  | mfPRLR.mmh | 6.21E+04 | 2.09E−04 | 3.37E−09 | 55 |
| H1H6804P | hPRLR.mmh | 4.53E+05 | 6.34E−04 | 1.40E−09 | 18 |
|  | hPRLR.mFc | 4.51E+05 | 8.69E−05 | 1.93E−10 | 133 |
|  | mfPRLR.mmh | 3.31E+05 | 6.57E−04 | 1.99E−09 | 18 |
| H1H6807P | hPRLR.mmh | 7.61E+05 | 1.44E−04 | 1.89E−10 | 80 |
|  | hPRLR.mFc | 6.80E+05 | 5.46E−05 | 8.03E−11 | 212 |
|  | mfPRLR.mmh | 4.37E+05 | 1.51E−04 | 3.46E−10 | 76 |
| Control I | hPRLR.mmh | 5.11E+05 | 7.44E−04 | 1.46E−09 | 15.5 |
|  | hPRLR.mFc | 4.72E+05 | 7.53E−05 | 1.59E−10 | 153.5 |
|  | mfPRLR.mmh | 2.38E+05 | 6.14E−03 | 2.59E−08 | 1.9 |

NB = No binding observed under conditions used

TABLE 4

Biacore Binding Affinities of Human Fc mAbs at 37° C.
Binding at 37° C./Antibody-Capture Format

| Antibody | Analyte | ka (Ms$^{-1}$) | kd (s$^{-1}$) | $K_D$ (Molar) | T½ (min) |
|---|---|---|---|---|---|
| H1H6953N | hPRLR.mmh | 1.10E+06 | 1.22E−03 | 1.11E−09 | 9.4 |
|  | hPRLR.mFc | 1.47E+06 | 1.70E−04 | 1.16E−10 | 68.0 |
|  | mfPRLR.mmh | 9.47E+05 | 2.56E−03 | 2.71E−09 | 4.5 |
| H1H6958N2 | hPRLR.mmh | 4.13E+05 | 1.31E−03 | 3.16E−09 | 8.8 |
|  | hPRLR.mFc | 8.29E+05 | 1.39E−04 | 1.67E−10 | 83.3 |
|  | mfPRLR.mmh | 3.28E+05 | 1.34E−03 | 4.08E−09 | 8.6 | heavy and light chain variable domains having the amino acid sequences of the corresponding domains of "4D5v8" as set forth in: Carter et al., 1992, Proc. Natl. Acad. Sci. USA, 89:4285-4289.

TABLE 4-continued

Biacore Binding Affinities of Human Fc mAbs at 37° C.
Binding at 37° C./Antibody-Capture Format

| Antibody | Analyte | ka (Ms$^{-1}$) | kd (s$^{-1}$) | $K_D$ (Molar) | T½ (min) |
|---|---|---|---|---|---|
| H1H6959N2 | hPRLR.mmh | 4.06E+04 | 2.77E−02 | 6.81E−07 | 0.4 |
|  | hPRLR.mFc | 5.09E+05 | 2.30E−03 | 4.51E−09 | 5.0 |
|  | mfPRLR.mmh | 4.46E+04 | 1.65E−02 | 3.70E−07 | 0.7 |
| H1H6960N | hPRLR.mmh | 1.22E+05 | 1.98E−03 | 1.62E−08 | 5.8 |
|  | hPRLR.mFc | 2.94E+05 | 1.47E−04 | 5.00E−10 | 78.7 |
|  | mfPRLR.mmh | 8.64E+04 | 1.28E−03 | 1.49E−08 | 9.0 |
| H1H6966N | hPRLR.mmh | 1.58E+06 | 9.60E−04 | 6.07E−10 | 12.0 |
|  | hPRLR.mFc | 1.88E+06 | 1.27E−04 | 6.72E−11 | 91.3 |
|  | mfPRLR.mmh | 1.22E+06 | 1.20E−03 | 9.82E−10 | 9.6 |
| H1H6967N | hPRLR.mmh | 4.24E+05 | 9.33E−04 | 2.20E−09 | 12.4 |
|  | hPRLR.mFc | 9.07E+05 | 9.73E−05 | 1.07E−10 | 118.8 |
|  | mfPRLR.mmh | 3.56E+05 | 1.62E−03 | 4.54E−09 | 7.1 |
| H1H6975N | hPRLR.mmh | 2.11E+05 | 2.73E−04 | 1.29E−09 | 42.3 |
|  | hPRLR.mFc | 3.86E+05 | 7.09E−05 | 1.84E−10 | 163.0 |
|  | mfPRLR.mmh | 1.40E+05 | 3.17E−04 | 2.27E−09 | 36.4 |
| H1H6976N | hPRLR.mmh | 7.77E+05 | 3.14E−03 | 4.04E−09 | 3.7 |
|  | hPRLR.mFc | 1.37E+06 | 1.40E−04 | 1.02E−10 | 82.6 |
|  | mfPRLR.mmh | 6.03E+05 | 3.16E−03 | 5.24E−09 | 3.7 |
| H1H6762P | hPRLR.mmh | 9.48E+05 | 4.55E−04 | 4.80E−10 | 25 |
|  | hPRLR.mFc | 8.01E+05 | 1.03E−04 | 1.28E−10 | 112 |
|  | mfPRLR.mmh | 6.79E+05 | 5.58E−04 | 8.23E−10 | 21 |
| H1H6765P | hPRLR.mmh | 1.25E+06 | 3.66E−04 | 2.92E−10 | 32 |
|  | hPRLR.mFc | 8.01E+05 | 1.03E−04 | 1.28E−10 | 112 |
|  | mfPRLR.mmh | 1.06E+06 | 5.37E−05 | 5.04E−11 | 215 |
| H1H6774P | hPRLR.mmh | 1.07E+06 | 3.17E−03 | 2.95E−09 | 4 |
|  | hPRLR.mFc | 1.41E+06 | 1.94E−04 | 1.38E−10 | 60 |
|  | mfPRLR.mmh | 7.23E+05 | 3.61E−03 | 5.00E−09 | 3 |
| H1H6781P | hPRLR.mmh | 3.39E+05 | 3.09E−04 | 9.10E−10 | 37 |
|  | hPRLR.mFc | 4.36E+05 | 9.84E−05 | 2.26E−10 | 117 |
|  | mfPRLR.mmh | 2.47E+05 | 2.67E−04 | 1.08E−09 | 43 |
| H1H6782P | hPRLR.mmh | 5.57E+05 | 7.16E−04 | 1.28E−09 | 16 |
|  | hPRLR.mFc | 5.98E+05 | 1.30E−04 | 2.17E−10 | 89 |
|  | mfPRLR.mmh | 3.85E+05 | 7.67E−04 | 1.99E−09 | 15 |
| H1H6783P | hPRLR.mmh | 4.11E+05 | 1.61E−03 | 3.91E−09 | 7 |
|  | hPRLR.mFc | 4.91E+05 | 1.38E−04 | 2.82E−10 | 83 |
|  | mfPRLR.mmh | 2.73E+05 | 1.30E−03 | 4.74E−09 | 9 |
| H1H6785P | hPRLR.mmh | 4.26E+05 | 4.84E−04 | 1.14E−09 | 24 |
|  | hPRLR.mFc | 4.56E+05 | 1.17E−04 | 2.56E−10 | 99 |
|  | mfPRLR.mmh | 2.97E+05 | 4.50E−04 | 1.52E−09 | 26 |
| H1H6790P | hPRLR.mmh | 9.40E+05 | 3.29E−03 | 3.50E−09 | 4 |
|  | hPRLR.mFc | 6.46E+05 | 1.98E−04 | 3.06E−10 | 58 |
|  | mfPRLR.mmh | 6.15E+05 | 3.21E−03 | 5.22E−09 | 4 |
| H1H6792P | hPRLR.mmh | 4.35E+05 | 2.29E−03 | 5.27E−09 | 5 |
|  | hPRLR.mFc | 4.99E+05 | 1.76E−04 | 3.52E−10 | 66 |
|  | mfPRLR.mmh | 3.05E+05 | 2.86E−03 | 9.37E−09 | 4 |
| H1H6793P | hPRLR.mmh | 3.39E+05 | 1.02E−03 | 3.02E−09 | 11 |
|  | hPRLR.mFc | 4.10E+05 | 1.42E−04 | 3.47E−10 | 81 |
|  | mfPRLR.mmh | 2.33E+05 | 1.07E−03 | 4.59E−09 | 11 |
| H1H6795P | hPRLR.mmh | 1.36E+06 | 5.20E−03 | 3.81E−09 | 2 |
|  | hPRLR.mFc | 1.94E+06 | 7.77E−05 | 4.02E−11 | 149 |
|  | mfPRLR.mmh | 9.73E+05 | 5.99E−03 | 6.16E−09 | 2 |
| H1H6797P | hPRLR.mmh | 1.29E+06 | 8.22E−03 | 6.37E−09 | 1 |
|  | hPRLR.mFc | 1.80E+06 | 1.25E−04 | 6.91E−11 | 93 |
|  | mfPRLR.mmh | 9.14E+05 | 9.06E−03 | 9.90E−09 | 1 |
| H1H6800P | hPRLR.mmh | 8.08E+05 | 1.19E−03 | 1.47E−09 | 10 |
|  | hPRLR.mFc | 6.44E+05 | 1.47E−04 | 2.29E−10 | 79 |
|  | mfPRLR.mmh | 4.39E+05 | 1.09E−03 | 2.48E−09 | 11 |
| H1H6801P | hPRLR.mmh | 9.51E+05 | 4.41E−03 | 4.63E−09 | 3 |
|  | hPRLR.mFc | 7.93E+05 | 2.21E−04 | 2.79E−10 | 52 |
|  | mfPRLR.mmh | 7.11E+05 | 7.71E−03 | 1.08E−08 | 1 |
| H1H6803P | hPRLR.mmh | 1.29E+05 | 3.64E−04 | 2.83E−09 | 32 |
|  | hPRLR.mFc | 1.34E+05 | 6.20E−05 | 4.61E−10 | 186 |
|  | mfPRLR.mmh | 8.73E+04 | 6.36E−04 | 7.28E−09 | 18 |
| H1H6804P | hPRLR.mmh | 6.07E+05 | 3.85E−03 | 6.34E−09 | 3 |
|  | hPRLR.mFc | 5.54E+05 | 2.05E−04 | 3.69E−10 | 56 |
|  | mfPRLR.mmh | 4.55E+05 | 4.26E−03 | 9.35E−09 | 3 |
| H1H6807P | hPRLR.mmh | 1.08E+06 | 3.36E−04 | 3.10E−10 | 34 |
|  | hPRLR.mFc | 1.22E+06 | 1.10E−04 | 9.00E−11 | 105 |
|  | mfPRLR.mmh | 8.02E+05 | 3.59E−04 | 4.48E−10 | 32 |
| Control I | hPRLR.mmh | 5.99E+05 | 2.42E−03 | 4.04E−09 | 4.8 |
|  | hPRLR.mFc | 8.47E+05 | 2.14E−04 | 2.53E−10 | 54.0 |
|  | mfPRLR.mmh | 1.53E+05 | 1.54E−02 | 1.01E−07 | 0.8 |

NB = No binding observed under conditions used

As shown in Tables 3 and 4, several antibodies of the invention displayed sub-nanomolar affinities to human and monkey PRLR protein and exhibited higher affinity than the comparator anti-PRLR antibody (Control I). For example, at 37° C., many of the anti-PRLR antibodies of the invention bound to monomeric human PRLR with $K_D$ values less than 4 nM and T % times greater than 5 minutes; and to dimeric human PRLR with $K_D$ values less than 250 pM and T % times greater than 60 minutes. These binding characteristics are substantially better than what was observed with the Control I antibody under the same experimental conditions.

Example 4A. Anti-PRLR Antibodies Bind to Endogenous and Overexpressed PRLR Cell Lines The ability of anti-PRLR antibodies to selectively bind PRLR expressing cell lines was next determined. Human, monkey *Macaca fascicularis*, and mouse PRLR constructs with an HA tag were stably introduced into HEK293 cells via Lipofectamine 2000-mediated transfection methodology. Transfectants (HEK293/hPRLR, HEK293/mfPRLR and HEK293/mPRLR) were selected for at least 2 weeks in complete growth media plus G418.

Cell surface expression of PRLR on 293/hPRLR cells was assessed via FACS analysis. Briefly, $1 \times 10^5$ cells were incubated with 10 μg/ml of Control antibody I, or an isotype control for 30 min on ice in antibody dilution buffer. Following two washes with antibody dilution buffer, cells were incubated with 10 μg/ml of PE conjugated anti-human secondary antibodies for 30 min on ice. Following two additional washes, samples were run on a Hypercyt® cytometer and analyzed in ForeCyt™ (IntelliCyt, Albuquerque, N. Mex.). The mean fluorescence intensities (MFI) were expressed as fold change above isotype control levels (background). FACS binding confirmed that Control I selectively bound to 293/hPRLR expressing cells with MFIs that were 30 fold above background (isotype ctrl) levels and less than 2 fold binding on parental cells.

Cell surface copy number of PRLR was also quantitatively determined on T47D, MCF7 and MCF7/hPRLR-overexpressing cell lines. Briefly, $1 \times 10^5$ cells were incubated with 100 nM of the anti-PRLR antibody H1H6953N-Alexa647 for 30 min on ice in antibody dilution buffer. Following two washes with antibody dilution buffer, samples were run on a Hypercyt® cytometer (IntelliCyt, Albuquerque, N. Mex.) and the mean fluorescence intensities (MFI) were determined in ForeCyt™ (IntelliCyt, Albuquerque, N. Mex.). The MFI for each cell line was then converted to Alexa647 molecules of equivalent soluble fluorescence (MESF) via the Quantum Alexa Fluor 647 MESF kit according to manufacturer instructions (Bangs Laboratories, Inc, Fishers, Ind.). The average number of fluorophores per H1H6953N-A647 protein (F/P ratio) was determined via the Simply Cellular anti-Human IgG kit according to manufacture instructions (Bangs Laboratories, Inc, Fishers, Ind.). The MESF values were divided by the F/P ratio to determine the PRLR cell surface copy number or H1H6953N antigen binding capacity on each cell line. Using this method, it was determined that the approximate cell surface copy number of PRLR on the various cell lines was as follows: T47D=27,000; MCF7=3,000; and MCF7/hPRLR=190,000.

Next, the anti-PRLR antibodies of the present invention were tested via FACS for selective binding to the engineered overexpressing PRLR HEK293 cell lines, as well as to non-expressing HEK293 cells and a native PRLR expressing cell line (T47D). Results are shown in Table 5.

TABLE 5

FACS Cell Surface Binding of Anti-PRLR Antibodies

| Antibody | FACS Cell Binding (Fold Above Background) | | | | |
|---|---|---|---|---|---|
| | HEK293 | HEK293/ hPRLR | HEK293/ mfPRLR | HEK293/ mPRLR | T47D |
| unstained | 1 | 1 | 1 | 1 | 1 |
| Secondary only | 1 | 1 | 1 | 1 | 1 |
| Control I | 1 | 31 | 13 | 7 | 30 |
| *H1H6762P | 1 | 36 | 26 | 2 | 38 |
| *H1H6765P | 2 | 38 | 27 | 1 | 40 |
| H1H6774P | 1 | 1 | 29 | 1 | 39 |
| *H1H6781P | 1 | 37 | 26 | 1 | 40 |
| H1H6782P | 3 | 41 | 32 | 4 | 43 |
| *H1H6783P | 1 | 37 | 27 | 1 | 38 |
| *H1H6785P | 1 | 37 | 26 | 2 | 40 |
| *H1H6790P | 1 | 37 | 24 | 1 | 34 |
| *H1H6792P | 1 | 37 | 28 | 3 | 37 |
| H1H6793P | 2 | 2 | 32 | 2 | 43 |
| H1H6795P | 1 | 1 | 22 | 1 | 34 |
| H1H6797P | 1 | 1 | 25 | 2 | 38 |
| *H1H6800P | 1 | 35 | 29 | 1 | 41 |
| H1H6801P | 7 | 47 | 88 | 56 | 45 |
| *H1H6803P | 1 | 39 | 28 | 1 | 39 |
| H1H6804P | 1 | 1 | 29 | 1 | 34 |
| *H1H6807P | 2 | 32 | 27 | 2 | 34 |
| *H1H6953N | 2 | 37 | 29 | 2 | 40 |
| *H1H6958N2 | 1 | 35 | 30 | 1 | 37 |
| H1H6959N2 | 1 | 6 | 11 | 2 | 9 |
| *H1H6960N | 1 | 29 | 23 | 1 | 33 |
| *H1H6966N | 1 | 29 | 18 | 1 | 31 |
| *H1H6967N | 1 | 38 | 28 | 2 | 41 |
| *H1H6975N | 1 | 38 | 29 | 1 | 46 |
| H1H6976N | 1 | 8 | 29 | 1 | 37 |
| Isotype Ctrl I | 1 | 1 | 1 | 1 | NA |
| Isotype Ctrl II | 1 | 1 | NA | NA | 1 |

*Denotes antibodies with specific binding on HEK293/hPRLR, HEK293/mfPRLR and T47D and less than 2-fold binding on HEK293 parental cells.

As shown in Table 5, a majority of the anti-human PRLR antibodies specifically bound to HEK293/PRLR cells at >25-fold above background levels with negligible binding to parental cells. Antibodies that bound to human PRLR were similarly shown to bind to monkey (*Macaca fascicularis*) PRLR on HEK293/mfPRLR cells. Antibodies that were identified to be strong binders to HEK293/hPRLR cells were similarly shown to be robust binders to native PRLR expressing T47D cells. Cross-reactivity to rodent PRLR was not observed.

In summary, antibodies of this invention displayed strong binding to human and monkey PRLR on engineered cell lines as well as endogenously expressed PRLR.

Example 4B. Anti-PRLR Antibodies are Internalized by PRLR-Expressing Cells In Vitro In this Example, the internalization of anti-PRLR antibodies by PRLR-expressing cells (T47D) was assessed. Briefly, 20,000 T47D cells were seeded in collagen coated 96 well plates. The next day, cells were incubated with anti-human PRLR antibodies (10 μg/ml) for 30 min on ice followed by two PBS washes. Cells were then incubated with alexa488 conjugated anti-hFc Fab secondary antibodies for 30 minutes on ice followed by two additional PBS washes. Antibodies were allowed to internalize for 1 h at 37° C. in internalization buffer (PBS+2% FBS) or remained at 4° C. Cells were fixed in 4% formaldehyde, nuclei were stained with DRAQS (Cell signaling), and images were acquired on the ImageXpress micro XL (Molecular Devices). Whole cell alexa488 intensity at 37° C. (Binding) and the alexa488 intensity in the intracellular vesicles at 37° C. (Internalization) were determined via Columbus image analysis software (PerkinElmer). The intensities are expressed as a percentage of the strongest internalizing antibody, H1H6975N, and are summarized in Table 6.

TABLE 6

Cell Line: T47D
[mAb] 1 μg/mL (0.67 nM)

| Antibody | % Internalization relative to Control I | % Total Binding relative to Control I |
|---|---|---|
| anti-PRLR control I | 100.0 | 100.0 |
| H1H6975N | 214.2 | 225.9 |
| H1H6800P | 198.3 | 186.8 |
| H1H6803P | 190.5 | 205.5 |
| H1H6762P | 186.3 | 176.7 |
| H1H6765P | 186.3 | 191.3 |
| H1H6793P | 179.9 | 177.9 |
| H1H6782P | 179.3 | 209.9 |
| H1H6976N | 169.5 | 180.4 |
| H1H6785P | 169.1 | 168.0 |
| H1H6958N2 | 169.0 | 161.5 |
| H1H6967N | 168.6 | 158.6 |
| H1H6781P | 165.1 | 166.2 |
| H1H6774P | 162.3 | 173.7 |
| H1H6783P | 160.7 | 165.8 |
| H1H6792P | 155.9 | 110.6 |
| H1H6953N | 153.9 | 164.2 |
| H1H6795P | 150.7 | 123.4 |
| H1H6801P | 148.9 | 155.7 |
| H1H6807P | 147.0 | 152.7 |
| H1H6790P | 146.9 | 122.8 |
| H1H6797P | 145.2 | 151.2 |
| H1H6804P | 138.9 | 149.6 |
| H1H6966N | 137.2 | 111.3 |
| H1H6960N | 120.0 | 89.7 |
| H1H6959N2 | 15.3 | 2.0 |

With the exception of H1H6959N2, all tested antibodies bound T47D and nearly 100% of all bound mAbs internalized within 1 h. The total internalized antibody intensity for most antibodies was greater than the anti-human PRLR control antibody (Control I).

Example 5. Anti-PRLR Antibodies Inhibit PRL-Mediated Receptor Activation in Cells Expressing Human PRLR The ability of anti-PRLR antibodies to block prolactin (PRL)-mediated receptor activation was examined in a luciferase-based reporter assay. The endocrine hormone PRL binds to the extracellular domain of its cognate receptor PRLR, triggering rapid homodimerization and activating several downstream signaling cascades.

In this example, an engineered cell line was used to determine the ability of anti-PRLR antibodies to block ligand activation of the PRLR receptor. Briefly, HEK293/hPRLR/STAT5-Luc cell lines with stable incorporation of a human PRLR expression cassette and the STAT5-dependent luciferase reporter were generated via sequential rounds of Lipofectamine® 2000-mediated transfection (LifeTechnologies, Carlsbad, Calif.). Cells were selected for at least two weeks in the presence of 500 μg/mL G418 (hPRLR) and 100 μg/mL hygromycin B (STAT5-Luc). The STAT5-Luc assay utilized $2\times10^5$ HEK293/hPRLR/STAT5-Luc cells seeded in complete growth medium on PDL-coated 96 well plates grown overnight at 37° C., 5% $CO_2$. To generate antibody inhibition curves, cells were incubated (6 hr at 37° C.) with serially diluted anti-human PRLR antibodies (100 nM to 24 pM) in the presence of 5 nM constant PRL before recording signal. PRL dose response curves were generated by the addition of serially diluted PRL (100 nM to 24 pM) to cells and recording signal after a 6 hr (37° C.) incubation in the absence of antibodies. The ability of the antibodies to activate PRLR in the absence of ligand was also assessed.

Luciferase activity was measured with ONE-Glo™ reagent (Promega, Madison, Wis.). Relative light units (RLUs) were measured on a Victor luminometer (Perkin Elmer, Shelton, Conn.). $EC_{50}/IC_{50}$ values were determined from a four-parameter logistic equation over an 8-point response curve using GraphPad Prism. Percent blocking and percent activation are reported for the highest antibody dose. Results are shown in Table 7.

TABLE 7

$IC_{50}$ and Percent Blocking of PRL-Mediated Signaling by Anti-PRLR Antibodies

| Antibody | $IC_{50}$ of Blocking 5 nM PRL [M] | Percent Blocking at 100 nM Antibody |
|---|---|---|
| H1H6762P | 2.19E−11 | 100 |
| H1H6765P | 3.30E−11 | 100 |
| H1H6774P | NB | 0 |
| H1H6781P | 2.70E−11 | 100 |
| H1H6782P | NB | 0 |
| H1H6783P | ND | 59 |
| H1H6785P | 3.45E−10 | 100 |
| H1H6790P | 2.06E−10 | 100 |
| H1H6792P | 5.70E−10 | 100 |
| H1H6793P | ND | 65 |
| H1H6795P | NB | 0 |
| H1H6797P | NB | 0 |
| H1H6800P | 3.55E−10 | 100 |
| H1H6801P | 1.40E−10 | 100 |
| H1H6803P | 6.27E−10 | 100 |
| H1H6804P | 7.89E−09 | 100 |
| H1H6807P | 6.00E−10 | 100 |
| H1H6953N | 1.05E−10 | 100 |
| H1H6958N2 | 1.98E−10 | 100 |
| H1H6959N2 | ND | 52 |
| H1H6960N | 1.58E−09 | 100 |
| H1H6966N | ND | 54 |
| H1H6967N | 7.68E−10 | 100 |
| H1H6975N | 2.41E−10 | 100 |
| H1H6976N | ND | 23 |
| Control I | 1.33E−09 | 100 |

NB: Not blocking;
ND: Not determined due to incomplete blocking

As summarized in Table 7, a majority of the antibodies of this invention inhibited activation of the STAT5 reporter, with $IC_{50}$ values ranging from 22 pM to 8 nM. All inhibitory antibodies blocked activation to baseline levels (100 percent blocking). Additionally, the antibodies tested in this assay did not activate STAT5 in the absence of PRL ligand.

In summary, the data of this Example show that a majority of the anti-PRLR antibodies of the invention block PRL-mediated receptor activation. Additionally, a majority of the antibodies inhibit receptor activation more potently than the anti-PRLR Control I antibody. For example, several anti-PRLR antibodies of the present invention blocked prolactin-mediated signaling with $IC_{50}$ values of less than about 1.3 nM. On the other hand, certain anti-PRLR antibodies of the invention, despite being able to bind PRLR, did not exhibit prolactin blocking activity. Such non-blocking anti-PRLR antibodies may find uses in various therapeutic contexts where PRLR targeting is desired without interfering with normal prolactin-mediated signaling.

Example 6. Preparation and Characterization of Anti-PRLR Antibody Drug Conjugates Selected anti-PRLR antibodies were conjugated to the maytansinoid DM1 through an SMCC linker using methods similar to those set forth in U.S. Pat. No. 5,208,020 and US Patent Application Publication No. 2010/0129314, the disclosures of which are incorporated by reference herein in their entireties. The conjugates were purified by size exclusion chromatography and sterile filtered. All starting materials and solvents were purchased commercially and used without purification, unless otherwise noted.

Protein and linker/payload concentrations were determined by UV spectral analysis and MALDI-TOF mass spectrometry. Size-exclusion HPLC established that all conjugates used were >95% monomeric, and RP-HPLC established that there was <0.5% unconjugated linker payload. Yields are reported in Table 8 and 9 based on protein. All conjugated antibodies were analyzed by UV for linker payload loading values according to Hamblett et al, 2004, Clinical Cancer Research 10(20):7063-7070, and by mass difference, native versus conjugated.

TABLE 8

Protein Concentrations for Anti-PRLR Unconjugated Antibodies

| Compound | ε252 nm (cm$^{-1}$ M$^{-1}$) | ε280 nm (cm$^{-1}$ M$^{-1}$) |
|---|---|---|
| SMCC-DM1 | 26790 | 5700 |
| Antibody (unconjugated) | | |
| H1H6958N2 | 74462 | 195440 |
| H1H6959N2 | 77485 | 209420 |
| H1H6960N | 84926 | 214460 |
| H1H6953N | 80673 | 220420 |
| H1H6975P | 81120 | 199804 |
| Isotype Control | 84723 | 218360 |

TABLE 9

Antibody Linker/Payload Concentrations for Anti-PRLR-SMCC-DM1 Conjugates

| Antibody Conjugate | Payload:Antibody Molar Ratio (UV) | Payload:Antibody Molar Ratio (MS) | Yield % |
|---|---|---|---|
| H1H6958N2-DM1 | 4.0 | 3.4 | 64 |
| H1H6959N2-DM1 | 3.8 | 3.3 | 64 |
| H1H6960N-DM1 | 3.6 | 3.0 | 64 |
| H1H6953N-DM1 | 3.2 | 2.7 | 52 |
| H1H6803P-DM1 | ND | 3.1 | 55 |
| H1H6762P-DM1 | ND | 2.9 | 70 |
| H1H6765P-DM1 | ND | 2.3 | 55 |
| H1H6782P-DM1 | ND | 2.8 | 65 |
| H1H6793P-DM1 | ND | 3.8 | 55 |
| H1H6975P-DM1 | 3.0 | 3.4 | 60 |
| H1H6800P-DM1 | 3.0 | 3.2 | 50 |
| Isotype Control-DM1 | 3.3 | 3.3 | 80 |

ND: not determined

This Example illustrates the conjugation of anti-PRLR antibodies of the present invention with DM1 through an SMCC linker. The payload: antibody molar ratio was calculated to be from about 2.3 to about 3.8 for the conjugated antibodies of this Example. Percent yields for the antibodies of the invention ranged from around 50% to 70%.

Example 7. Anti-PRLR Antibody-Drug Conjugates Effectively Kill Cells with Low-to-Moderate PRLR Expression Levels as Well as Cells with High PRLR Expression Levels To determine the relative cell-killing potency of anti-PRLR ADCs of the invention compared to a similar anti-ErbB2 ADC, cell-killing assays were run on multiple cells lines expressing either PRLR, ErbB2 or a combination of both receptors.

PRLR-overexpressing cells, including HEK293, PC3, MCF7 and NCI-N87, were generated to assess the ability of anti-PRLR conjugated antibodies to reduce cell viability. For comparative purposes, PC3 and T47D cells with overexpressed ErbB2 were also generated, as well as an MCF7 cell line over-expressing both hPRLR and hErbB2. Briefly, Lipofectamine® 2000-mediated transfection methodology was utilized to generate HEK293 cells expressing human PRLR (HEK293/hPRLR) or human ErbB2 (HEK293/hErbB2). Lipofectamine LTX with Plus Reagent was used to generate PC3 cells expressing human PRLR (PC3/hPRLR) or human ErbB2 (PC3/hErbB2). Lentiviral-mediated transduction was utilized to generate MCF7 cells expressing human PRLR (MCF7/hPRLR), NCI-N87 cells expressing human PRLR (NCI-N87/hPRLR), T47D cells over-expressing human ErbB2 (T47D/hErbB2), and MCF7 cells expressing both human PRLR and human ErbB2 (MCF7/hPRLR/hErbB2). All lines were selected for at least two weeks in complete growth media plus appropriate selection reagents. Stably expressing populations were enriched for PRLR expression via FACS using the anti PRLR antibody Control I.

Cell surface expression of PRLR and ErbB2 was analyzed via FACS using either the Control I anti-PRLR antibody or Control II anti-HER2 antibody, respectively. Additionally, endogenous PRLR cell surface expression on the T47D #11 cell line, a variant of the T47D line selected for more aggressive in vivo tumor growth, was also determined. Approximately 1×10$^6$ cells were incubated with 10 μg/ml of anti-PRLR Control Antibody (Control I), an anti-ErbB2 control antibody (Control II), or an isotype control for 30 min on ice in antibody dilution buffer. Following two washes with antibody dilution buffer, cells were incubated with 10 μg/ml of PE conjugated anti-human secondary antibodies for 30 min on ice. Following two additional washes, samples were run on the Accuri C6 (BD) cytometer and analyzed with FlowJo software (Tree Star, Inc., Ashland, Oreg.). Relative expression level results are shown in Table 10.

TABLE 10

Human PRLR Cell Surface Expression (Engineered & Endogenous Lines)
FACS Binding (MFI FOLD ABOVE ISOTYPE CONTROL)

| Cell Line | Unstained | Secondary alone | Isotype Ctrl | Anti-PRLR (Control I) | Anti-ErbB2 (Control II) |
|---|---|---|---|---|---|
| 293 | 1X | 1X | 1X | 1X | 28X |
| 293/hErbB2 | 1X | 1X | 1X | 1X | 215X |
| 293/hPRLR | 1X | 1X | 1X | 18X | 18X |
| PC3 | 1X | 1X | 1X | 1X | 41X |
| PC3/hErbB2 | 1X | 1X | 1X | 1X | 238X |
| PC3/hPRLR | 1X | 1X | 1X | 13X | 31X |
| T47D | 1X | 1X | 1X | 12X | 87X |
| T47D#11 | 1X | 1X | 1X | 10X | ND |
| T47D/hErbB2 | 1X | 1X | 1X | 12X | 437X |
| SK-BR-3 | 1X | 1X | 1X | 1X | 600X |
| MCF7 | 1X | 1X | 1X | 3X | 42X |
| MCF7/hPRLR | 1X | 1X | 1X | 55X | 36X |
| MCF7/hPRLR/hErbB2 | 1X | 1X | 1X | 55X | 349X |
| NCI-N87 | 1X | 1X | 1X | 1X | 1,400X |
| NCI-N87/hPRLR | 1X | 1X | 1X | 6X | 1,400X |

In general, exogenous PRLR surface expression ranged from 6-fold to 55-fold over background, with most engineered cells exhibiting 12-fold to 18-fold PRLR expression over background. Endogenous PRLR expression was 3-fold over background in MCF7 cells but was not detected in parental HEK293, PC3 and NCI-N87 lines. Endogenous PRLR expression was 12-fold over background in the T47D cell line and 10-fold over background in the T47D #11 variant cell line. ErbB2 expression was detected in all PRLR-expressing cell lines, and ranged from 18-fold to 1400-fold above background.

Next, the ability of anti-PRLR-DM1 antibody-drug conjugates (i.e., anti-PRLR antibodies conjugated to DM1 via a non-cleavable linker [SMCC]) to reduce cell viability was determined using in vitro cell based assays. Cells were seeded in PDL-coated 96 well plates at 1500 to 10000 cells per well in complete growth media and allowed to grow overnight. For cell viability curves, ADCs or free DM1 (as the methyl disulfide derivative DM1-SMe) were added to the cells at final concentrations ranging from 500 nM to 5 pM and incubated for 3 days. The 293, PC3 and T47D cells were incubated with CCK8 (Dojindo, Rockville, Md.) for the final 1-3 hours and the absorbance at 450 nm ($OD_{450}$) was determined on a Flexstation3 (Molecular Devices, Sunnyvale, Calif.). MCF7 cells were treated with Hoechst 33342 nuclear stain while being fixed with 4% formaldehyde. Images were acquired on the ImageXpress micro XL (Molecular Devices, Sunnyvale, Calif.) and nuclear counts were determined via Columbus image analysis software (Perkin Elmer, Shelton, Conn.). Background $OD_{450}$ values (PC3, 293, and T47D) or nuclear counts (MCF7) from digitonin (40 nM) treated cells was subtracted from all wells and viability was expressed as a percentage of the untreated controls. $IC_{50}$ values were determined from a four-parameter logistic equation over a 10-point response curve (GraphPad Prism). $IC_{50}$ values and percent cell killing are shown in Tables 11 and 12.

TABLE 11

Cell Kill Potency of Anti-PRLR-DM1 Antibody-Drug Conjugates

| Antibody-Drug Conjugate | 293 | | 293/PRLR | | PC3 | | PC3/PRLR | |
|---|---|---|---|---|---|---|---|---|
| | $IC_{50}$ | % Kill | $IC_{50}$ | % Kill | $IC_{50}$ | % Kill | $IC_{50}$ | % Kill |
| DM1 (free drug) | 0.27 | 98 | 0.36 | 97 | 0.47 | 91 | 0.59 | 80 |
| H1H6953N-DM1 | 100 | 88 | 0.28 | 95 | 110 | 78 | 0.86 | 67 |
| H1H6958N2-DM1 | 75 | 98 | 0.10 | 95 | 150 | 83 | 0.43 | 83 |
| H1H6959N2-DM1 | 75 | 100 | 4.82 | 95 | 150 | 79 | 11.6 | 82 |
| H1H6960N-DM1 | 75 | 100 | 0.38 | 95 | 150 | 80 | 1.13 | 82 |
| H1H6975N-DM1 | 100 | 87 | ND | ND | 200 | 71 | 2.70 | 68 |
| H1H6762P-DM1 | 100 | 89 | ND | ND | 250 | 78 | 0.98 | 66 |
| H1H6765P-DM1 | 100 | 86 | ND | ND | 200 | 70 | 0.57 | 70 |
| H1H6782P-DM1 | 100 | 86 | ND | ND | 300 | 67 | 0.92 | 64 |
| H1H6793P-DM1 | 100 | 84 | ND | ND | 200 | 72 | 3.65 | 65 |
| H1H6800P-DM1 | 150 | 85 | ND | ND | 150 | 72 | 1.37 | 68 |
| H1H6803P-DM1 | 300 | 7 | ND | ND | 150 | 72 | 2.32 | 70 |
| Control I-DM1 | 100 | 92 | 0.28 | 95 | >100 | 79 | 7.28 | 80 |
| Isotype ctrl-DM1 | 100 | 60 | 100 | 93 | 125 | 78 | 110 | 63 |

$IC_{50}$ values are in nM;
ND: not determined

TABLE 12

Cell Kill Potency of Anti-PRLR-DM1
Antibody-Drug Conjugates (continued)

| Antibody-Drug Conjugate | T47D | | MCF7 | | MCF7/PRLR | |
|---|---|---|---|---|---|---|
| | $IC_{50}$ | % Kill | $IC_{50}$ | % Kill | $IC_{50}$ | % Kill |
| DM1 (free drug) | 0.45 | 86 | 1.17 | 83 | 1.47 | 88 |
| H1H6953N-DM1 | 1.64 | 79 | 100 | 55 | 0.29 | 76 |
| H1H6958N2-DM1 | 1.34 | 71 | 100 | 77 | 0.19 | 77 |
| H1H6959N2-DM1 | 48.90 | 71 | 100 | 82 | 0.47 | 80 |
| H1H6960N-DM1 | 5.10 | 71 | 100 | 77 | 0.29 | 78 |
| H1H6975N-DM1 | 6.90 | 80 | 150 | 73 | 0.49 | 87 |
| H1H6762P-DM1 | 12.60 | 80 | 110 | 64 | 0.46 | 83 |
| H1H6765P-DM1 | 1.63 | 78 | 150 | 68 | 0.18 | 84 |
| H1H6782P-DM1 | 4.19 | 74 | 120 | 57 | 0.65 | 85 |
| H1H6793P-DM1 | 11.10 | 53 | 125 | 67 | 0.54 | 87 |
| H1H6800P-DM1 | 3.20 | 79 | 150 | 65 | 0.40 | 85 |
| H1H6803P-DM1 | 8.61 | 77 | 150 | 60 | 0.44 | 84 |
| Control I-DM1 | 24.50 | 65 | 100 | 46 | 0.59 | 75 |
| Isotype ctrl-DM1 | 150 | 61 | 120 | 66 | 100 | 84 |

$IC_{50}$ values are in nM

As summarized in Tables 11 and 12, several anti-PRLR-DM1 antibody-drug conjugates potently reduced cell viability in multiple cell backgrounds, with $IC_{50}$ values as low as 100 pM. An exemplary anti-PRLR conjugated antibody, H1H6958N2-DM1, reduced the cell viability of HEK293, PC3 and MCF7-PRLR expressing cells with sub-nM $IC_{50}$s ranging from 100 pM to 460 pM, and killed endogenously expressing T47D cells with an $IC_{50}$ of 1.3 nM. The similarly conjugated anti-PRLR Control I antibody (Control I-DM1) was several fold less potent than H1H6958N2-DM1 across all cell lines. Non-binding isotype controls and unconjugated antibodies had no impact on cell viability.

Additionally, the impact of the PRLR ligand, PRL, on PRLR-SMCC-DM1 cell kill in T47D cells was assessed. T47D cells were incubated simultaneously with PRL (15 nM) and either a non-blocking anti PRLR antibody (H1H6782P) or a receptor blocking antibody (H1H6958N2). Results are summarized in Table 13.

TABLE 13

Cell Kill Potency of Anti-PRLR-DM1 Antibody-Drug
Conjugates in the Presence of PRLR Ligand (PRL)

| Treatment | HEK293 | | T47D | |
|---|---|---|---|---|
| | $IC_{50}$ (nM) | % Kill | $IC_{50}$ (nM) | % Kill |
| Me-SS-May Free DM1 | 0.6 | 94 | 0.30 | 100 |
| Isotype Control-SMCC-DM1 | 100 | 78 | 300 | 94 |
| Isotype Control-SMCC-DM1 + 15 nM PRL | 170 | 82 | 97 | 89 |
| H1H6958N2-SMCC-DM1 | 90 | 88 | 1.0 | 100 |
| H1H6958N2-SMCC-DM1 + 15 nM PRL | 110 | 86 | 3.0 | 100 |
| H1H6782P-SMCC-DM1 | 90 | 83 | 1.0 | 98 |
| H1H6782P-SMCC-DM1 + 15 nM PRL | 70 | 78 | 2.0 | 97 |

As shown in Table 13, the presence of PRL had only a modest impact on PRLR ADC-mediated cell kill with an observed 2-3 fold reduction in the cell kill potency of the tested mAbs.

The potency of anti-PRLR conjugated antibodies compared with a similarly conjugated antibody to the co-expressed ErbB2 cell surface target was also assessed. Both PRLR and ErbB2 are expressed in a majority of breast cancers, and anti-ErbB2 antibodies conjugated to DM1 have shown clinical efficacy in targeting ErbB2 (+) breast cancer (Hurvitz et al; 2013). An ErbB2 Control Antibody (Control II) conjugated to DM1 (Control II-DM1) was tested in in vitro viability assays in the cell lines generated above. Cell kill potency of conjugated anti-PRLR antibodies compared to the anti-ErbB2 conjugated antibody is summarized in Tables 14-17.

TABLE 14

Cell Kill Potency of Anti-PRLR-DM1 and
Anti-ErbB2-DM1 Antibody-Drug Conjugates

| Antibody-Drug Conjugate | 293 | | 293/ErbB2 | | 293/PRLR | |
|---|---|---|---|---|---|---|
| | $IC_{50}$ | % Kill | $IC_{50}$ | % Kill | $IC_{50}$ | % Kill |
| DM1 (free drug) | 0.5 | 95 | 0.26 | 100 | 0.82 | 95 |
| H1H6953N-DM1 (Anti PRLR-DM1) | 100 | 92 | 120 | 98 | 0.43 | 93 |
| Control II-DM1 (Anti ErbB2-DM1) | 100 | 89 | 2.0 | 98 | 100 | 88 |
| Isotype Control-DM1 | 150 | 86 | 110 | 98 | 150 | 86 |
| PRLR expression | 1X | | 1X | | 18X | |
| ErbB2 expression | 28X | | 215X | | 18X | |

$IC_{50}$ values are in nM

TABLE 15

Cell Kill Potency of Anti-PRLR-DM1 and Anti-ErbB2-DM1
Antibody-Drug Conjugates (continued)

| Antibody-Drug Conjugate | PC3 | | PC3/ErbB2 | | PC3/PRLR | |
|---|---|---|---|---|---|---|
| | $IC_{50}$ | % Kill | $IC_{50}$ | % Kill | $IC_{50}$ | % Kill |
| DM1 (free drug) | 0.44 | 88 | 0.42 | 85 | 0.24 | 82 |
| H1H6953N-DM1 (Anti PRLR-DM1) | 100 | 80 | 80 | 73 | 0.68 | 76 |
| Control II-DM1 (Anti ErbB2-DM1) | 90 | 80 | 1.1 | 80 | 100 | 62 |
| Isotype Control-DM1 | 85 | 82 | 90 | 71 | 100 | 62 |
| PRLR expression | 1X | | 1X | | 13X | |
| ErbB2 expression | 41X | | 238X | | 31X | |

$IC_{50}$ values are in nM

TABLE 16

Cell Kill Potency of Anti-PRLR-DM1 and Anti-ErbB2-DM1 Antibody-Drug Conjugates (continued)

| Antibody-Drug Conjugate | T47D $IC_{50}$ | T47D % Kill | T47D/ErbB2 $IC_{50}$ | T47D/ErbB2 % Kill | SK-BR-3 $IC_{50}$ | SK-BR-3 % Kill | MCF7 $IC_{50}$ | MCF7 % Kill |
|---|---|---|---|---|---|---|---|---|
| DM1 (free drug) | 0.21 | 80 | 0.18 | 71 | 0.39 | 74 | 0.54 | 78 |
| H1H6953N-DM1 (Anti PRLR-DM1) | 1.3 | 78 | 2.4 | 80 | 100 | 77 | 82 | 74 |
| Control II-DM1 (Anti ErbB2-DM1) | 100 | 59 | 1.18 | 81 | 0.48 | 81 | 80 | 68 |
| Isotype Control-DM1 | 100 | 62 | 120 | 75 | 110 | 76 | 100 | 65 |
| PRLR expression | 12X | | 12X | | 1X | | 3X | |
| ErbB2 expression | 87X | | 437X | | 600X | | 42X | |

$IC_{50}$ values are in nM

TABLE 17

Cell Kill Potency of Anti-PRLR-DM1 and Anti-ErbB2-DM1 Antibody-Drug Conjugates (continued)

| Antibody-Drug Conjugate | MCF7/PRLR $IC_{50}$ | MCF7/PRLR % Kill | MCF/PRLR + ErbB2 $IC_{50}$ | MCF/PRLR + ErbB2 % Kill | NCI-N87 $IC_{50}$ | NCI-N87 % Kill | NCI-N87/PRLR $IC_{50}$ | NCI-N87/PRLR % Kill |
|---|---|---|---|---|---|---|---|---|
| DM1 (free drug) | 1.85 | 79 | 0.82 | 77 | 0.84 | 95 | 1.45 | 98 |
| H1H6953N-DM1 (Anti PRLR-DM1) | 0.33 | 76 | 0.33 | 77 | 90 | 83 | 2.9 | 94 |
| Control II-DM1 (Anti ErbB2-DM1) | 100 | 56 | 0.63 | 76 | 0.22 | 95 | 0.66 | 94 |
| Isotype Control-DM1 | 150 | 61 | 100 | 70 | 90 | 85 | 85 | 88 |
| PRLR expression | 55X | | 55X | | 1X | | 6X | |
| ErbB2 expression | 36X | | 349X | | 1400X | | 1400X | |

$IC_{50}$ values are in nM

Anti-PRLR-DM1 antibodies effectively killed cells even with relatively low levels of PRLR expression. For example, H1H6953N-DM1 (anti-PRLR-DM1) inhibited the growth of T47D cells (expressing PRLR at only 12× above background) with an $IC_{50}$ of 1.3 nM and showed 78% killing. This same antibody also inhibited the growth of 293/hPRLR cells (expressing PRLR at 18× above background) with and $IC_{50}$ of 0.43 nM and showed 93% killing. Equivalent killing with the anti-ErbB2-DM1 antibody ("control II") was observed only in cells that express the target antigen at levels greater than about 200× to about 400× above background (see e.g., PC3/hErbB2, expressing ErbB2 at 238× above background and T47D/hErbB2, expressing ErbB2 at 437× above background). Therefore, these data suggest that anti-PRLR antibody-drug conjugates can effectively target and kill tumor cells with relatively low levels of PRLR expression, while anti-ErbB2 antibody drug conjugates are effective only against tumors with very high ErbB2 expression levels.

Finally, the potency of anti-PRLR antibodies conjugated to DM1 via the non-cleavable linker SMCC was compared to the cell killing potency of anti-PRLR antibodies conjugated to MMAE via the cleavable linker: mc-vc-PAB (available from Concortis, San Diego, Calif.). Cells used in this experiment were PC3, PC3/hPRLR, MCF7/ATCC and MCF7/PRLR. Results are shown in Table 18.

TABLE 18

Anti-PRLR ADC Cell Kill Potency

| | PC3 $IC_{50}$ (nM) | PC3 % Kill | PC3/hPRLR $IC_{50}$ (nM) | PC3/hPRLR % Kill | MCF7/ATCC $IC_{50}$ (nM) | MCF7/ATCC % Kill | MCF7/PRLR $IC_{50}$ (nM) | MCF7/PRLR % Kill |
|---|---|---|---|---|---|---|---|---|
| Free DM1 | 0.5 | 90 | 1.0 | 70 | 3.0 | 80 | 1.9 | 86 |
| Free MMAE | 1.4 | 90 | 1.0 | 77 | 2.4 | 83 | 1.5 | 95 |
| Isotype Control I-SMCC-DM1 | 95 | 79 | 100 | 79 | 100 | 71 | 100 | 76 |
| Isotype Control I-mc-VC-PAB-MMAE | 200 | 33 | 145 | 55 | 143 | 23 | 143 | 21 |
| H1H6953N-SMCC-DM1 | 90 | 81 | 0.4 | 83 | 80 | 70 | 0.1 | 80 |
| H1H6953N-mc-VC-PAB- | 130 | 49 | 0.2 | 80 | 150 | 42 | 0.1 | 85 |

TABLE 18-continued

Anti-PRLR ADC Cell Kill Potency

| | PC3 | | PC3/hPRLR | | MCF7/ATCC | | MCF7/PRLR | |
|---|---|---|---|---|---|---|---|---|
| | $IC_{50}$ (nM) | % Kill | $IC_{50}$ (nM) | % Kill | $IC_{50}$ (nM) | % Kill | $IC_{50}$ (nM) | % Kill |
| MMAE | | | | | | | | |
| H1H6958N2-SMCC-DM1 | 110 | 81 | 0.5 | 79 | 90 | 72 | 0.2 | 83 |
| H1H6958N2-mc-VC-PAB-MMAE | 100 | 39 | 0.5 | 82 | 150 | 53 | 0.2 | 88 |
| H1H6765P-SMCC-DM1 | 80 | 80 | 0.3 | 83 | 90 | 71 | 0.1 | 81 |
| H1H6765P-mc-VC-PAB-MMAE | 150 | 29 | 0.40 | 85 | 150 | 38 | 0.2 | 86 |

As shown in Table 18, nearly equivalent cell killing in PC3/hPRLR and MCF7/hPRLR cell lines was observed for both the non-cleavable DM1 ADCs (H1H6953-SMCC-DM1, H1H6958N2-SMCC-DM1, and H1H6765-SMCC-DM1) and for the cleavable MMAE ADCs (H1H6953-mc-vc-PAB-MMAE, H1H6958N2-mc-VC-PAB-MMAE, and H1H6765-mc-VC-PAB-MMAE).

Additional toxins (DM4, MeNHC3-May, and MMD) conjugated to anti-PRLR antibodies were also tested in T47D and MCF7/hPRLR cell lines, and results are summarized in Tables 19 (293 and T47D cell killing) and 20 (MCF7/ATCC and MCF7/PRLR cell killing). (ND=not detected).

TABLE 19

Anti-PRLR Antibody Drug Conjugates - Cell Killing Properties (293 and T47D Cell Lines)

| | | | Cell Line | | | |
|---|---|---|---|---|---|---|
| | | | 293 | | T47D | |
| Antibody | Linker | Drug | $IC_{50}$ nM | % Kill | $IC_{50}$ nM | % Kill |
| | Free | DM1 (Me-SS-May) | 1.2 | 95 | 1.5 | 100 |
| | | MMAE | 0.9 | 100 | 1 | 100 |
| | | DM4 | 0.6 | 100 | 0.5 | 100 |
| | | MMD | 0.9 | 100 | 2 | 100 |
| | | MeNHC3-May | 60 | 90 | 90 | 100 |
| Isotype Control I | SMCC | DM1 | 150 | 80 | 140 | 50 |
| | mc-VC-PAB | MMAE | 300 | 30 | 300 | 20 |
| | | MMD | 300 | 70 | 140 | 70 |
| | | MeNHC3-May | 300 | 30 | 300 | 30 |
| | SPDB | DM4 | 50 | 90 | 30 | 100 |
| H1H6953N | SMCC | DM1 | 100 | 90 | 1.5 | 100 |
| | mc-VC-PAB | MMAE | ND | ND | 1.0 | 80 |
| | | MMD | 110 | 70 | 1.0 | 90 |
| | | MeNHC3-May | 300 | 20 | 1.0 | 90 |
| H1H6958N2 | SMCC | DM1 | 100 | 90 | 2 | 100 |
| | mc-VC-PAB | MMAE | ND | ND | 1 | 90 |
| | SPDB | DM4 | ND | ND | 1 | 100 |
| H1H6975P | SMCC | DM1 | 80 | 90 | 2 | 100 |
| | mc-VC-PAB | MMD | 110 | 80 | 3 | 90 |
| H1H6782P | SMCC | DM1 | 120 | 80 | 3 | 100 |
| | mc-VC-PAB | MMD | 230 | 70 | 2 | 90 |
| | mc-VC-PAB | MeNHC3-May | 60 | 90 | 2 | 90 |
| H1H6765P | SMCC | DM1 | 85 | 100 | 1 | 90 |
| | mc-VC-PAB | MMAE | ND | ND | 1 | 90 |

TABLE 20

Anti-PRLR Antibody Drug Conjugates - Cell Killing Properties (MCF7/ATCC and MCF7/PRLR Cell Lines)

| | | | Cell Line | | | |
|---|---|---|---|---|---|---|
| | | | MCF7/ATCC | | MCF7/PRLR | |
| Antibody | Linker | Drug | $IC_{50}$ nM | % Kill | $IC_{50}$ nM | % Kill |
| | Free | DM1 (Me-SS-May) | 1.3 | 80 | 0.8 | 80 |
| | | MMAE | 2.4 | 80 | 1.5 | 95 |
| | | DM4 | 1.3 | 90 | 2 | 90 |
| | | MMD | 2 | 90 | 0.4 | 90 |
| | | MeNHC3-May | 100 | 70 | 50 | 80 |
| Isotype Control I | SMCC | DM1 | 300 | 60 | 150 | 70 |
| | mc-VC-PAB | MMAE | 140 | 20 | 140 | 20 |
| | | MMD | 300 | 40 | 70 | 75 |
| | | MeNHC3-May | 300 | 30 | 200 | 55 |
| | SPDB | DM4 | 70 | 80 | 80 | 90 |
| H1H6953N | SMCC | DM1 | 90 | 70 | 0.3 | 80 |
| | mc-VC-PAB | MMAE | 150 | 40 | 0.1 | 85 |
| | | MMD | 300 | 50 | 0.2 | 90 |
| | | MeNHC3-May | 150 | 60 | 0.2 | 80 |
| H1H6958N2 | SMCC | DM1 | 70 | 70 | 0.2 | 80 |
| | mc-VC-PAB | MMAE | 150 | 50 | 0.2 | 90 |
| | SPDB | DM4 | 25 | 80 | 0.8 | 90 |
| H1H6975P | SMCC | DM1 | 200 | 70 | 0.2 | 80 |
| | mc-VC-PAB | MMD | 150 | 50 | 0.2 | 90 |
| H1H6782P | SMCC | DM1 | 250 | 70 | 0.3 | 80 |
| | mc-VC-PAB | MMD | 200 | 50 | 0.3 | 90 |
| | mc-VC-PAB | MeNHC3-May | 250 | 50 | 0.2 | 80 |
| H1H6765P | SMCC | DM1 | 150 | 70 | 0.3 | 90 |
| | mc-VC-PAB | MMAE | 150 | 40 | 0.2 | 90 |

All tested anti PRLR ADCs, regardless of the toxin and linker utilized, specifically killed the tested cells. T47D cell viability $10_{50}5$ ranged from 0.6 nM to 3.4 nM and MCF7/hPRLR cell viability 1050s ranged from 0.2 nM to 0.8 nM.

Example 8. Anti-PRLR Antibody-Drug Conjugates Effectively Inhibit Tumor Growth In Vivo To determine the in vivo efficacy of the anti-PRLR-DM1 antibody-drug conjugates, studies were performed in immunocompromised mice bearing PRLR+ breast cancer xenografts.

Briefly, $20 \times 10^6$ MCF7/PRLR cells (ATCC HTB-22 transfected with full length hPRLR as previously described) were implanted subcutaneously into the left mammary fat pad of female NCr nude mice. In other studies, $10 \times 10^6$ PC3/PRLR (ATCC CRL-1435 transfected with full length hPRLR as previously described) were implanted subcutaneously into the left flank of male SCID mice. Additionally, $10 \times 10^6$ parental T47D (ATCC HTB-133) or $7.5 \times 10^{10}$ T47D #11 cells (ATCC HTB-133 serially passaged in vivo as described below) were subcutaneously implanted into the left flank of female CB17 SCID mice. All mice were obtained from Taconic (Hudson, N.Y.). Each bolus of cells was supplemented with a 90-day estrogen release pellet (1.7 mg/pellet; Innovative Research America, Sarasota Fla.). Once tumors had reached an average volume of 250 mm³, mice were randomized into groups of seven and dosed with anti-PRLR antibody-drug conjugates of the invention or control reagents. Control reagents included PBS vehicle, free methyl-disulfide DM1 (DM1-SMe) and isotype Control 1-DM1.

In multi-dose studies, mice were dosed once a week for a total of three weeks with tumor volumes and body weights being monitored twice weekly throughout the study. Test ADCs were dosed at 5 and/or 15 mg/kg in the multi-dose studies. In single-dose studies, mice received a single dose of test ADC, and tumor volumes and body weights were monitored twice weekly throughout the study. Test ADCs were dosed at 1, 2.5, 5, and 15 mg/kg in the single-dose studies. Average tumor size as well as tumor growth inhibition relative to the vehicle treated group were calculated for each group. Tumors were measured with calipers twice a week until the average size of the vehicle group reached 1000 mm³. Tumor size was calculated using the formula (length×width²)/2. Tumor growth inhibition was calculated according to the following formula: $(1-((T_{final}-T_{initial})/(C_{final}-C_{initial})))*100$, where T (treated group) and C (control group) represent the mean tumor mass on the day the vehicle group reached 1000 mm³. Animals were observed to Day 52. Results are summarized in Tables 21-25 (multi-dose) and Table 26 (single dose). (NT=not tested in the particular experiment shown).

TABLE 21

Tumor Size and Tumor Growth Inhibition Following Multi-Dose Administration of Anti-PRLR Antibody-Drug Conjugates and Controls - MCF7/PRLR tumors (TRIAL #1)
[NCr Nude mice - data collected at Day 52]

| Treatment Group | Dose (mg/kg) | Final Tumor size mm³ (mean ± SEM) | Average Tumor Growth Inhibition (%) |
|---|---|---|---|
| Vehicle | — | 1068 ± 384 | — |
| Free DM1 | 0.2 | 625 ± 141 | 57 |
| Isotype control Ab-DM1 | 5 | NT | NT |
|  | 15 | 300 ± 141 | 96 |
| H1H6958N2 | 15 | 483 ± 46 | 74 |
| H1H6958N2-DM1 | 5 | 51 ± 33 | 128 |
|  | 15 | 0 ± 0 | 133 |
| H1H6953N | 15 | 421 ± 23 | 79 |
| H1H6953N-DM1 | 5 | 107 ± 45 | 120 |
|  | 15 | 0 ± 0 | 133 |
| H1H6975N | 15 | 659 ± 144 | 51 |
| H1H6975N-DM1 | 5 | 125 ± 46 | 118 |
|  | 15 | 0 ± 0 | 135 |
| H1H6782P | 15 | NT | NT |
| H1H6782P-DM1 | 5 |  |  |
|  | 15 |  |  |
| H1H6765P | 15 | NT | NT |
| H1H6765P-DM1 | 5 |  |  |
|  | 15 |  |  |

TABLE 22

Tumor Size and Tumor Growth Inhibition Following Multi-Dose Administration of Anti-PRLR Antibody-Drug Conjugates and Controls - MCF7/PRLR tumors (TRIAL #2)
[NCr Nude mice - data collected at Day 63]

| Treatment Group | Dose (mg/kg) | Final Tumor size mm³ (mean ± SEM) | Average Tumor Growth Inhibition (%) |
|---|---|---|---|
| Vehicle | — | 870 ± 211 | — |
| Free DM1 | 0.2 | 1080 ± 451 | −33 |
| Isotype control Ab-DM1 | 5 | 1106 ± 371 | −39 |
|  | 15 | 712 ± 214 | 24 |
| H1H6958N2 | 15 | 766 ± 128 | 17 |
| H1H6958N2-DM1 | 5 | 117 ± 10 | 116 |
|  | 15 | 0 ± 0 | 137 |
| H1H6953N | 15 | NT | NT |
| H1H6953N-DM1 | 5 |  |  |
|  | 15 |  |  |
| H1H6975N | 15 | NT | NT |
| H1H6975N-DM1 | 5 |  |  |
|  | 15 |  |  |
| H1H6782P | 15 | 300 ± 83 | 88 |
| H1H6782P-DM1 | 5 | 74 ± 34 | 123 |
|  | 15 | 0 ± 0 | 137 |
| H1H6765P | 15 | 737 ± 182 | 19 |
| H1H6765P-DM1 | 5 | 90 ± 56 | 122 |
|  | 15 | 0 ± 0 | 136 |

TABLE 23

Tumor Size and Tumor Growth Inhibition Following Multi-Dose Administration of Anti-PRLR Antibody-Drug Conjugates and Controls - PC3/PRLR tumors (TRIAL #1)
[SCID mice - data collected at Day 63]

| Treatment Group | Dose (mg/kg) | Final Tumor size mm³ (mean ± SEM) | Average Tumor Growth Inhibition (%) |
|---|---|---|---|
| Vehicle | — | 1311 ± 257 | — |
| Free DM1 | 0.2 | 1361 ± 120 | −5 |
| Isotype control Ab-DM1 | 5 | 1379 ± 128 | −7 |
|  | 15 | 1091 ± 93 | 19 |
| H1H6958N2 | 15 | 1507 ± 106 | −19 |
| H1H6958N2-DM1 | 5 | 1247 ± 171 | 5 |
|  | 15 | 808 ± 83 | 46 |
| H1H6953N | 15 | 1306 ± 127 | 0 |
| H1H6953N-DM1 | 5 | 1058 ± 138 | 23 |
|  | 15 | 892 ± 53 | 39 |
| H1H6975N | 15 | 1185 ± 97 | 12 |
| H1H6975N-DM1 | 5 | 973 ± 169 | 31 |
|  | 15 | 895 ± 63 | 38 |
| H1H6782P | 15 | NT | NT |
| H1H6782P-DM1 | 5 |  |  |
|  | 15 |  |  |
| H1H6765P | 15 | NT | NT |
| H1H6765P-DM1 | 5 |  |  |
|  | 15 |  |  |

TABLE 24

Tumor Size and Tumor Growth Inhibition Following Multi-Dose Administration of Anti-PRLR Antibody-Drug Conjugates and Controls - PC3/PRLR tumors (TRIAL #2)
[SCID mice - data collected at Day 55]

| Treatment Group | Dose (mg/kg) | Final Tumor size mm³ (mean ± SEM) | Average Tumor Growth Inhibition (%) |
|---|---|---|---|
| Vehicle | — | 1222 ± 99 | 0 |
| Free DM1 | 0.2 | 1147 ± 59 | 7 |
| Isotype control Ab-DM1 | 5 | 1052 ± 101 | 16 |
|  | 15 | 1049 ± 127 | 16 |

TABLE 24-continued

Tumor Size and Tumor Growth Inhibition Following Multi-Dose
Administration of Anti-PRLR Antibody-Drug Conjugates and
Controls - PC3/PRLR tumors (TRIAL #2)
[SCID mice - data collected at Day 55]

| Treatment Group | Dose (mg/kg) | Final Tumor size mm³ (mean ± SEM) | Average Tumor Growth Inhibition (%) |
|---|---|---|---|
| H1H6958N2 | 15 | 917 ± 253 | 28 |
| H1H6958N2-DM1 | 5 | 566 ± 63 | 61 |
|  | 15 | 230 ± 22 | 94 |
| H1H6953N | 15 | NT | NT |
| H1H6953N-DM1 | 5 |  |  |
|  | 15 |  |  |
| H1H6975N | 15 | NT | NT |
| H1H6975N-DM1 | 5 |  |  |
|  | 15 |  |  |
| H1H6782P | 15 | 1154 ± 212 | 6 |
| H1H6782P-DM1 | 5 | 490 ± 63 | 69 |
|  | 15 | 321 ± 33 | 85 |
| H1H6765P | 15 | 1208 ± 72 | 1 |
| H1H6765P-DM1 | 5 | 489 ± 70 | 70 |
|  | 15 | 181 ± 42 | 98 |

TABLE 25

Tumor Size and Tumor Growth Inhibition Following Multi-Dose
Administration of Anti-PRLR Antibody-Drug Conjugates and
Controls - T47D#11 tumors
[SCID mice - data collected at Day 66]

| Treatment Group | Dose (mg/kg) | Final Tumor size mm³ (mean ± SEM) | Average Tumor Growth Inhibition (%) |
|---|---|---|---|
| Vehicle | — | 1234 ± 88 | 0 |
| Free DM1 | 0.2 | 1433 ± 23 | −19 |
| Isotype control Ab-DM1 | 5 | 1340 ± 176 | −9 |
|  | 15 | 1678 ± 67 | −42 |
| H1H6958N2 | 15 | 1259 ± 122 | −3 |
| H1H6958N2-DM1 | 5 | 168 ± 19 | 102 |
|  | 15 | 44 ± 5 | 112 |
| H1H6953N | 15 | NT | NT |
| H1H6953N-DM1 | 5 |  |  |
|  | 15 |  |  |
| H1H6975N | 15 | NT | NT |
| H1H6975N-DM1 | 5 |  |  |
|  | 15 |  |  |
| H1H6782P | 15 | 1537 ± 111 | −29 |
| H1H6782P-DM1 | 5 | 293 ± 20 | 90 |
|  | 15 | 124 ± 36 | 106 |
| H1H6765P | 15 | 1278 ± 164 | −3 |
| H1H6765P-DM1 | 5 | 183 ± 28 | 100 |
|  | 15 | 69 ± 12 | 111 |

TABLE 26

Tumor Size and Tumor Growth Inhibition Following Single Dose
Administration of Anti-PRLR Antibody-Drug Conjugates and
Controls - MCF7/PRLR tumors
[data collected at Day 55]

| Treatment Group | Dose (mg/kg) | Final Tumor size mm³ (mean ± SEM) | Average Tumor Growth Inhibition (%) |
|---|---|---|---|
| Vehicle | — | 710 ± 249 | 0 |
| Isotype Control Ab-DM1 | 15 | 514 ± 86 | 38 |
| H1H6958N2 | 15 | 703 ± 160 | 1 |
| H1H6958N2-1 | 1 | 274 ± 142 | 86 |
| H1H6958N2-1 | 2.5 | 172 ± 53 | 109 |
| H1H6958N2-1 | 5 | 107 ± 26 | 120 |
| H1H6958N2-1 | 15 | 33 ± 23 | 136 |

Discussion

In this example, five exemplary anti-PRLR antibodies conjugated to DM1 were initially assessed for the ability to reduce MCF7/PRLR and PC3/PRLR tumor volume in multi-dose studies. In the first multi-dose trial (Table 21), H1H6958N2-DM1, H1H6953N-DM1 and H1H6975N-DM1 antibodies potently inhibited MCF7/PRLR tumor growth at both 5 and 15 mg/kg doses. At the highest dose, all three DM1 conjugated antibodies reduced tumors to undetectable levels, with a percent reduction in tumor volume of about 133-135%. This finding was replicated in a second multi-dose trial (Table 22) when H1H6958N2-DM1 was tested alongside two additional exemplary anti-PRLR antibodies conjugated to DM1: H1H6782P and H1H6765P. In this second trial, tumor growth was also reduced to undetectable levels at the highest dose of 15 mg/kg, with percent reduction in tumor volume of 136-137%. Although treatment with unconjugated anti-PRLR antibodies resulted in moderate reduction of tumor volume (17-79%) compared to the vehicle group, the greatest inhibition in tumor size was observed in cohorts treated with antibody-drug conjugates.

Next, the anti-tumor efficacy of these same exemplary anti-PRLR-DM1 antibodies was assessed in multi-dose studies in mice bearing PRLR positive PC3/PRLR xenografts. (Tables 23 and 24). Mice were treated after tumors had grown for 21 days. H1H6958N2-DM1, H1H6953N-DM1 and H1H6975N-DM1 all demonstrated inhibition of tumor growth, especially at the highest dose of 15 mg/kg. (Table 23). Anti-tumor effect was similarly observed in a second trial, when H1H6958N2-DM1 was tested alongside H1H6765P-DM1 and H1H6782P-DM1 after 15 days of tumor growth. At the highest dose administered, tumor inhibition across trials ranged from 38-98%. (Table 24). In comparison, an Isotype-control conjugated to DM1 produced only 16% tumor inhibition with final tumor volumes not significantly different to vehicle controls.

A further assessment of the anti-PRLR ADCs repeatedly dosed at 5 and 15 mg/kg was performed in mice bearing T47D #11 xenografts endogenously expressing PRLR. (Table 25). As in other tumor models, dosing was initiated when tumor size averaged 200 mm³. Results obtained in this tumor model were consistent with earlier results and clearly demonstrated the anti-tumor activity of the anti-PRLR antibodies conjugated to DM1. For example, H1H6958N2-DM1, H1H6765P-DM1 and H1H6782P-DM1 ADCs potently inhibited tumor growth at both the 5 and 15 mg/kg dose. At 5 mg/kg anti-PRLR-DM1 conjugated antibodies exhibited 89-100% tumor inhibition whereas at 15 mg/kg DM1-conjugated antibodies resulted in 106-112% tumor growth inhibition. Importantly, unconjugated anti-PRLR antibodies were not observed to have any anti-tumor efficacy in this endogenous tumor model, indicating the role of the DM1 conjugate in producing anti-tumor efficacy. Again, efficacy of anti-PRLR ADC was very specific as control ADC failed to have any effect on tumor growth.

In a final example, anti-PRLR DM1-conjugated antibody H1H6958N2 was assessed in MCF7/PRLR xenografted mice in a single-dose study. (Table 26). As in multiple-dose studies, established tumors were allowed to grow to approximately 200 mm³ before a single dose was administered. Here, H1H6958N2-DM1 was given at 1, 2.5, 5 and 15 mg/kg. As summarized in Table 26, a dose dependent anti-tumor effect was seen across the wide range used in this study. Anti-tumor effect was observed at all doses, with 1 mg/kg causing a significant decrease in tumor volume relative to vehicle control tumors. Further, although 15 mg/kg of Isotype Control I-DM1 had some anti-tumor effect (~38% tumor growth inhibition), doses of anti-PRLR-DM1 at 2.5 mg/kg and higher significantly reduced tumor volume (>100% tumor growth inhibition at all doses above 1 mg/kg tested). Single doses of 5 and 15 mg/kg demonstrated anti-tumor efficacy comparable to that observed following repeat dosing at the same level, illustrating the potency of the anti-PRLR ADCs.

In summary, this example illustrates that conjugated anti-PRLR antibodies of the invention are potent inhibitors of tumor growth and are able to reduce tumor size to undetectable levels in the various tumor models tested.

Example 9. Antibody-Drug Conjugates Against Class-I Cytokine Receptors Effectively Kill Cell Lines Expressing Low Levels of Target Antigen As discussed elsewhere herein, antibody-drug conjugates against PRLR effectively kill PRLR-expressing cell lines, even those that express relatively low levels of target antigen. As previously noted, PRLR belongs to the class I cytokine receptor family, which includes IL-4R and IL-6R. Similar to PRLR, IL-4R and IL-6R are single-pass transmembrane receptors; IL-4R mediates IL-4 and IL-13 signaling, while IL-6R mediates IL-6 signaling via a co-complex with the gp130 receptor. In further support of the general concept that ADCs directed against class I cytokine receptors may be used to effectively kill cells, including cells that express low-levels of target antigen, the cell-killing ability of ADCs directed against IL-4R and IL-6R was evaluated.

Cell surface antigen levels on cells that endogenously or recombinantly express IL-4R or IL-6R were first established using FACS. Briefly, approximately 1 million KG-1 (IL-4R*), HEK293/IL-4R and Ramos (IL-6R*) cells were incubated with exemplary anti-IL-4R (H4H083P2, see U.S. Pat. No. 7,608,693) and anti-IL-6R (VV6A9-5, see U.S. Pat. No. 7,582,298) antibodies for 30 min on ice. After washing, a PE-conjugated anti-human secondary antibody (10 μg/ml) was added for 30 min followed by a second washing step and subsequent analysis on an Accuri C6 cytometer using FlowJo software (Tree Star, Inc., Ashland, Oreg.). Relative IL-4R and IL-6R cell surface expression levels were calculated as the mean fluorescence intensity (MFI) above isotype control levels. Expression levels are summarized in Table 27.

TABLE 27

Relative IL-4R and IL-6R Cell Surface Expression on IL-4R and IL-6R Endogenously or Recombinantly Expressing Cell Lines

| Receptor Expression | Cell Line Expression Level; Fold Over Background | | | |
|---|---|---|---|---|
| | HEK293 | HEK293/ IL4R | KG-1 | Ramos |
| IL-4R | 2 | 50 | 1 | 4 |
| IL-6R | 1 | 1 | 7 | 1 |

As shown in Table 27, HEK293 and Ramos cells endogenously expressed IL-4R at levels 2-fold and 4-fold over background, respectively, while the engineered HEK293/IL-4R cell line expressed IL-4R at levels 50-fold above background. IL-4R expression was undetectable over background on KG-1 cells. IL-6R expression was detected at 7-fold above background levels in KG-1 cells, and not on HEK293 or Ramos cell lines.

Next, exemplary anti-IL-4R (H4H083P2) and anti-IL-6R (VV6A9-5) antibodies were conjugated to the cytotoxic drug DM1 and their potency in cytotoxicity assays was evaluated. Briefly, HEK293/IL-4R, Ramos or KG-1 cell lines, as well as HEK293 parental cells were seeded in PDL-coated 96-well plates at 1500 to 10,000 cells per well. ADCs or free DM1 (as the methyl disulfide derivative DM1-SMe) were added to the cells at final concentrations ranging from 300 nM to 15 pM and incubated for 3 days. Cells were incubated with CCK8 (Dojindo, Rockville, Md.) for the final 1-3 hours and the absorbance at 450 nm (OD450) was determined on a Flexstation3 (Molecular Devices, Sunnyvale, Calif.). Background $OD_{450}$ values from digitonin (40 nM) treated cells were subtracted from all wells and viability was expressed as a percentage of the untreated controls. $IC_{50}$ values were determined from a four-parameter logistic equation over a 10-point response curve (GraphPad Prism). Results are presented in Table 28.

TABLE 28

Cell killing Properties of Anti-IL4R and Anti-IL6R Antibody Drug Conjugates on IL4R and IL-6R-Expressing Cell Lines

| Antibody-Drug Conjugate | HEK293 | | HEK293/ hIL4R | | KG-1 | | Ramos | |
|---|---|---|---|---|---|---|---|---|
| | $IC_{50}$ (nM) | % Kill | $IC_{50}$ (nM) | % Kill | $IC_{50}$ (nM) | % Kill | $IC_{50}$ (nM) | % Kill |
| DM1 (Free Drug) | 0.27 | 100 | 0.33 | 98 | 1.26 | 89 | 0.34 | 100 |
| Isotype control-DM1 | 70 | 89 | 110 | 91 | 100 | 74 | 60 | 91 |
| Anti-IL-4R-DM1 | 80 | 91 | 0.22 | 95 | 90 | 83 | 18 | 91 |
| Anti-IL-6R-DM1 | 100 | 88 | 70 | 92 | 38 | 77 | 70 | 94 |
| Receptor Expression Levels: Fold over Isotype Ctrl | | | | | | | | |
| IL-4R | 2 | | 50 | | 1 | | 4 | |
| IL-6R | 1 | | 1 | | 7 | | 1 | |

As shown in Table 28, anti-IL-4R-DM1 antibody-drug conjugates reduced Ramos cell viability with an $IC_{50}$ value of 18 nM despite an IL-4R surface expression of only 4-fold above background levels. IL-4R-DM1 ADCs reduced high IL-4R-expressing HEK293/IL-4R viability with an $IC_{50}$ of 0.22 nM. Anti-IL-6R-DM1 antibody-drug conjugates had a modest but reproducible impact on the viability of KG-1 cells (expressing IL-6R at a level of 7-fold above background) with an $IC_{50}$ value of 38 nM compared to an $IC_{50}$ value of 100 nM by an equivalently conjugated isotype control ADC.

In summary, this Example demonstrates that anti-IL-4R and anti-IL-6R antibody drug conjugates exhibited potent and reproducible cytotoxicity even on cell lines expressing modest receptor levels. This result is similar to what was observed with anti-PRLR ADCs where potent cell killing was obtained even on cells expressing low levels of PRLR (see, e.g., Example 7 herein). Thus, this Example provides further support for the inventive concept that anti-class I cytokine receptor ADCs in general may be effective therapeutic agents against cell lines and tumors that express class I cytokine receptors even at low levels.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An antibody-drug conjugate (ADC) according to the formula:

[Chemical structure showing Ab—L—S linked to a maytansinoid-like drug with OCH₃, OH, CH₃, Cl, and other functional groups]

wherein L is an optional linker, and Ab is an antibody or antigen-binding fragment thereof that binds to cell surface-expressed prolactin receptor (PRLR) and blocks prolactin-mediated signaling in cells expressing human PRLR, wherein the antibody or antigen-binding fragment thereof blocks prolactin-mediated signalling in cells expressing human PRLR with an $IC_{50}$ of between 100 pM and 1.3 nM.

2. The ADC of claim 1, wherein the antibody or antigen-binding fragment thereof blocks prolactin-mediated signaling in cells expressing human PRLR with an $IC_{50}$ of less than about 0.6 nM.

3. The ADC of claim 1, according to the formula:

[Chemical structure similar to above]

4. The ADC of claim 1, wherein the linker L is present.
5. The ADC of claim 3, wherein the linker L is present.
6. The ADC of claim 4, wherein the linker L is cleavable.
7. The ADC of claim 4, wherein the linker L is non-cleavable.
8. The ADC of claim 1, wherein the ADC kills cells that express PRLR at an expression level of less than 30-fold above background.
9. The ADC of claim 8, wherein the ADC kills cells that express PRLR at an expression level of less than 20-fold above background.
10. The ADC of claim 9, wherein the ADC kills cells that express PRLR at an expression level greater than 12-fold above background but less than 30-fold above background.
11. The ADC of claim 1, wherein the antibody or antigen-binding fragment thereof competes for binding to PRLR with a reference antibody comprising an HCVR/LCVR amino acid sequence pair selected from the group consisting of SEQ ID NOs: 18/26; 66/74; 274/282; 290/298; and 370/378.

12. The ADC of claim 1, wherein the antibody or antigen-binding fragment thereof binds to the same epitope on PRLR as a reference antibody comprising an HCVR/LCVR amino acid sequence pair selected from the group consisting of SEQ ID NOs: 18/26; 66/74; 274/282; 290/298; and 370/378.

13. The ADC of claim 1, wherein the antibody or antigen-binding fragment thereof comprises a heavy chain complementarity determining region (HCDR)-1 comprising SEQ ID NO:292; an HCDR2 comprising SEQ ID NO:294; an HCDR3 comprising SEQ ID NO:296; a light chain complementarity determining region (LCDR)-1 comprising SEQ ID NO:300; an LCDR2 comprising SEQ ID NO:302; and an LCDR3 comprising SEQ ID NO:304.

14. The ADC of claim 13, wherein the antibody or antigen-binding fragment thereof comprises a heavy chain variable region (HCVR) comprising SEQ ID NO:290 and a light chain variable region (LCVR) comprising SEQ ID NO:298.

15. A pharmaceutical composition comprising the ADC of claim 1 and a pharmaceutically acceptable carrier or excipient.

16. A method for killing cells that express low levels of PRLR, the method comprising contacting the cells with an antibody-drug conjugate (ADC) according to claim 1.

17. The method of claim 16, wherein the cells are tumor cells.

18. The method of claim 17, wherein the tumor cells express less than 1 million copies of PRLR per cell.

19. The method of claim 18, wherein the tumor cells express between 10,000 and 500,000 copies of PRLR per cell.

20. The method of claim 16, wherein the linker is present and cleavable.

21. The method of claim 16, wherein the linker is present and non-cleavable.

22. The method of claim 16, wherein the anti-PRLR antibody binds to cell surface-expressed prolactin receptor (PRLR) and blocks prolactin-mediated signaling in cells expressing PRLR.

23. The method of claim 16, wherein the anti-PRLR antibody competes for binding to PRLR with a reference antibody comprising an HCVR/LCVR amino acid sequence pair selected from the group consisting of SEQ ID NOs: 18/26; 66/74; 274/282; 290/298; and 370/378.

24. The method of claim 16, wherein the anti-PRLR antibody binds to the same epitope on PRLR as a reference antibody comprising an HCVR/LCVR amino acid sequence pair selected from the group consisting of SEQ ID NOs: 18/26; 66/74; 274/282; 290/298; and 370/378.

25. The method of claim 16, wherein the antibody or antigen-binding fragment thereof comprises a heavy chain complementarity determining region (HCDR)-1 comprising SEQ ID NO:292; an HCDR2 comprising SEQ ID NO:294; an HCDR3 comprising SEQ ID NO:296; a light chain complementarity determining region (LCDR)-1 comprising SEQ ID NO:300; an LCDR2 comprising SEQ ID NO:302; and an LCDR3 comprising SEQ ID NO:304.

26. The method of claim 16, wherein the antibody or antigen-binding fragment thereof comprises a heavy chain variable region (HCVR) comprising SEQ ID NO:290 and a light chain variable region (LCVR) comprising SEQ ID NO:298.

* * * * *

SEQUENCE LISTING

<160> NUMBER OF SEQ ID NOS: 404

<210> SEQ ID NO 1
<211> LENGTH: 354
<212> TYPE: DNA
<213> ORGANISM: Artificial Sequence
<220> FEATURE:
<223> OTHER INFORMATION: Synthetic

<400> SEQUENCE: 1

```
caggtgcagc tggtggagtc tgggggaggc gtggtccagc ctggggaggtc cctgagactc      60 tcctgtgcag cctctggatt caccttcagt cactatggca tggtctgggt ccgccagcct     120
ccaggcaagg ggctggagtg ggtggcactt atatcatttg atggaactac taaatactat     180
gcagactccg tgaagggccg attcaccatc tccagagaca attccaagaa cacgctatat     240
ctgcaaatga acagcctgag agctgaggac acggctgtgt atttctgtgt tggggctatt     300
gcagcagctg ccttcgatct ctggggccgt ggcaccctgg tcactgtctc ctca           354
```

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met Val Trp Val Arg Gln Pro Pro Gly Lys Gly Leu Glu Trp Val
        35                  40                  45

Ala Leu Ile Ser Phe Asp Gly Thr Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Val Gly Ala Ile Ala Ala Ala Phe Asp Leu Trp Gly Arg Gly Thr
            100                 105                 110

Leu Val Thr Val Ser Ser
        115
```

<210> SEQ ID NO 3

```
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagtcacta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser His Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatcatttg atggaactac taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Phe Asp Gly Thr Thr Lys
1               5

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
gttggggcta ttgcagcagc tgccttcgat ctc                                33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Val Gly Ala Ile Ala Ala Ala Ala Phe Asp Leu
1               5                   10

<210> SEQ ID NO 9
<211> LENGTH: 324
<212> TYPE: DNA
<213> ORGANISM: Artificial Sequence
<220> FEATURE:
```

<223> OTHER INFORMATION: Synthetic

<400> SEQUENCE: 9

```
gaaatagtga tgacgcagtc tccagccacc ctgtctgtgt ctccagggga aagagccacc      60
ctctcctgca gggccagtca gagtgttagc agcgacttag cctggtacca gcagaaacct     120
ggccaggctc ccaggctcct catctatagt gcatccgcca gggccactgg tatcccagcc     180
aggttcactg gcagtgggtc tgggacagac ttcactctca ccatcagcag cctgcagtct     240
gaagattttg cagtttatta ctgtcagcag tataataact ggcccatgta cacttttggc     300
caggggacca agctggagat caaa                                             324
```

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Ser Ala Ser Ala Arg Ala Thr Gly Ile Pro Ala Arg Phe Thr Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Met
                85                  90                  95

Tyr Thr Phe Gly Gln Gly Thr Lys Leu Glu Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagagtgtta gcagcgac                                                    18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Asp
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

```
<400> SEQUENCE: 13 agtgcatcc                                                                  9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ser Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cagcagtata ataactggcc catgtacact                                           30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Asn Trp Pro Met Tyr Thr
1               5                   10

<210> SEQ ID NO 17
<211> LENGTH: 363
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggtggt gtggtccggc ctgggggggtc cctgagactc         60 tcctgtgtag gttctggatt cagcttcgat gatcatggca tgaactgggt ccgccaaggt        120
ccagggaagg gactggagtg ggtctctggt tttaattgga atggtggtag tacaaattat        180
gcagaatctg tgaagggccg attcaccatc tccagagaca acgccaggaa ctccctgttt        240
ctgcaaatga acagtctgag agccgaggac acggccttat attactgtgt gagaggtcgc        300
agtggctggt tcaatgatgc ttttgatgtc tggggcccag gaacaatggt caccgtctct        360
tca                                                                      363

<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Val Val Arg Pro Gly Gly
1               5                   10                  15
```

```
Ser Leu Arg Leu Ser Cys Val Gly Ser Gly Phe Ser Phe Asp Asp His
         20                  25                  30

Gly Met Asn Trp Val Arg Gln Gly Pro Gly Lys Gly Leu Glu Trp Val
         35                  40                  45

Ser Gly Phe Asn Trp Asn Gly Gly Ser Thr Asn Tyr Ala Glu Ser Val
         50                  55                  60

Lys Gly Arg Phe Thr Ile Ser Arg Asp Asn Ala Arg Asn Ser Leu Phe
65                  70                  75                  80

Leu Gln Met Asn Ser Leu Arg Ala Glu Asp Thr Ala Leu Tyr Tyr Cys
                 85                  90                  95

Val Arg Gly Arg Ser Gly Trp Phe Asn Asp Ala Phe Asp Val Trp Gly
            100                 105                 110

Pro Gly Thr Met Val Thr Val Ser Ser
            115                 120

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcagct tcgatgatca tggc                                        24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Ser Phe Asp Asp His Gly
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
tttaattgga atggtggtag taca                                        24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Phe Asn Trp Asn Gly Gly Ser Thr
1               5

<210> SEQ ID NO 23
<211> LENGTH: 42
<212> TYPE: DNA
<213> ORGANISM: Artificial Sequence
<220> FEATURE:
<223> OTHER INFORMATION: Synthetic
```

<400> SEQUENCE: 23
gtgagaggtc gcagtggctg gttcaatgat gcttttgatg tc            42

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Val Arg Gly Arg Ser Gly Trp Phe Asn Asp Ala Phe Asp Val
1               5                   10

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gaaattgtgt tgacgcagtc tccaggcacc ctgtctttgt ctccagggga aagagccacc      60
ctctcctgca gggccagtca gactattaac agcaactact tagcctggta ccgacagaaa     120
cctggccaga ctcccaggct cctcatctat ggtacatcca gtagggccac tggcatccca     180
gacaggttca gtggcagtgg gtctgggaca gacttctctc tcaccatcag cagactggag     240
cctgaagatt ttgcagtgtt ttactgtcag cagtatgctg gtttacccac tttcggccct     300
gggaccaaag tggatatcaa a                                               321

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Asn Ser Asn
            20                  25                  30

Tyr Leu Ala Trp Tyr Arg Gln Lys Pro Gly Gln Thr Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Phe Tyr Cys Gln Gln Tyr Ala Gly Leu Pro
                85                  90                  95

Thr Phe Gly Pro Gly Thr Lys Val Asp Ile Lys
            100                 105

<210> SEQ ID NO 27
<211> LENGTH: 21
<212> TYPE: DNA
<213> ORGANISM: Artificial Sequence
<220> FEATURE:
<223> OTHER INFORMATION: Synthetic

```
<400> SEQUENCE: 27
cagactatta acagcaacta c                                              21

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Gln Thr Ile Asn Ser Asn Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ggtacatcc                                                             9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Gly Thr Ser
1

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
cagcagtatg ctggtttacc cact                                           24

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Gln Gln Tyr Ala Gly Leu Pro Thr
1               5

<210> SEQ ID NO 33
<211> LENGTH: 348
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggcccagc cggggggtc cctgagactc     60
```
tcctgtgtag cctctggatt cacctttagt acctattgga tgagttgggt ccgccaggct    120
ccagggaagg gactggactg ggtgggcaac ataaagcaag atggaagtga acaaaactat    180
gtggactctg tgaggggccg attcaccatc tccagagaca atgccaagaa ctcgctgttt    240
ctgcaaatga acagtctgcg agccgaggac acgggtgtgt attactgtgc gactcttctg    300
actaagggtg actactgggg ccagggaacc ctggtcaccg tctcctca                 348

<210> SEQ ID NO 34
<211> LENGTH: 116
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Ala Gln Pro Gly Gly
1               5                   10                  15

Ser Leu Arg Leu Ser Cys Val Ala Ser Gly Phe Thr Phe Ser Thr Tyr
            20                  25                  30

Trp Met Ser Trp Val Arg Gln Ala Pro Gly Lys Gly Leu Asp Trp Val
        35                  40                  45

Gly Asn Ile Lys Gln Asp Gly Ser Glu Gln Asn Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Gly Val Tyr Tyr Cys
                85                  90                  95

Ala Thr Leu Leu Thr Lys Gly Asp Tyr Trp Gly Gln Gly Thr Leu Val
            100                 105                 110

Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct ttagtaccta ttgg                                           24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Thr Tyr Trp
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
ataaagcaag atggaagtga acaa                                                    24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Lys Gln Asp Gly Ser Glu Gln
1               5

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
gcgactcttc tgactaaggg tgactac                                                 27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Ala Thr Leu Leu Thr Lys Gly Asp Tyr
1               5

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcctca ctgtctgcat ctgtgggaga cagcgtcacc            60
atcacttgtc gggcgagtca ggacattagt aattatttag actggtttca gcagaaacca           120
gggaaagccc ctaagtccct gatctatgct gcatccattt tgcaaggtgg ggtcccatca           180
aggttcagcg gcagtggata tgggacagat tcactctca ccatcagcag cctgcagcct            240
gaagattttg caacttatta ctgccgacag tataagactt acccattcac tttcggccct           300
gggaccaaag tggatatcaa a                                                     321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Asp Ile Ser Asn Tyr
            20                  25                  30

Leu Asp Trp Phe Gln Gln Lys Pro Gly Lys Ala Pro Lys Ser Leu Ile

```
                35                  40                  45
Tyr Ala Ala Ser Ile Leu Gln Gly Gly Val Pro Ser Arg Phe Ser Gly
     50                  55                  60

Ser Gly Tyr Gly Thr Asp Phe Thr Leu Thr Ile Ser Ser Leu Gln Pro
 65                  70                  75                  80

Glu Asp Phe Ala Thr Tyr Tyr Cys Arg Gln Tyr Lys Thr Tyr Pro Phe
                 85                  90                  95

Thr Phe Gly Pro Gly Thr Lys Val Asp Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
caggacatta gtaattat                                                       18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Asp Ile Ser Asn Tyr
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                                  9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cgacagtata agacttaccc attcact                                             27

<210> SEQ ID NO 48
<211> LENGTH: 9
```

<212> TYPE: PRT
<213> ORGANISM: Artificial Sequence
<220> FEATURE:
<223> OTHER INFORMATION: Synthetic

<400> SEQUENCE: 48

Arg Gln Tyr Lys Thr Tyr Pro Phe Thr
1               5

<210> SEQ ID NO 49
<211> LENGTH: 354
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggagac ttggtacagc ctggagagtc cctgagactc    60
tcctgtacag cctctggatt caccttcaat agttatgaaa tgaactgggt ccgccaggct   120
ccagggaagg gactggagtg gtctctatat attagtagta gtggtggtac caaatactac   180
gtagactctg tgaagggccg attcaccatt tccagagaca acgccaagaa gtcactgtat   240
ctgcaaatga acagcctgag agccgatgac acggctcttt attactgtgc gagactcaat   300
ggggttgatg ttttgatat ctggggccaa gggacaatgg tcaccgtctc ttca          354

<210> SEQ ID NO 50
<211> LENGTH: 118
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Asp Leu Val Gln Pro Gly Glu
1               5                   10                  15

Ser Leu Arg Leu Ser Cys Thr Ala Ser Gly Phe Thr Phe Asn Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Gly Thr Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Asp Asp Thr Ala Leu Tyr Tyr Cys
                85                  90                  95

Ala Arg Leu Asn Gly Val Asp Val Phe Asp Ile Trp Gly Gln Gly Thr
            100                 105                 110

Met Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcaatagtta tgaa                                            24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Asn Ser Tyr Glu
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtagta gtggtggtac caaa                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Ser Gly Gly Thr Lys
1               5

<210> SEQ ID NO 55
<211> LENGTH: 33
<212> TYPE: DNA
<213> ORGANISM: Artificial Sequence
<220> FEATURE:
<223> OTHER INFORMATION: Synthetic

<400> SEQUENCE: 55
gcgagactca atggggttga tgtttttgat atc                                33

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Ala Arg Leu Asn Gly Val Asp Val Phe Asp Ile
1               5                   10

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctcc ctgtctgcat ctgtgggaga cagagtcacc    60
atcacttgcc gggcgagtca ggacattttt aattatttag cctggtttca gcagaaacca   120
gggaaagttc ctgagctcct gatctctgct gcgtccactt tgcaatcagg ggtcccatct   180
cgtttcagtg gcagtggatc tgggacatat ttcactctca ccatcagcag cctgcagcct   240
gaagatattg ctacttatta ctgtcaaaga tataacagtg ccccgctcac tttcggcgga    300
gggaccaagg tggagatcaa a    321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Phe Asn Tyr
            20                  25                  30

Leu Ala Trp Phe Gln Gln Lys Pro Gly Lys Val Pro Glu Leu Leu Ile
        35                  40                  45

Ser Ala Ala Ser Thr Leu Gln Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Ile Ala Thr Tyr Tyr Cys Gln Arg Tyr Asn Ser Ala Pro Leu
                85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggacattt tcaattat    18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Asp Ile Phe Asn Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcgtcc    9

<210> SEQ ID NO 62
<211> LENGTH: 3
<212> TYPE: PRT
<213> ORGANISM: Artificial Sequence
<220> FEATURE:

<223> OTHER INFORMATION: Synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caaagatata acagtgcccc gctcact                27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Arg Tyr Asn Ser Ala Pro Leu Thr
1               5

<210> SEQ ID NO 65
<211> LENGTH: 360
<212> TYPE: DNA
<213> ORGANISM: Artificial Sequence
<220> FEATURE:
<223> OTHER INFORMATION: Synthetic

<400> SEQUENCE: 65
gaagtgcagc tggtggagtc tgggggaggc ttggtacagc ctggcaggtc cctgagactc     60
tcctgtgcag cctctggatt cacctttgat gattatgcca tgcactgggt ccggcaagct    120
ccagggaagg gcctggagtg ggtctcaggt attatttgga atagtggtca cataggctat    180
ggggactctg tgaagggccg attcaccatc tccagagaca cgccaagaa atccctatat     240 ctgcaaatga acagtctgag agctgaggac acggccttgt attattgtgc aagagatagt    300
gggaggtacc agtcctactt tgactactgg ggccagggaa ccctggtcac cgtctcctca    360

<210> SEQ ID NO 66
<211> LENGTH: 120
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ile Trp Asn Ser Gly His Ile Gly Tyr Gly Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ser Gly Arg Tyr Gln Ser Tyr Phe Asp Tyr Trp Gly Gln
            100                 105                 110

Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct ttgatgatta tgcc                                    24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Asp Asp Tyr Ala
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
attatttgga atagtggtca cata                                    24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Ile Trp Asn Ser Gly His Ile
1               5

<210> SEQ ID NO 71
<211> LENGTH: 39
<212> TYPE: DNA
<213> ORGANISM: Artificial Sequence
<220> FEATURE:
<223> OTHER INFORMATION: Synthetic

<400> SEQUENCE: 71
gcaagagata gtgggaggta ccagtcctac tttgactac                    39

<210> SEQ ID NO 72
<211> LENGTH: 13
<212> TYPE: PRT
<213> ORGANISM: Artificial Sequence
<220> FEATURE:
<223> OTHER INFORMATION: Synthetic -continued

<400> SEQUENCE: 72

Ala Arg Asp Ser Gly Arg Tyr Gln Ser Tyr Phe Asp Tyr
1               5                   10

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73

```
gacatccaga tgacccagtc tccttccacc ctgtctgcat ctgtaggaga cagagtcacc    60
atcacttgcc gggccagtca cattattagt agctggttgg cctggtatca gcagaaacca   120
gggaaagccc ctaaggtcct gatctttaag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatactt attctcggac gttcggccaa   300
gggaccaagg tggaaatcaa a                                              321
```

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Thr Leu Ser Ala Ser Val Gly
1               5                   10                  15

Asp Arg Val Thr Ile Thr Cys Arg Ala Ser His Ile Ile Ser Ser Trp
            20                  25                  30

Leu Ala Trp Tyr Gln Gln Lys Pro Gly Lys Ala Pro Lys Val Leu Ile
        35                  40                  45

Phe Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Arg
                85                  90                  95

Thr Phe Gly Gln Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

```
cacattatta gtagctgg                                                   18
```

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

His Ile Ile Ser Ser Trp
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 aaggcgtct                                                                 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Lys Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagtata atacttattc tcggacg                                            27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Asn Thr Tyr Ser Arg Thr
1               5

<210> SEQ ID NO 81
<211> LENGTH: 372
<212> TYPE: DNA
<213> ORGANISM: Artificial Sequence
<220> FEATURE:
<223> OTHER INFORMATION: Synthetic

<400> SEQUENCE: 81
caggtacagc tgcagcagtc aggtccagga ctggtgaagc cctcgcagac cctctcactc         60
acctgtgcca tctccgggga cagtgtctct agtaatactt ttgcttggaa ctggatcagg        120
cagtccccat cgagaggcct tgagtggctg ggaaggacat actacaggtc caagtggtat        180
attgattatg cagaatctgt gaaaagtcga ataaccatca ccccagacac atccaagaac        240
cagttctccc tgcagttgaa ctctgtgact cccgaggaca cggctctgta ttactgtgca        300
ggtggataca cctatgcccc ccgggggtgct tttgatatct ggggccaagg gacaatggtc        360
accgtctctt ca                                                           372

<210> SEQ ID NO 82
<211> LENGTH: 124
<212> TYPE: PRT
<213> ORGANISM: Artificial Sequence
<220> FEATURE:
<223> OTHER INFORMATION: Synthetic

<400> SEQUENCE: 82

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Thr Phe Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ile Asp Tyr Ala
    50                  55                  60

Glu Ser Val Lys Ser Arg Ile Thr Ile Thr Pro Asp Thr Ser Lys Asn
65                  70                  75                  80

Gln Phe Ser Leu Gln Leu Asn Ser Val Thr Pro Glu Asp Thr Ala Leu
                85                  90                  95

Tyr Tyr Cys Ala Gly Gly Tyr Thr Tyr Ala Pro Arg Gly Ala Phe Asp
            100                 105                 110

Ile Trp Gly Gln Gly Thr Met Val Thr Val Ser Ser
        115                 120
```

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
ggggacagtg tctctagtaa tacttttgct          30

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

```
Gly Asp Ser Val Ser Ser Asn Thr Phe Ala
1               5                   10
```

<210> SEQ ID NO 85
<211> LENGTH: 27
<212> TYPE: DNA
<213> ORGANISM: Artificial Sequence
<220> FEATURE:
<223> OTHER INFORMATION: Synthetic

<400> SEQUENCE: 85
acatactaca ggtccaagtg gtatatt          27

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

Thr Tyr Tyr Arg Ser Lys Trp Tyr Ile
1               5

<210> SEQ ID NO 87
<211> LENGTH: 42
<212> TYPE: DNA
<213> ORGANISM: Artificial Sequence
<220> FEATURE:
<223> OTHER INFORMATION: Synthetic

<400> SEQUENCE: 87
gcaggtggat acacctatgc ccccgggggt gcttttgata tc         42

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Ala Gly Gly Tyr Thr Tyr Ala Pro Arg Gly Ala Phe Asp Ile
1               5                   10

<210> SEQ ID NO 89
<211> LENGTH: 318
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaaactcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatgttagtt atttcacttt tggccagggg   300
accaagctgg agatcaaa                                                 318

<210> SEQ ID NO 90
<211> LENGTH: 106
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Val Ser Tyr Phe Thr
                85                  90                  95

Phe Gly Gln Gly Thr Lys Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagtatta gtagctgg                                              18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Ile Ser Ser Trp
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 aaggcgtct                                                         9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Lys Ala Ser
1

<210> SEQ ID NO 95
<211> LENGTH: 24
<212> TYPE: DNA
<213> ORGANISM: Artificial Sequence
<220> FEATURE:
<223> OTHER INFORMATION: Synthetic

<400> SEQUENCE: 95
caacagtatg ttagttattt cact                                       24

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Gln Gln Tyr Val Ser Tyr Phe Thr
1               5

<210> SEQ ID NO 97
<211> LENGTH: 354
<212> TYPE: DNA
<213> ORGANISM: Artificial Sequence
<220> FEATURE:
<223> OTHER INFORMATION: Synthetic

<400> SEQUENCE: 97

```
gaggtgcagc tggtggagtc tgggggaggc ttggtgcagc ctggagggtc cctgagactc      60
tcctgtgcag cctctggatt caccttcagt agttatgaaa tgaactgggt ccgccaggct     120
ccagggaagg ggctggagtg gatttcatac attagtagtc gtggtggtac catatactac     180
gcagactcta taaagggccg attcaccatc tacagagaca cgccaggaa ctcactgtat      240 ctgcaaatga acagcctgag agccgaggac acggctattt attactgtgc gagactgagt     300
ggggttgata ttttgatat ctggggccaa gggacaatgg tcaccgtctc ttca            354
```

<210> SEQ ID NO 98
<211> LENGTH: 118
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Ile
        35                  40                  45

Ser Tyr Ile Ser Ser Arg Gly Gly Thr Ile Tyr Tyr Ala Asp Ser Ile
    50                  55                  60

Lys Gly Arg Phe Thr Ile Tyr Arg Asp Asn Ala Arg Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Leu Ser Gly Val Asp Ile Phe Asp Ile Trp Gly Gln Gly Thr
            100                 105                 110

Met Val Thr Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct tcagtagtta tgaa                                              24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Ser Tyr Glu
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtagtc gtggtggtac cata                                           24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Ser Arg Gly Gly Thr Ile
1               5

<210> SEQ ID NO 103
<211> LENGTH: 33
<212> TYPE: DNA
<213> ORGANISM: Artificial Sequence
<220> FEATURE:
<223> OTHER INFORMATION: Synthetic

<400> SEQUENCE: 103
gcgagactga gtggggttga tattttgat atc                                  33

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

Ala Arg Leu Ser Gly Val Asp Ile Phe Asp Ile
1               5                   10

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaaactcct gatctatttt gcatccactt tgcaatcagg ggtcccttct    180
cgcttcagtg gcggtggatc tgggacagat ttcactctca ccatcagcag cctgcagcct    240
gaagatgttg caacttatta ctgtcaaagg tataacagtg ccccgctcac tttcggcgga    300
gggaccaagg tggagatcaa a                                              321

<210> SEQ ID NO 106
<211> LENGTH: 107
<212> TYPE: PRT
<213> ORGANISM: Artificial Sequence
<220> FEATURE:

<223> OTHER INFORMATION: Synthetic

<400> SEQUENCE: 106

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Tyr
            20                  25                  30
Leu Ala Trp Tyr Gln Gln Lys Pro Gly Lys Val Pro Lys Leu Leu Ile
        35                  40                  45
Tyr Phe Ala Ser Thr Leu Gln Ser Gly Val Pro Ser Arg Phe Ser Gly
    50                  55                  60
Gly Gly Ser Gly Thr Asp Phe Thr Leu Thr Ile Ser Ser Leu Gln Pro
65                  70                  75                  80
Glu Asp Val Ala Thr Tyr Tyr Cys Gln Arg Tyr Asn Ser Ala Pro Leu
                85                  90                  95
Thr Phe Gly Gly Gly Thr Lys Val Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggcatta gcaattat         18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
Gln Gly Ile Ser Asn Tyr
1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 tttgcatcc         9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

```
Phe Ala Ser
1
```

<210> SEQ ID NO 111
<211> LENGTH: 27
<212> TYPE: DNA

<213> ORGANISM: Artificial Sequence
<220> FEATURE:
<223> OTHER INFORMATION: Synthetic

<400> SEQUENCE: 111
caaaggtata acagtgcccc gctcact    27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Arg Tyr Asn Ser Ala Pro Leu Thr
1               5

<210> SEQ ID NO 113
<211> LENGTH: 363
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtacagc ctggggggtc cctgagactc    60
tcctgtgcag cctctggatt cacctttagc agctatgcca tgacctgggt ccgccaggct   120
ccagggaagg ggctggagtg gtctcagct attactggta gtgttggtaa cacatactac   180
gcagactctg tgaagggtcg gttcaccatc tccagagaca attccaagaa cacgctgtat   240
ctgcaaatga acagcctggg agccgaggat acggccgaat attactgtgc gaaggggcg   300 ggaatgacta cgaactggta cctcgatctc tggggccgtg caccctggt caccgtctcc   360 tca                                                                  363

<210> SEQ ID NO 114
<211> LENGTH: 121
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Thr Gly Ser Val Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Glu Tyr Tyr Cys
                85                  90                  95

Ala Lys Gly Ala Gly Met Thr Thr Asn Trp Tyr Leu Asp Leu Trp Gly
            100                 105                 110

Arg Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttagcagcta tgcc                                    24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Ser Tyr Ala
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
attactggta gtgttggtaa caca                                    24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Thr Gly Ser Val Gly Asn Thr
1               5

<210> SEQ ID NO 119
<211> LENGTH: 42
<212> TYPE: DNA
<213> ORGANISM: Artificial Sequence
<220> FEATURE:
<223> OTHER INFORMATION: Synthetic

<400> SEQUENCE: 119
gcgaaagggg cgggaatgac tacgaactgg tacctcgatc tc                42

<210> SEQ ID NO 120
<211> LENGTH: 14
<212> TYPE: PRT
<213> ORGANISM: Artificial Sequence
<220> FEATURE:
<223> OTHER INFORMATION: Synthetic

<400> SEQUENCE: 120

Ala Lys Gly Ala Gly Met Thr Thr Asn Trp Tyr Leu Asp Leu
1               5                   10

<210> SEQ ID NO 121
<211> LENGTH: 339
<212> TYPE: DNA

<213> ORGANISM: Artificial Sequence
<220> FEATURE:
<223> OTHER INFORMATION: Synthetic

<400> SEQUENCE: 121

```
gacatcgtga tgacccagtc tccagactcc ctggctgtgt ctctgggcgc gagggccacc    60
atcaactgca agtccagcca gagtgtttta tacagctcca acaatcagaa ctacttaact   120
tggtaccagc agaaaccagg acagcctcct aaacttctca ttaagtgggc atctacccgg   180
gaatccgggg tccctgaccg attcagtggc agcgggtctg ggacagattt cactctcacc   240
atcagcagcc tgcaggctga agatgtggca gtttattatt gtcagcaata tgctagtagt   300
ccgtatactt ttggccaggg gaccaagctg gagatcaaa                          339
```

<210> SEQ ID NO 122
<211> LENGTH: 113
<212> TYPE: PRT
<213> ORGANISM: Artificial Sequence
<220> FEATURE:
<223> OTHER INFORMATION: Synthetic

<400> SEQUENCE: 122

```
Asp Ile Val Met Thr Gln Ser Pro Asp Ser Leu Ala Val Ser Leu Gly
1               5                  10                  15

Ala Arg Ala Thr Ile Asn Cys Lys Ser Ser Gln Ser Val Leu Tyr Ser
            20                  25                  30

Ser Asn Asn Gln Asn Tyr Leu Thr Trp Tyr Gln Gln Lys Pro Gly Gln
        35                  40                  45

Pro Pro Lys Leu Leu Ile Lys Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ala Ser Ser Pro Tyr Thr Phe Gly Gln Gly Thr Lys Leu Glu Ile
            100                 105                 110

Lys
```

<210> SEQ ID NO 123
<211> LENGTH: 36
<212> TYPE: DNA
<213> ORGANISM: Artificial Sequence
<220> FEATURE:
<223> OTHER INFORMATION: Synthetic

<400> SEQUENCE: 123

```
cagagtgttt tatacagctc aacaatcag aactac                               36
```

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

```
Gln Ser Val Leu Tyr Ser Ser Asn Asn Gln Asn Tyr
1               5                  10
```

<210> SEQ ID NO 125
<211> LENGTH: 9

<212> TYPE: DNA
<213> ORGANISM: Artificial Sequence
<220> FEATURE:
<223> OTHER INFORMATION: Synthetic

<400> SEQUENCE: 125 tgggcatct                                                                 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Trp Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
cagcaatatg ctagtagtcc gtatact                                            27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Ala Ser Ser Pro Tyr Thr
1               5

<210> SEQ ID NO 129
<211> LENGTH: 351
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggc ttggtacagc ctggcaggtc cctgagactc         60
tcctgtgcag cctctggatt cacccttgat gatcatgccg tgcactgggt ccggcaagct        120
ccagggaagg gcctggagtg ggtctcaggt attagttgga atagtgttta catagactat        180
gcggactctg tgaagggccg attcaccatt tcagagaca acgccaagaa ctccctgtat         240
ctgcaaatga acagtctgag agctgaggac acggccttct attactgtgc aagagatatt        300
gagggagctc gggactactg ggccaggga accctggtca ccgtctcctc a                  351

<210> SEQ ID NO 130
<211> LENGTH: 117
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Leu Asp Asp His
            20                  25                  30

Ala Val His Trp Val Arg Gln Ala Pro Gly Lys Gly Leu Glu Trp Val
        35                  40                  45

Ser Gly Ile Ser Trp Asn Ser Val Tyr Ile Asp Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Arg Asp Ile Glu Gly Ala Arg Asp Tyr Trp Gly Gln Gly Thr Leu
            100                 105                 110

Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcaccc ttgatgatca tgcc                                              24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Leu Asp Asp His Ala
1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attagttgga atagtgttta cata                                              24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Trp Asn Ser Val Tyr Ile
1               5

<210> SEQ ID NO 135
<211> LENGTH: 30
<212> TYPE: DNA
<213> ORGANISM: Artificial Sequence
<220> FEATURE:
<223> OTHER INFORMATION: Synthetic

<400> SEQUENCE: 135
gcaagagata ttgagggagc tcgggactac                                    30

<210> SEQ ID NO 136
<211> LENGTH: 10
<212> TYPE: PRT
<213> ORGANISM: Artificial Sequence
<220> FEATURE:
<223> OTHER INFORMATION: Synthetic

<400> SEQUENCE: 136

Ala Arg Asp Ile Glu Gly Ala Arg Asp Tyr
1               5                   10

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctgtaggaga cagagtcacc     60
atcacttgcc gggctagtca gggcattaga aatgatttag ctggtatca gcaaaaacca    120 gggaaagccc ctaagcgcct gatctatgct gcatccagtt tgcaaagtgg ggtcccatca   180
aggttcagcg gcagtggata tgggacagaa ttcactctca caatcagcag cctgcagcct   240
gaagattttg caccttatta ctgtctacag cataatagtt acccgctcac tttcggcgga   300
gggaccaagg tggagatcaa a                                             321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Tyr Gly Thr Glu Phe Thr Leu Thr Ile Ser Ser Leu Gln Pro
65                  70                  75                  80

Glu Asp Phe Ala Pro Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 139
<211> LENGTH: 18
<212> TYPE: DNA
<213> ORGANISM: Artificial Sequence
<220> FEATURE:

<223> OTHER INFORMATION: Synthetic

<400> SEQUENCE: 139
cagggcatta gaaatgat                                                   18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Gly Ile Arg Asn Asp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc                                                              9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
ctacagcata atagttaccc gctcact                                         27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Leu Gln His Asn Ser Tyr Pro Leu Thr
1               5

<210> SEQ ID NO 145
<211> LENGTH: 357
<212> TYPE: DNA
<213> ORGANISM: Artificial Sequence
<220> FEATURE:
<223> OTHER INFORMATION: Synthetic

<400> SEQUENCE: 145

```
gaggtgcagc tggtggagtc tgggggaggc ttggtacagc ctggggggtc cctgagactc    60
tcctgtgcag cctctggatt cagttttagc atctatgcca tgagctggtt ccgccaggct   120
ccagggaagg ggctggagtg ggtctcagct attaatggtc gtggtgatgg cacacactac   180
gcagactccg tgaagggccg gttcaccatc tccagagaca attccaagac cacgctgtat   240
ctgcaaatga gcagcctgag agccgaggac acggccgtat attactgtgc gaaacccgtc   300
atgagtacaa atggttttga tatctggggc caagggacaa tggtcaccgt ctcttca      357
```

<210> SEQ ID NO 146  
<211> LENGTH: 119  
<212> TYPE: PRT  
<213> ORGANISM: Artificial Sequence  
<220> FEATURE:  
<223> OTHER INFORMATION: Synthetic

<400> SEQUENCE: 146

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ile Tyr
            20                  25                  30

Ala Met Ser Trp Phe Arg Gln Ala Pro Gly Lys Gly Leu Glu Trp Val
        35                  40                  45

Ser Ala Ile Asn Gly Arg Gly Asp Gly Thr His Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Ser Ser Leu Arg Ala Glu Asp Thr Ala Val Tyr Tyr Cys
                85                  90                  95

Ala Lys Pro Val Met Ser Thr Asn Gly Phe Asp Ile Trp Gly Gln Gly
            100                 105                 110

Thr Met Val Thr Val Ser Ser
        115
```

<210> SEQ ID NO 147  
<211> LENGTH: 24  
<212> TYPE: DNA  
<213> ORGANISM: Artificial Sequence  
<220> FEATURE:  
<223> OTHER INFORMATION: Synthetic

<400> SEQUENCE: 147

```
ggattcagtt ttagcatcta tgcc                                           24
```

<210> SEQ ID NO 148  
<211> LENGTH: 8  
<212> TYPE: PRT  
<213> ORGANISM: Artificial Sequence  
<220> FEATURE:  
<223> OTHER INFORMATION: Synthetic

<400> SEQUENCE: 148

```
Gly Phe Ser Phe Ser Ile Tyr Ala
1               5
```

<210> SEQ ID NO 149  
<211> LENGTH: 24  
<212> TYPE: DNA  
<213> ORGANISM: Artificial Sequence  
<220> FEATURE:  
<223> OTHER INFORMATION: Synthetic

<400> SEQUENCE: 149
attaatggtc gtggtgatgg caca                                              24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Asn Gly Arg Gly Asp Gly Thr
1               5

<210> SEQ ID NO 151
<211> LENGTH: 36
<212> TYPE: DNA
<213> ORGANISM: Artificial Sequence
<220> FEATURE:
<223> OTHER INFORMATION: Synthetic

<400> SEQUENCE: 151
gcgaaacccg tcatgagtac aaatggtttt gatatc                                 36

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Ala Lys Pro Val Met Ser Thr Asn Gly Phe Asp Ile
1               5                   10

<210> SEQ ID NO 153
<211> LENGTH: 318
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccttccacc ctgtctgcat ctgtaggaga cagagtcacc        60
atcacttgcc gggccagtca gagtattagt agctggttgg cctggtatca actgaaacca       120
gggaaagccc ctaagctcct aatctataag gcgtctaatt tagaaagtgg ggtcccatca       180
aggttcagcg gcagtggatc tgggacagag ttcactctca ccatcagcag cctgcagcct       240
gatgattttg caacttatta ctgccaacag tataatattt attggacgtt cggccaaggg       300
accaaggtgg aaatcaaa                                                    318

<210> SEQ ID NO 154
<211> LENGTH: 106
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Leu Lys Pro Gly Lys Ala Pro Lys Leu Leu Ile
            35                  40                  45

Tyr Lys Ala Ser Asn Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ile Tyr Trp Thr
                85                  90                  95

Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagagtatta gtagctgg                                                 18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Ser Ile Ser Ser Trp
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 aaggcgtct                                                            9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Lys Ala Ser
1

<210> SEQ ID NO 159
<211> LENGTH: 24
<212> TYPE: DNA
<213> ORGANISM: Artificial Sequence
<220> FEATURE:
<223> OTHER INFORMATION: Synthetic

<400> SEQUENCE: 159
caacagtata atatttattg gacg                                          24

```
<210> SEQ ID NO 160
<211> LENGTH: 8
<212> TYPE: PRT
<213> ORGANISM: Artificial Sequence
<220> FEATURE:
<223> OTHER INFORMATION: Synthetic

<400> SEQUENCE: 160

Gln Gln Tyr Asn Ile Tyr Trp Thr
1               5

<210> SEQ ID NO 161
<211> LENGTH: 351
<212> TYPE: DNA
<213> ORGANISM: Artificial Sequence
<220> FEATURE:
<223> OTHER INFORMATION: Synthetic

<400> SEQUENCE: 161
caggttcagc tggtgcagtc tggagctgag gtaaagaagc ctggggcctc agtgaaggtc    60
tcctgcaagg cttctggtta ccctttggc acctctggta tcacctgggt gcgacaggcc   120
cctggacaag gcttgagtg gatgggatgg agcagcgctt acaatggtaa aacagactat   180
gcacaaaagt tccaggacag agtcaccatg accacagaca catccacgac acaggctac   240 atggagatga ggagccttac atctgacgac acggccgtct attactgtac tactgtagta   300
cgtcgtccct ttgacttctg gggccaggga accctggtca ccgtctcctc a           351

<210> SEQ ID NO 162
<211> LENGTH: 117
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Thr Ser
            20                  25                  30

Gly Ile Thr Trp Val Arg Gln Ala Pro Gly Gln Gly Leu Glu Trp Met
        35                  40                  45

Gly Trp Ser Ser Ala Tyr Asn Gly Lys Thr Asp Tyr Ala Gln Lys Phe
    50                  55                  60

Gln Asp Arg Val Thr Met Thr Thr Asp Thr Ser Thr Thr Thr Gly Tyr
65                  70                  75                  80

Met Glu Met Arg Ser Leu Thr Ser Asp Asp Thr Ala Val Tyr Tyr Cys
                85                  90                  95

Thr Thr Val Val Arg Arg Pro Phe Asp Phe Trp Gly Gln Gly Thr Leu
            100                 105                 110

Val Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggttacacct ttggcaccct ctggt                                          24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Tyr Thr Phe Gly Thr Ser Gly
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
agcagcgctt acaatggtaa aaca                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ser Ser Ala Tyr Asn Gly Lys Thr
1               5

<210> SEQ ID NO 167
<211> LENGTH: 30
<212> TYPE: DNA
<213> ORGANISM: Artificial Sequence
<220> FEATURE:
<223> OTHER INFORMATION: Synthetic

<400> SEQUENCE: 167
actactgtag tacgtcgtcc ctttgacttc                                    30

<210> SEQ ID NO 168
<211> LENGTH: 10
<212> TYPE: PRT
<213> ORGANISM: Artificial Sequence
<220> FEATURE:
<223> OTHER INFORMATION: Synthetic

<400> SEQUENCE: 168

Thr Thr Val Val Arg Arg Pro Phe Asp Phe
1               5                   10

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtgggaga cagagtcacc    60
atcacttgtc gggcgagtca ggacattaat aatttttag cctggtttca gcagaaacca   120
gggaaagccc ctaagtccct gatctatgct gcatccagtt tacaaagtgg ggtcccatca   180

```
aagttcagcg gcggtggatc tgggacagat ttcgctctca ccatcagcag cctgcagcct      240
gaggattttg caacttatta ctgccaacag tatagttctt accctatcac cttcggccaa      300
gggacacgac tggagattaa a                                                 321
```

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Gly Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Tyr Ser Ser Tyr Pro Ile
                85                  90                  95

Thr Phe Gly Gln Gly Thr Arg Leu Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

```
caggacatta taatttt                                                      18
```

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

```
Gln Asp Ile Asn Asn Phe
1               5
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

```
gctgcatcc                                                                9
```

<210> SEQ ID NO 174
<211> LENGTH: 3
<212> TYPE: PRT

<213> ORGANISM: Artificial Sequence
<220> FEATURE:
<223> OTHER INFORMATION: Synthetic

<400> SEQUENCE: 174

Ala Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacagtata gttcttaccc tatcacc            27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Tyr Ser Ser Tyr Pro Ile Thr
1               5

<210> SEQ ID NO 177
<211> LENGTH: 351
<212> TYPE: DNA
<213> ORGANISM: Artificial Sequence
<220> FEATURE:
<223> OTHER INFORMATION: Synthetic

<400> SEQUENCE: 177
gaggtgcagc tggtggagtc tgggggaggc ttggtccagc cggggggtc cctcagactc      60
tcctgtatag tctctggatt cacctttagt ggctcttgga tgagttgggt ccgccagctt    120
ccaggaaagg gctggagtg gtggccaat attaaagaag atggaagtga ttcatactat      180
gtggactctg tggagggccg attcaccatc tccagagaca acgccaagag ttcactttat    240
ctgcaaatga acagtctgag agtcgacgac acggctgtat atttctgtgc gagagcgagg    300
acagtccctc tccactactg gggccagggc accctggtca ccgtctcctc a             351

<210> SEQ ID NO 178
<211> LENGTH: 117
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ile Val Ser Gly Phe Thr Phe Ser Gly Ser
            20                  25                  30

Trp Met Ser Trp Val Arg Gln Leu Pro Gly Lys Gly Leu Glu Trp Val
        35                  40                  45

Ala Asn Ile Lys Glu Asp Gly Ser Asp Ser Tyr Tyr Val Asp Ser Val
    50                  55                  60

Glu Gly Arg Phe Thr Ile Ser Arg Asp Asn Ala Lys Ser Ser Leu Tyr

```
            65                  70                  75                  80
Leu Gln Met Asn Ser Leu Arg Val Asp Asp Thr Ala Val Tyr Phe Cys
                    85                  90                  95
Ala Arg Ala Arg Thr Val Pro Leu His Tyr Trp Gly Gln Gly Thr Leu
                100                 105                 110
Val Thr Val Ser Ser
            115

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct ttagtggctc ttgg                                           24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Gly Ser Trp
1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
attaaagaag atggaagtga ttca                                           24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Lys Glu Asp Gly Ser Asp Ser
1               5

<210> SEQ ID NO 183
<211> LENGTH: 30
<212> TYPE: DNA
<213> ORGANISM: Artificial Sequence
<220> FEATURE:
<223> OTHER INFORMATION: Synthetic

<400> SEQUENCE: 183
gcgagagcga ggacagtccc tctccactac                                     30

<210> SEQ ID NO 184
<211> LENGTH: 10
<212> TYPE: PRT
<213> ORGANISM: Artificial Sequence
<220> FEATURE:
```

<223> OTHER INFORMATION: Synthetic

<400> SEQUENCE: 184

Ala Arg Ala Arg Thr Val Pro Leu His Tyr
1               5                   10

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185

```
gacatccaga tgacccagtc tccttccacc ctgtctgcat ctgtaggaga cagagtcacc    60
atcacttgcc gggccagtca gagtattaat atttggttgg cctggtatca acagaaacca   120
gggaaagccc ctaaactcct gatctatagg gcgtcttatt tagaaagtgg ggtcccatca   180
agtttcgccg gcggtggatc tgggacagaa ttcactctca ccatcagcag cctgcagcct   240
gatgactttg gaacttatta ttgtcaacac tataatagtt atccattcac ttttggccag   300
gggaccaagc tggagatcaa a                                             321
```

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ile Trp
            20                  25                  30

Leu Ala Trp Tyr Gln Gln Lys Pro Gly Lys Ala Pro Lys Leu Leu Ile
        35                  40                  45

Tyr Arg Ala Ser Tyr Leu Glu Ser Gly Val Pro Ser Ser Phe Ala Gly
    50                  55                  60

Gly Gly Ser Gly Thr Glu Phe Thr Leu Thr Ile Ser Ser Leu Gln Pro
65                  70                  75                  80

Asp Asp Phe Gly Thr Tyr Tyr Cys Gln His Tyr Asn Ser Tyr Pro Phe
                85                  90                  95

Thr Phe Gly Gln Gly Thr Lys Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187

```
cagagtatta atatttgg                                                  18
```

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Ser Ile Asn Ile Trp
1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 agggcgtct                                                                 9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Arg Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacactata atagttatcc attcact                                            27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln His Tyr Asn Ser Tyr Pro Phe Thr
1               5

<210> SEQ ID NO 193
<211> LENGTH: 357
<212> TYPE: DNA
<213> ORGANISM: Artificial Sequence
<220> FEATURE:
<223> OTHER INFORMATION: Synthetic

<400> SEQUENCE: 193
gaagtgcagc tggtggagtc tgggggaggc ttggtgcagc ctggcaggtc cctgagactc        60
tcctgtgcag cctctggatt cacctttgat ggttatgcca tgcactgggt ccggcaaggt       120
ccagggaagg gcctggagtg ggtctcaggt attagttggt atagtgatac cttaggctat       180
gcggactctg tgaagggccg attcaccatc tccagagaca cgccaaaaa ctccctgtat       240 ctgcaaatga acagtctgag aactgaggac acggccttct attactgtgc aaaaatctct       300
agcagcggct gggcctttga ctactggggc cagggaaccc tggtcaccgt ctcctca        357

```
<210> SEQ ID NO 194
<211> LENGTH: 119
<212> TYPE: PRT
<213> ORGANISM: Artificial Sequence
<220> FEATURE:
<223> OTHER INFORMATION: Synthetic

<400> SEQUENCE: 194
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Gly Tyr
            20                  25                  30

Ala Met His Trp Val Arg Gln Gly Pro Gly Lys Gly Leu Glu Trp Val
        35                  40                  45

Ser Gly Ile Ser Trp Tyr Ser Asp Thr Leu Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Phe Tyr Tyr Cys
                85                  90                  95

Ala Lys Ile Ser Ser Ser Gly Trp Ala Phe Asp Tyr Trp Gly Gln Gly
            100                 105                 110

Thr Leu Val Thr Val Ser Ser
        115

```
<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
```
ggattcacct ttgatggtta tgcc                                              24

```
<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196
```

Gly Phe Thr Phe Asp Gly Tyr Ala
1               5

```
<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
```
attagttggt atagtgatac ctta                                              24

```
<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198
```

```
Ile Ser Trp Tyr Ser Asp Thr Leu
1               5
```

<210> SEQ ID NO 199
<211> LENGTH: 36
<212> TYPE: DNA
<213> ORGANISM: Artificial Sequence
<220> FEATURE:
<223> OTHER INFORMATION: Synthetic

<400> SEQUENCE: 199

```
gcaaaaatct ctagcagcgg ctgggccttt gactac                              36
```

<210> SEQ ID NO 200
<211> LENGTH: 12
<212> TYPE: PRT
<213> ORGANISM: Artificial Sequence
<220> FEATURE:
<223> OTHER INFORMATION: Synthetic

<400> SEQUENCE: 200

```
Ala Lys Ile Ser Ser Ser Gly Trp Ala Phe Asp Tyr
1               5                   10
```

<210> SEQ ID NO 201
<211> LENGTH: 327
<212> TYPE: DNA
<213> ORGANISM: Artificial Sequence
<220> FEATURE:
<223> OTHER INFORMATION: Synthetic

<400> SEQUENCE: 201

```
gaaattgtgt tgacgcagtc tccaggtacc ctgtctttgt ctccagggga gagagccacc     60
ctctcttgca gggccagtca gagtgttagc agcgcctact tagcctggta ccagcagaaa    120
cctggccaga ctcccaggct cctcatctat ggtacatcca gcagggccac tggcatccca    180
gacaggttca gtggcagtgg gtctgggaca gacttcactc tcaccatcag cagactggag    240
cctgaagatt ttgcagtgta ttactgtcag cagtatggta gttcacctct attcactttc    300
ggccctggga ccaaagtgga tatcaaa                                       327
```

<210> SEQ ID NO 202
<211> LENGTH: 109
<212> TYPE: PRT
<213> ORGANISM: Artificial Sequence
<220> FEATURE:
<223> OTHER INFORMATION: Synthetic

<400> SEQUENCE: 202

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Ala
            20                  25                  30

Tyr Leu Ala Trp Tyr Gln Gln Lys Pro Gly Gln Thr Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

Leu Phe Thr Phe Gly Pro Gly Thr Lys Val Asp Ile Lys
            100                 105

<210> SEQ ID NO 203
<211> LENGTH: 21
<212> TYPE: DNA
<213> ORGANISM: Artificial Sequence
<220> FEATURE:
<223> OTHER INFORMATION: Synthetic

<400> SEQUENCE: 203
cacagtgtta gcagcgccta c                                           21

<210> SEQ ID NO 204
<211> LENGTH: 7
<212> TYPE: PRT
<213> ORGANISM: Artificial Sequence
<220> FEATURE:
<223> OTHER INFORMATION: Synthetic

<400> SEQUENCE: 204

His Ser Val Ser Ser Ala Tyr
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 ggtacatcc                                                          9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Gly Thr Ser
1

<210> SEQ ID NO 207
<211> LENGTH: 30
<212> TYPE: DNA
<213> ORGANISM: Artificial Sequence
<220> FEATURE:
<223> OTHER INFORMATION: Synthetic

<400> SEQUENCE: 207
cagcagtatg gtagttcacc tctattcact                                   30

<210> SEQ ID NO 208
<211> LENGTH: 10
<212> TYPE: PRT
<213> ORGANISM: Artificial Sequence
<220> FEATURE:
<223> OTHER INFORMATION: Synthetic

<400> SEQUENCE: 208

Gln Gln Tyr Gly Ser Ser Pro Leu Phe Thr
1               5                   10

<210> SEQ ID NO 209
<211> LENGTH: 363
<212> TYPE: DNA
<213> ORGANISM: Artificial Sequence
<220> FEATURE:
<223> OTHER INFORMATION: Synthetic

<400> SEQUENCE: 209

```
caggtacagc tgcagcagtc aggtccagga ctggtgaagc cctcgcagac cctctcactc      60
acctgtgtca tctccgggga cagtgtctct agtaacactg cttggaactg ggtcaggcag     120
tccccatcga gaggccttga gtggctggga aggacatact acaggtccaa gtggtataat     180
gattatgcag tatctgtgaa aagtcgaata accatcaacc cagacacatc caagaaccag     240
ttctccctgc tgatgaactc tgtgactccc gaagacacgg ctgtatatta ttgcgcaaga     300
gtggttcggg gacttaacta ctttgactac tggggccagg gaaccctggt cactgtctcc     360
tca                                                                   363
```

<210> SEQ ID NO 210
<211> LENGTH: 121
<212> TYPE: PRT
<213> ORGANISM: Artificial Sequence
<220> FEATURE:
<223> OTHER INFORMATION: Synthetic

<400> SEQUENCE: 210

```
Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Ser Val Ser Ser Asn
            20                  25                  30

Thr Ala Trp Asn Trp Val Arg Gln Ser Pro Ser Arg Gly Leu Glu Trp
        35                  40                  45

Leu Gly Arg Thr Tyr Tyr Arg Ser Lys Trp Tyr Asn Asp Tyr Ala Val
    50                  55                  60

Ser Val Lys Ser Arg Ile Thr Ile Asn Pro Asp Thr Ser Lys Asn Gln
65                  70                  75                  80

Phe Ser Leu Leu Met Asn Ser Val Thr Pro Glu Asp Thr Ala Val Tyr
                85                  90                  95

Tyr Cys Ala Arg Val Val Arg Gly Leu Asn Tyr Phe Asp Tyr Trp Gly
            100                 105                 110

Gln Gly Thr Leu Val Thr Val Ser Ser
        115                 120
```

<210> SEQ ID NO 211
<211> LENGTH: 27
<212> TYPE: DNA
<213> ORGANISM: Artificial Sequence
<220> FEATURE:
<223> OTHER INFORMATION: Synthetic

<400> SEQUENCE: 211

```
ggggacagtg tctctagtaa cactgct                                          27
```

<210> SEQ ID NO 212
<211> LENGTH: 9
<212> TYPE: PRT
<213> ORGANISM: Artificial Sequence
<220> FEATURE:
<223> OTHER INFORMATION: Synthetic

<400> SEQUENCE: 212

-continued

Gly Asp Ser Val Ser Ser Asn Thr Ala
1               5

<210> SEQ ID NO 213
<211> LENGTH: 27
<212> TYPE: DNA
<213> ORGANISM: Artificial Sequence
<220> FEATURE:
<223> OTHER INFORMATION: Synthetic

<400> SEQUENCE: 213
acatactaca ggtccaagtg gtataat                                            27

<210> SEQ ID NO 214
<211> LENGTH: 9
<212> TYPE: PRT
<213> ORGANISM: Artificial Sequence
<220> FEATURE:
<223> OTHER INFORMATION: Synthetic

<400> SEQUENCE: 214

Thr Tyr Tyr Arg Ser Lys Trp Tyr Asn
1               5

<210> SEQ ID NO 215
<211> LENGTH: 36
<212> TYPE: DNA
<213> ORGANISM: Artificial Sequence
<220> FEATURE:
<223> OTHER INFORMATION: Synthetic

<400> SEQUENCE: 215
gcaagagtgg ttcggggact taactacttt gactac                                  36

<210> SEQ ID NO 216
<211> LENGTH: 12
<212> TYPE: PRT
<213> ORGANISM: Artificial Sequence
<220> FEATURE:
<223> OTHER INFORMATION: Synthetic

<400> SEQUENCE: 216

Ala Arg Val Val Arg Gly Leu Asn Tyr Phe Asp Tyr
1               5                   10

<210> SEQ ID NO 217
<211> LENGTH: 339
<212> TYPE: DNA
<213> ORGANISM: Artificial Sequence
<220> FEATURE:
<223> OTHER INFORMATION: Synthetic

<400> SEQUENCE: 217
gacatcgtga tgacccagtc tccagactcc ctggctgtgt ctctgggcga gagggccacc        60
atcaactgca gtccagcca gagtgtttta tacaactcca acaataagaa ctacttagct        120
tggtaccagc agaaaccagg acagcctcct aaactactca tttactggtc atcttcccgg       180
gaatccgggg tccctgaccg attcagtggc agcgggtctg ggacagattt cactctcacc       240
atcagcggcc tgcaggctga agatgtggca atttattact gtcagcaata ttctacaatt       300
ccttacactt ttggccaggg gaccaagctg gagatcaaa                              339

<210> SEQ ID NO 218
<211> LENGTH: 113
<212> TYPE: PRT

<213> ORGANISM: Artificial Sequence
<220> FEATURE:
<223> OTHER INFORMATION: Synthetic

<400> SEQUENCE: 218

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Asn
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ser Ser Arg Glu Ser Gly Val
50                  55                  60
Pro Asp Arg Phe Ser Gly Ser Gly Ser Gly Thr Asp Phe Thr Leu Thr
65                  70                  75                  80
Ile Ser Gly Leu Gln Ala Glu Asp Val Ala Ile Tyr Tyr Cys Gln Gln
                85                  90                  95
Tyr Ser Thr Ile Pro Tyr Thr Phe Gly Gln Gly Thr Lys Leu Glu Ile
            100                 105                 110
Lys
```

<210> SEQ ID NO 219
<211> LENGTH: 36
<212> TYPE: DNA
<213> ORGANISM: Artificial Sequence
<220> FEATURE:
<223> OTHER INFORMATION: Synthetic

<400> SEQUENCE: 219
cagagtgttt tatacaactc caacaataag aactac          36

<210> SEQ ID NO 220
<211> LENGTH: 12
<212> TYPE: PRT
<213> ORGANISM: Artificial Sequence
<220> FEATURE:
<223> OTHER INFORMATION: Synthetic

<400> SEQUENCE: 220

```
Gln Ser Val Leu Tyr Asn Ser Asn Asn Lys Asn Tyr
1               5                   10
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 tggtcatct          9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

```
Trp Ser Ser
1
```

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
cagcaatatt ctacaattcc ttacact                                          27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Ser Thr Ile Pro Tyr Thr
1               5

<210> SEQ ID NO 225
<211> LENGTH: 351
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tggggggaggt gtggtacggc cggggggggtc cctgagactc     60 tcctgtgcag cctctggatt caagtttgat gattatggca tgacctgggt ccgccacgtt    120
ccagggaagg gctggagtg gtctctggt attaattgga atggtggtag aacaggttat       180
acagactctg tgaagggccg attcaccatc tccagagaca cgccaagaa ctccctgtat      240 ctgcaaatga acagtctgag agccgaggac acggccttgt atcactgtgc gggagctcgc    300
cgtgatgctt ttgatatctg gggccaaggg acaatggtca ccgtctcttc a             351

<210> SEQ ID NO 226
<211> LENGTH: 117
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Lys Phe Asp Asp Tyr
            20                  25                  30

Gly Met Thr Trp Val Arg His Val Pro Gly Lys Gly Leu Glu Trp Val
        35                  40                  45

Ser Gly Ile Asn Trp Asn Gly Arg Thr Gly Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Gly Ala Arg Arg Asp Ala Phe Asp Ile Trp Gly Gln Gly Thr Met
            100                 105                 110

Val Thr Val Ser Ser

```
                                 115

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcaagt ttgatgatta tggc                                           24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Lys Phe Asp Asp Tyr Gly
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attaattgga atggtggtag aaca                                           24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Asn Trp Asn Gly Gly Arg Thr
1               5

<210> SEQ ID NO 231
<211> LENGTH: 30
<212> TYPE: DNA
<213> ORGANISM: Artificial Sequence
<220> FEATURE:
<223> OTHER INFORMATION: Synthetic

<400> SEQUENCE: 231
gcgggagctc gccgtgatgc ttttgatatc                                     30

<210> SEQ ID NO 232
<211> LENGTH: 10
<212> TYPE: PRT
<213> ORGANISM: Artificial Sequence
<220> FEATURE:
<223> OTHER INFORMATION: Synthetic

<400> SEQUENCE: 232

Ala Gly Ala Arg Arg Asp Ala Phe Asp Ile
1               5                   10

<210> SEQ ID NO 233
```

<211> LENGTH: 321
<212> TYPE: DNA
<213> ORGANISM: Artificial Sequence
<220> FEATURE:
<223> OTHER INFORMATION: Synthetic

<400> SEQUENCE: 233

```
gacatccaga tgacccagtc tccatcctcc ctgtctgcat ctataggaga cagagtcacc    60
atcacttgcc gggcaagtca gaacattatc aaatatttaa attggtatca gcagaatgca   120
gggaaagccc ctaagctcct gatctatact gcatccagct tgcaaagtgg agtcccatca   180
cggttcagtg gcagcggatc tgggacagat tcactctca ccatcagcag tctgcaacct   240
gaagattttg caacttacta ctgtcaacag agttccagtt ccccatacac ttttggccag   300
gggaccaagc tggagatcaa a                                            321
```

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Leu Ser Ala Ser Ile Gly
1               5                   10                  15
Asp Arg Val Thr Ile Thr Cys Arg Ala Ser Gln Asn Ile Ile Lys Tyr
            20                  25                  30
Leu Asn Trp Tyr Gln Gln Asn Ala Gly Lys Ala Pro Lys Leu Leu Ile
        35                  40                  45
Tyr Thr Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Ser Ser Ser Pro Tyr
                85                  90                  95
Thr Phe Gly Gln Gly Thr Lys Leu Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
cagaacatta tcaaatat                                                  18
```

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Asn Ile Ile Lys Tyr
1               5

<210> SEQ ID NO 237
<211> LENGTH: 9

```
<212> TYPE: DNA
<213> ORGANISM: Artificial Sequence
<220> FEATURE:
<223> OTHER INFORMATION: Synthetic

<400> SEQUENCE: 237 actgcatcc                                                            9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Thr Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
caacagagtt ccagttcccc atacact                                       27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Ser Ser Ser Ser Pro Tyr Thr
1               5

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241
caggtcacct tgaaggagtc tggtcctgtg ctggtgaaac ccacacagac cctctcgctg     60
acctgcaccg tctcggggtt ctcactcagt gatgctggta tgggtgtgag ctggatccgt    120
cagcccccag ggaaggccct ggagtggctt gcacacattt tttcgaatga cgggaaatcc    180
tacagcacat ctctgaagag cagactcacc atctccaagg acacctccaa aaggcaggtg    240
gtccttacca tgaccaacat ggaccctgtg gacacagcca catattactg tgcacggata    300
cggactggaa cttattcctt ataccttgac tactggggcc agggaacccct ggtcactgtc    360 tcctca                                                              366

<210> SEQ ID NO 242
<211> LENGTH: 122
<212> TYPE: PRT
<213> ORGANISM: Artificial Sequence
<220> FEATURE:
<223> OTHER INFORMATION: Synthetic
```

<400> SEQUENCE: 242

Gln Val Thr Leu Lys Glu Ser Gly Pro Val Leu Val Lys Pro Thr Gln
1               5                   10                  15

Thr Leu Ser Leu Thr Cys Thr Val Ser Gly Phe Ser Leu Ser Asp Ala
            20                  25                  30

Gly Met Gly Val Ser Trp Ile Arg Gln Pro Pro Gly Lys Ala Leu Glu
        35                  40                  45

Trp Leu Ala His Ile Phe Ser Asn Asp Gly Lys Ser Tyr Ser Thr Ser
    50                  55                  60

Leu Lys Ser Arg Leu Thr Ile Ser Lys Asp Thr Ser Lys Arg Gln Val
65                  70                  75                  80

Val Leu Thr Met Thr Asn Met Asp Pro Val Asp Thr Ala Thr Tyr Tyr
                85                  90                  95

Cys Ala Arg Ile Arg Thr Gly Thr Tyr Ser Leu Tyr Leu Asp Tyr Trp
            100                 105                 110

Gly Gln Gly Thr Leu Val Thr Val Ser Ser
        115                 120

<210> SEQ ID NO 243
<211> LENGTH: 30
<212> TYPE: DNA
<213> ORGANISM: Artificial Sequence
<220> FEATURE:
<223> OTHER INFORMATION: Synthetic

<400> SEQUENCE: 243
gggttctcac tcagtgatgc tggtatgggt          30

<210> SEQ ID NO 244
<211> LENGTH: 10
<212> TYPE: PRT
<213> ORGANISM: Artificial Sequence
<220> FEATURE:
<223> OTHER INFORMATION: Synthetic

<400> SEQUENCE: 244

Gly Phe Ser Leu Ser Asp Ala Gly Met Gly
1               5                   10

<210> SEQ ID NO 245
<211> LENGTH: 21
<212> TYPE: DNA
<213> ORGANISM: Artificial Sequence
<220> FEATURE:
<223> OTHER INFORMATION: Synthetic

<400> SEQUENCE: 245
attttttcga atgacgggaa a          21

<210> SEQ ID NO 246
<211> LENGTH: 7
<212> TYPE: PRT
<213> ORGANISM: Artificial Sequence
<220> FEATURE:
<223> OTHER INFORMATION: Synthetic

<400> SEQUENCE: 246

Ile Phe Ser Asn Asp Gly Lys
1               5

<210> SEQ ID NO 247
<211> LENGTH: 42

```
<212> TYPE: DNA
<213> ORGANISM: Artificial Sequence
<220> FEATURE:
<223> OTHER INFORMATION: Synthetic

<400> SEQUENCE: 247
gcacggatac ggactggaac ttattcctta taccttgact ac                          42

<210> SEQ ID NO 248
<211> LENGTH: 14
<212> TYPE: PRT
<213> ORGANISM: Artificial Sequence
<220> FEATURE:
<223> OTHER INFORMATION: Synthetic

<400> SEQUENCE: 248

Ala Arg Ile Arg Thr Gly Thr Tyr Ser Leu Tyr Leu Asp Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccatcctcc ctgtctgcat ctgtaggaga cagagtcacc        60
atcacttgcc gggcaagtca gagcattaac agctatttaa attggtatca gcagaaacca       120
gggaaagccc ctaagctcct gctctatttt gcatccagtt tgcaaagtgg ggtcccatca       180
aggttcagtg gcagtggatc tgggacagat ttcactctca ccatcagcag tctgcaacct       240
gaagattttg caagttacta ctgtcaagag agttatagta ccccgtggac gttcggccaa       300
gggaccaagg tggaaatcaa a                                                 321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Leu
        35                  40                  45

Tyr Phe Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Glu Ser Tyr Ser Thr Pro Trp
                85                  90                  95

Thr Phe Gly Gln Gly Thr Lys Val Glu Ile Lys
            100                 105

<210> SEQ ID NO 251
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 251
cagagcatta acagctat                                                   18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Ser Ile Asn Ser Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 tttgcatcc                                                              9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Phe Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caagagagtt atagtacccc gtggacg                                         27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Glu Ser Tyr Ser Thr Pro Trp Thr
1               5

<210> SEQ ID NO 257
<211> LENGTH: 363
<212> TYPE: DNA
<213> ORGANISM: Artificial Sequence
<220> FEATURE:
<223> OTHER INFORMATION: Synthetic
```

<400> SEQUENCE: 257

```
caggtgcagc tggtggagtc tgggggaggc gtggtccagc ctgggaggtc cctgagactc    60
tcctgtgcag cgtctggatt caccttcagt gactataaca tgcactgggt ccgccaggct   120
ccaggcaagg gctggagtg gtggcggtt atatggtatg atggatctaa taaacactat    180
gcagactccg tgaagggccg attcacaatc tccagagaca attccaagaa cacgctctat   240
ctgcaaatga acagcctgag agccgaggac acggctgtgt attactgtgc gagagatgga   300
tttacgattt ttggaatggt tcttgactac tggggccagg gaaccctggt caccgtctcc   360
tca                                                                 363
```

<210> SEQ ID NO 258
<211> LENGTH: 121
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Asn Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Phe Thr Ile Phe Gly Met Val Leu Asp Tyr Trp Gly
            100                 105                 110

Gln Gly Thr Leu Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcacct tcagtgacta taac                                           24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

```
Gly Phe Thr Phe Ser Asp Tyr Asn
1               5
```

<210> SEQ ID NO 261
<211> LENGTH: 24
<212> TYPE: DNA

```
<213> ORGANISM: Artificial Sequence
<220> FEATURE:
<223> OTHER INFORMATION: Synthetic

<400> SEQUENCE: 261
atatggtatg atggatctaa taaa                                           24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Trp Tyr Asp Gly Ser Asn Lys
1               5

<210> SEQ ID NO 263
<211> LENGTH: 42
<212> TYPE: DNA
<213> ORGANISM: Artificial Sequence
<220> FEATURE:
<223> OTHER INFORMATION: Synthetic

<400> SEQUENCE: 263
gcgagagatg gatttacgat ttttggaatg gttcttgact ac                       42

<210> SEQ ID NO 264
<211> LENGTH: 14
<212> TYPE: PRT
<213> ORGANISM: Artificial Sequence
<220> FEATURE:
<223> OTHER INFORMATION: Synthetic

<400> SEQUENCE: 264

Ala Arg Asp Gly Phe Thr Ile Phe Gly Met Val Leu Asp Tyr
1               5                   10

<210> SEQ ID NO 265
<211> LENGTH: 327
<212> TYPE: DNA
<213> ORGANISM: Artificial Sequence
<220> FEATURE:
<223> OTHER INFORMATION: Synthetic

<400> SEQUENCE: 265
gaaattgtgt tgacgcagtc tccaggcacc ctgtctttgt ctccagggga aagagccacc    60
ctctcctgca gggccagtca gagtgttatc agcagctact tagcctggta ccagcagaag   120
cctggtcagg ctcccaggct cctcatctat ggtgcatcca gcagggccac tggcatccca   180
gacaggttca gtggcagtgg gtctgggaca gacttcactc tcaccatcag cagactggag   240
cctgaagact ttgcagtgtt ttactgtcag cagtatggta gttcacctcc cttcactttc   300
ggccctggga ccaaagtgga tatcaaa                                      327

<210> SEQ ID NO 266
<211> LENGTH: 109
<212> TYPE: PRT
<213> ORGANISM: Artificial Sequence
<220> FEATURE:
<223> OTHER INFORMATION: Synthetic

<400> SEQUENCE: 266

Glu Ile Val Leu Thr Gln Ser Pro Gly Thr Leu Ser Leu Ser Pro Gly
```

```
                1               5                  10                  15
            Glu Arg Ala Thr Leu Ser Cys Arg Ala Ser Gln Ser Val Ile Ser Ser
                        20                  25                  30

Tyr Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                50                  55                  60

Gly Ser Gly Ser Gly Thr Asp Phe Thr Leu Thr Ile Ser Arg Leu Glu
             65                 70                  75                  80

Pro Glu Asp Phe Ala Val Phe Tyr Cys Gln Gln Tyr Gly Ser Ser Pro
                            85                  90                  95

Pro Phe Thr Phe Gly Pro Gly Thr Lys Val Asp Ile Lys
                        100                 105
```

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
cagagtgtta tcagcagcta c                                               21

<210> SEQ ID NO 268
<211> LENGTH: 7
<212> TYPE: PRT
<213> ORGANISM: Artificial Sequence
<220> FEATURE:
<223> OTHER INFORMATION: Synthetic

<400> SEQUENCE: 268

Gln Ser Val Ile Ser Ser Tyr
1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 ggtgcatcc                                                              9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Gly Ala Ser
1

<210> SEQ ID NO 271
<211> LENGTH: 30
<212> TYPE: DNA
<213> ORGANISM: Artificial Sequence
<220> FEATURE:
<223> OTHER INFORMATION: Synthetic

<400> SEQUENCE: 271
cagcagtatg gtagttcacc tcccttcact                                      30

<210> SEQ ID NO 272
<211> LENGTH: 10
<212> TYPE: PRT
<213> ORGANISM: Artificial Sequence
<220> FEATURE:
<223> OTHER INFORMATION: Synthetic

<400> SEQUENCE: 272

Gln Gln Tyr Gly Ser Ser Pro Pro Phe Thr
1               5                   10

<210> SEQ ID NO 273
<211> LENGTH: 360
<212> TYPE: DNA
<213> ORGANISM: Artificial Sequence
<220> FEATURE:
<223> OTHER INFORMATION: Synthetic

<400> SEQUENCE: 273
gaagtgcagc tgttggagtc tgggggaggc ttggttcagc cggggggggac cctaagacta      60 tcctgtgcag cctctggatt cacctttagc gcctatgcca tgagttgggt ccgccaggct     120
ccagggaagg gactggagtg ggtctcttct attaatgttc gtgctggtga cacatactac     180
gcagactccg tgaagggccg cttcaccatc tccagagaca attccaagaa tacgctgttt     240
ctgctgatga acagcctgag agccgaagac acggccgcat attactgtgc gaaagccagg     300
tatagcagca attggggctt tgacttctgg ggccagggaa ccctggtcac cgtctcctca     360

<210> SEQ ID NO 274
<211> LENGTH: 120
<212> TYPE: PRT
<213> ORGANISM: Artificial Sequence
<220> FEATURE:
<223> OTHER INFORMATION: Synthetic

<400> SEQUENCE: 274

Glu Val Gln Leu Leu Glu Ser Gly Gly Gly Leu Val Gln Pro Gly Gly
1               5                   10                  15

Thr Leu Arg Leu Ser Cys Ala Ala Ser Gly Phe Thr Phe Ser Ala Tyr
                20                  25                  30

Ala Met Ser Trp Val Arg Gln Ala Pro Gly Lys Gly Leu Glu Trp Val
            35                  40                  45

Ser Ser Ile Asn Val Arg Ala Gly Asp Thr Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Leu Met Asn Ser Leu Arg Ala Glu Asp Thr Ala Ala Tyr Tyr Cys
                85                  90                  95

Ala Lys Ala Arg Tyr Ser Ser Asn Trp Gly Phe Asp Phe Trp Gly Gln
            100                 105                 110

Gly Thr Leu Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

```
<400> SEQUENCE: 275
ggattcacct ttagcgccta tgcc                                              24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser Ala Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attaatgttc gtgctggtga caca                                              24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Asn Val Arg Ala Gly Asp Thr
1               5

<210> SEQ ID NO 279
<211> LENGTH: 39
<212> TYPE: DNA
<213> ORGANISM: Artificial Sequence
<220> FEATURE:
<223> OTHER INFORMATION: Synthetic

<400> SEQUENCE: 279
gcgaaagcca ggtatagcag caattggggc tttgacttc                              39

<210> SEQ ID NO 280
<211> LENGTH: 13
<212> TYPE: PRT
<213> ORGANISM: Artificial Sequence
<220> FEATURE:
<223> OTHER INFORMATION: Synthetic

<400> SEQUENCE: 280

Ala Lys Ala Arg Tyr Ser Ser Asn Trp Gly Phe Asp Phe
1               5                   10

<210> SEQ ID NO 281
<211> LENGTH: 339
<212> TYPE: DNA
<213> ORGANISM: Artificial Sequence
<220> FEATURE:
<223> OTHER INFORMATION: Synthetic

<400> SEQUENCE: 281
gacatcgtga tgacccagtc tccagactcc ctgactgtgt ctctgggcgc gaggaccacc       60
```

```
atcaactgcc agtccagcca gactatttta cacagctcca acaatcacaa ctacttagct    120
tggtatcagc agaaaccggg actgcctcct aaactactca tttactggtc atctacccgg    180
gaatccggag tccctgaccg attcagcggc agcgggtctg ggacagattt cactctcacc    240 atcagcagc tgcaggctga agatgtggca atttattact gtcaacaata ttctaatact    300
ccgtacactt ttggccaggg gaccaagctg gagatcaat                            339
```

```
<210> SEQ ID NO 282
<211> LENGTH: 113
<212> TYPE: PRT
<213> ORGANISM: Artificial Sequence
<220> FEATURE:
<223> OTHER INFORMATION: Synthetic

<400> SEQUENCE: 282
```

Asp Ile Val Met Thr Gln Ser Pro Asp Ser Leu Thr Val Ser Leu Gly
1               5                   10                  15

Ala Arg Thr Thr Ile Asn Cys Gln Ser Ser Gln Thr Ile Leu His Ser
            20                  25                  30

Ser Asn Asn His Asn Tyr Leu Ala Trp Tyr Gln Gln Lys Pro Gly Leu
        35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Ser Asn Thr Pro Tyr Thr Phe Gly Gln Gly Thr Lys Leu Glu Ile
            100                 105                 110

Asn

```
<210> SEQ ID NO 283
<211> LENGTH: 36
<212> TYPE: DNA
<213> ORGANISM: Artificial Sequence
<220> FEATURE:
<223> OTHER INFORMATION: Synthetic

<400> SEQUENCE: 283
cagactattt tacacagctc caacaatcac aactac                                36

<210> SEQ ID NO 284
<211> LENGTH: 12
<212> TYPE: PRT
<213> ORGANISM: Artificial Sequence
<220> FEATURE:
<223> OTHER INFORMATION: Synthetic

<400> SEQUENCE: 284
```

Gln Thr Ile Leu His Ser Ser Asn Asn His Asn Tyr
1               5                   10

```
<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285
``` tggtcatct                                                                9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Trp Ser Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacaatatt ctaatactcc gtacact                                           27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Ser Asn Thr Pro Tyr Thr
1               5

<210> SEQ ID NO 289
<211> LENGTH: 345
<212> TYPE: DNA
<213> ORGANISM: Artificial Sequence
<220> FEATURE:
<223> OTHER INFORMATION: Synthetic

<400> SEQUENCE: 289
caggtgcagt tggtggaatc tgggggaggc gtggtccagc ctgggaggtc cctgagactc        60
tcctgtggag cctctggatt caccttcaga aattatggca tgcagtgggt ccgccagggt       120
ccaggcaagg ggctggagtg ggtgacactt atatcatttg atggaaatga taaatactat       180
gcagactccg tgaagggccg attcaccatc tccagagaca attccaagaa cacgctgttc       240
ctgcaaatga acagcctgag aactgaggac acggctgttt attactgtgc gagagggggg       300
gattttgact actggggaca gggaaccctg gtcaccgtct cctca                      345

<210> SEQ ID NO 290
<211> LENGTH: 115
<212> TYPE: PRT
<213> ORGANISM: Artificial Sequence
<220> FEATURE:
<223> OTHER INFORMATION: Synthetic

<400> SEQUENCE: 290

Gln Val Gln Leu Val Glu Ser Gly Gly Gly Val Val Gln Pro Gly Arg
1               5                  10                  15

Ser Leu Arg Leu Ser Cys Gly Ala Ser Gly Phe Thr Phe Arg Asn Tyr
            20                  25                  30

Gly Met Gln Trp Val Arg Gln Gly Pro Gly Lys Gly Leu Glu Trp Val

```
                35                  40                  45
Thr Leu Ile Ser Phe Asp Gly Asn Asp Lys Tyr Tyr Ala Asp Ser Val
         50                  55                  60
Lys Gly Arg Phe Thr Ile Ser Arg Asp Asn Ser Lys Asn Thr Leu Phe
 65                  70                  75                  80
Leu Gln Met Asn Ser Leu Arg Thr Glu Asp Thr Ala Val Tyr Tyr Cys
                 85                  90                  95
Ala Arg Gly Gly Asp Phe Asp Tyr Trp Gly Gln Gly Thr Leu Val Thr
                100                 105                 110
Val Ser Ser
        115
```

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct tcagaaatta tggc                                24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

```
Gly Phe Thr Phe Arg Asn Tyr Gly
1               5
```

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atatcatttg atggaaatga taaa                                24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

```
Ile Ser Phe Asp Gly Asn Asp Lys
1               5
```

<210> SEQ ID NO 295
<211> LENGTH: 24
<212> TYPE: DNA
<213> ORGANISM: Artificial Sequence
<220> FEATURE:
<223> OTHER INFORMATION: Synthetic

<400> SEQUENCE: 295
gcgagagggg gggattttga ctac                                24

<210> SEQ ID NO 296
<211> LENGTH: 8
<212> TYPE: PRT
<213> ORGANISM: Artificial Sequence
<220> FEATURE:
<223> OTHER INFORMATION: Synthetic

<400> SEQUENCE: 296

Ala Arg Gly Gly Asp Phe Asp Tyr
1               5

<210> SEQ ID NO 297
<211> LENGTH: 325
<212> TYPE: DNA
<213> ORGANISM: Artificial Sequence
<220> FEATURE:
<223> OTHER INFORMATION: Synthetic

<400> SEQUENCE: 297

```
gacatccaga tgacccagtc tccatcctcc ctgtctgcat ctgttggaga cagagtcacc    60
atcacttgcc gggcaagtca ggacattaga aaagatttag gctggtatca gcagaaacca   120
gggaaagccc ctaagcgtct gatctatgct gcatccagtt tacatagtgg ggtcccatca   180
aggttcagcg gcagtggatc tgggacagaa ttcactctca caatcagcag cctgcagcct   240
gaagattttg caacttatta ctgtctacaa cataatagtt accccatgta cacttttggt   300
caggggacca agctggagat caaaa                                         325
```

<210> SEQ ID NO 298
<211> LENGTH: 108
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Lys Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Met
                85                  90                  95

Tyr Thr Phe Gly Gln Gly Thr Lys Leu Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
caggacatta gaaaagat                                                  18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asp Ile Arg Lys Asp
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcatcc                                                              9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
1

<210> SEQ ID NO 303
<211> LENGTH: 30
<212> TYPE: DNA
<213> ORGANISM: Artificial Sequence
<220> FEATURE:
<223> OTHER INFORMATION: Synthetic

<400> SEQUENCE: 303
ctacaacata atagttaccc catgtacact                                       30

<210> SEQ ID NO 304
<211> LENGTH: 10
<212> TYPE: PRT
<213> ORGANISM: Artificial Sequence
<220> FEATURE:
<223> OTHER INFORMATION: Synthetic

<400> SEQUENCE: 304

Leu Gln His Asn Ser Tyr Pro Met Tyr Thr
1               5                   10

<210> SEQ ID NO 305
<211> LENGTH: 354
<212> TYPE: DNA
<213> ORGANISM: Artificial Sequence
<220> FEATURE:
<223> OTHER INFORMATION: Synthetic

<400> SEQUENCE: 305
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt atctcttggc atagtggcat cataggctat     180
gcggactctg tgaagggccg attcaccatc tccagagaca acgccaagaa ctccctgtat     240

```
ctgcaaatga acagtctgag aactgaggac gcggccttgt attattgtgc aaaaattggg        300
agctactttt actttgactc ctggggccag ggaaccctgg tcaccgtctc ctca              354
```

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp His Ser Gly Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Ala Ala Leu Tyr Tyr Cys
                85                  90                  95

Ala Lys Ile Gly Ser Tyr Phe Tyr Phe Asp Ser Trp Gly Gln Gly Thr
            100                 105                 110

Leu Val Thr Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

```
ggattcacct ttgatgatta tgcc                                               24
```

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Phe Thr Phe Asp Asp Tyr Ala
1               5
```

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309

```
atctcttggc atagtggcat cata                                               24
```

<210> SEQ ID NO 310
<211> LENGTH: 8

```
<212> TYPE: PRT
<213> ORGANISM: Artificial Sequence
<220> FEATURE:
<223> OTHER INFORMATION: Synthetic

<400> SEQUENCE: 310

Ile Ser Trp His Ser Gly Ile Ile
1               5

<210> SEQ ID NO 311
<211> LENGTH: 33
<212> TYPE: DNA
<213> ORGANISM: Artificial Sequence
<220> FEATURE:
<223> OTHER INFORMATION: Synthetic

<400> SEQUENCE: 311
gcaaaaattg ggagctactt ttactttgac tcc                                    33

<210> SEQ ID NO 312
<211> LENGTH: 11
<212> TYPE: PRT
<213> ORGANISM: Artificial Sequence
<220> FEATURE:
<223> OTHER INFORMATION: Synthetic

<400> SEQUENCE: 312

Ala Lys Ile Gly Ser Tyr Phe Tyr Phe Asp Ser
1               5                   10

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313
gaaattgtgt tgacgcagtc tccaggcacc ctgtctttgt ctccagggga aagagccacc        60
ctctcctgca gggccagtca gagtgttagc agcaactact tagcctggta ccagcagaaa       120
cctggccagg ctcccaggct cctcatctat ggtgcgtcca gcagggccac tggcatccca       180
gacaggttca gtggcagtgg gtctgggaca gacttcactc tcaccatcag cagactggag       240
cctgaagatt ttgcagttta ttactgtcag cagtttggta gctcagggta cacttttggc       300
caggggacca acctggagat caaa                                              324

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Gly
                 85                  90                  95

Tyr Thr Phe Gly Gln Gly Thr Asn Leu Glu Ile Lys
            100                 105

<210> SEQ ID NO 315
<211> LENGTH: 21
<212> TYPE: DNA
<213> ORGANISM: Artificial Sequence
<220> FEATURE:
<223> OTHER INFORMATION: Synthetic

<400> SEQUENCE: 315
cagagtgtta gcagcaacta c                                              21

<210> SEQ ID NO 316
<211> LENGTH: 7
<212> TYPE: PRT
<213> ORGANISM: Artificial Sequence
<220> FEATURE:
<223> OTHER INFORMATION: Synthetic

<400> SEQUENCE: 316

Gln Ser Val Ser Ser Asn Tyr
 1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 ggtgcgtcc                                                             9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Gly Ala Ser
 1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
cagcagtttg gtagctcagg gtacact                                        27

<210> SEQ ID NO 320
<211> LENGTH: 9
<212> TYPE: PRT
<213> ORGANISM: Artificial Sequence
<220> FEATURE:
<223> OTHER INFORMATION: Synthetic
```

<400> SEQUENCE: 320

Gln Gln Phe Gly Ser Ser Gly Tyr Thr
1               5

<210> SEQ ID NO 321
<211> LENGTH: 354
<212> TYPE: DNA
<213> ORGANISM: Artificial Sequence
<220> FEATURE:
<223> OTHER INFORMATION: Synthetic

<400> SEQUENCE: 321
gaggtgcagc tggtggagtc tgggggaggc ctggtcaagc cggggggtc cctgagactc    60 tcctgtgcag cctctggaat taccttcagt agttatagca tgaactgggt ccgccaggct   120
ccagggaagg gctggagtg gtctcatcc attagtacta ggagtagtct cattcactac    180
gcagactcag tgaagggccg attcaccatc tccagagaca acgccaagaa ctcactgtat   240
ctgcaaatga acagcctgag agacgaggac acggctgtgt attactgtgc gcgttgggat   300
gcggcagccg cctttgacta ctggggccag ggaaccctgg tcatcgtctc ctca        354

<210> SEQ ID NO 322
<211> LENGTH: 118
<212> TYPE: PRT
<213> ORGANISM: Artificial Sequence
<220> FEATURE:
<223> OTHER INFORMATION: Synthetic

<400> SEQUENCE: 322

Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Thr Arg Ser Ser Leu Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Asp Ala Ala Ala Ala Phe Asp Tyr Trp Gly Gln Gly Thr
            100                 105                 110

Leu Val Ile Val Ser Ser
        115

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggaattacct tcagtagtta tagc                                          24

<210> SEQ ID NO 324
<211> LENGTH: 8
<212> TYPE: PRT
<213> ORGANISM: Artificial Sequence
<220> FEATURE:

<223> OTHER INFORMATION: Synthetic

<400> SEQUENCE: 324

Gly Ile Thr Phe Ser Ser Tyr Ser
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagtacta ggagtagtct catt                                          24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Thr Arg Ser Ser Leu Ile
1               5

<210> SEQ ID NO 327
<211> LENGTH: 33
<212> TYPE: DNA
<213> ORGANISM: Artificial Sequence
<220> FEATURE:
<223> OTHER INFORMATION: Synthetic

<400> SEQUENCE: 327
gcgcgttggg atgcggcagc cgcctttgac tac                                33

<210> SEQ ID NO 328
<211> LENGTH: 11
<212> TYPE: PRT
<213> ORGANISM: Artificial Sequence
<220> FEATURE:
<223> OTHER INFORMATION: Synthetic

<400> SEQUENCE: 328

Ala Arg Trp Asp Ala Ala Ala Phe Asp Tyr
1               5                   10

<210> SEQ ID NO 329
<211> LENGTH: 321
<212> TYPE: DNA
<213> ORGANISM: Artificial Sequence
<220> FEATURE:
<223> OTHER INFORMATION: Synthetic

<400> SEQUENCE: 329
gacatccagt tgacccagtc tccatccttc ctgtctgcat ctgtaggaga cagagtcacc    60
atcacttgct gggccagtca gggcattagc agttatttag cctggtatca gcaaaaacca   120
gggaaagccc ctaagctcct gatctatgtt gcatccactt tgcaaagtgg ggtcccatca   180
aggttcagcg gcagtggatc tgggacagaa ttcactctca caatcagcag cctgcagcct   240
gaagattttg caacttattt ctgtcaacag cttaatagtt acccgctcac tttcggcgga   300
gggaccaagg tggagatcaa a                                             321

<210> SEQ ID NO 330
<211> LENGTH: 107
<212> TYPE: PRT
<213> ORGANISM: Artificial Sequence
<220> FEATURE:
<223> OTHER INFORMATION: Synthetic

<400> SEQUENCE: 330

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Leu Asn Ser Tyr Pro Leu
                85                  90                  95

Thr Phe Gly Gly Gly Thr Lys Val Glu Ile Lys
            100                 105

<210> SEQ ID NO 331
<211> LENGTH: 18
<212> TYPE: DNA
<213> ORGANISM: Artificial Sequence
<220> FEATURE:
<223> OTHER INFORMATION: Synthetic

<400> SEQUENCE: 331
cagggcatta gcagttat                                                        18

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

Gln Gly Ile Ser Ser Tyr
1               5

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 gttgcatcc                                                                   9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Val Ala Ser

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
caacagctta atagttaccc gctcact                                       27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Gln Gln Leu Asn Ser Tyr Pro Leu Thr
1               5

<210> SEQ ID NO 337
<211> LENGTH: 342
<212> TYPE: DNA
<213> ORGANISM: Artificial Sequence
<220> FEATURE:
<223> OTHER INFORMATION: Synthetic

<400> SEQUENCE: 337
caggtccagt tggtacagtc tggggctgag gtgcagaagc ctggggcctc agtgaaggtc    60
tcctgcaagg tttccggata caccctcact gcattatcca tacactgggt gcgacaagct   120
cctggaaaag ggcttgagtg gatgggaaat tttgatcctg agatggtga aacaatccac   180 gcacagaagt tccagggcag agtcaccatg accggggaca catctacaga cacagcctac   240
atggaactga gcagcctgag atctgaggac acggccgtgt attattgtgt aggggttact   300
tttgactact ggggccaggg aaccctggtc accgtctcct ca                      342

<210> SEQ ID NO 338
<211> LENGTH: 114
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Gln Lys Pro Gly Ala
1               5                   10                  15

Ser Val Lys Val Ser Cys Lys Val Ser Gly Tyr Thr Leu Thr Ala Leu
                20                  25                  30

Ser Ile His Trp Val Arg Gln Ala Pro Gly Lys Gly Leu Glu Trp Met
            35                  40                  45

Gly Asn Phe Asp Pro Gly Asp Gly Glu Thr Ile His Ala Gln Lys Phe
        50                  55                  60

Gln Gly Arg Val Thr Met Thr Gly Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Gly Val Thr Phe Asp Tyr Trp Gly Gln Gly Thr Leu Val Thr Val
            100                 105                 110

Ser Ser

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggatacaccc tcactgcatt atcc                                          24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Tyr Thr Leu Thr Ala Leu Ser
1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
tttgatcctg gagatggtga aaca                                          24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Phe Asp Pro Gly Asp Gly Glu Thr
1               5

<210> SEQ ID NO 343
<211> LENGTH: 21
<212> TYPE: DNA
<213> ORGANISM: Artificial Sequence
<220> FEATURE:
<223> OTHER INFORMATION: Synthetic

<400> SEQUENCE: 343 gtagggtta cttttgacta c                                              21

<210> SEQ ID NO 344
<211> LENGTH: 7
<212> TYPE: PRT
<213> ORGANISM: Artificial Sequence
<220> FEATURE:
<223> OTHER INFORMATION: Synthetic

<400> SEQUENCE: 344

Val Gly Val Thr Phe Asp Tyr
1               5

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345

```
gaaattgtga tgacgcagtc tccagccacc ctgtctgtgt ctccagggga aagagccacc    60
ctctcctgca gggccagtca gagtgttgcc agcaacttag cctggtacca gcagaaacct   120
ggccaggctc ccaggctcct cctctatggt gcatccacca gggccactgg tatcccagcc   180
aggttcagtg gcagtgggtc tgggacagag ttcactctca ccatcagcag cctgcagtct   240
gaggattttg cactttatta ctgtcagcac tataataact ggccgctcac tttcggcgga   300
gggaccaagg tggagatcaa a                                              321
```

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ala Ser Asn
            20                  25                  30

Leu Ala Trp Tyr Gln Gln Lys Pro Gly Gln Ala Pro Arg Leu Leu Leu
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Leu Tyr Tyr Cys Gln His Tyr Asn Asn Trp Pro Leu
                85                  90                  95

Thr Phe Gly Gly Gly Thr Lys Val Glu Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347

```
cagagtgttg ccagcaac                                                   18
```

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

```
Gln Ser Val Ala Ser Asn
1               5
```

<210> SEQ ID NO 349

<211> LENGTH: 9
<212> TYPE: DNA
<213> ORGANISM: Artificial Sequence
<220> FEATURE:
<223> OTHER INFORMATION: Synthetic

<400> SEQUENCE: 349 ggtgcatcc                                                                                    9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Gly Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
cagcactata ataactggcc gctcact                                                                27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln His Tyr Asn Asn Trp Pro Leu Thr
1               5

<210> SEQ ID NO 353
<211> LENGTH: 345
<212> TYPE: DNA
<213> ORGANISM: Artificial Sequence
<220> FEATURE:
<223> OTHER INFORMATION: Synthetic

<400> SEQUENCE: 353
gaggtgcagc ttgtagagtc tgggggagac ttggtacatc ctggcaggtc cctgagactc         60
tcctgtgcag cctctggttt cccctttgat gagtatgcca tgcactgggt ccggcaagtt        120
ccagggaagg gcctggagtg ggtctcaggt attagttgga gtaataataa cataggctat        180
gcggactctg tgaagggccg attcaccatc tccagagaca cgccaaaaa ctccctgtat         240 ctacaaatga acagtctgag acctgaggac acggcctttt attactgtgc aaaatctgga        300
atctttgact cctggggcca gggaaccctg gtcaccgtct cctca                        345

<210> SEQ ID NO 354
<211> LENGTH: 115
<212> TYPE: PRT
<213> ORGANISM: Artificial Sequence
<220> FEATURE:
<223> OTHER INFORMATION: Synthetic

<400> SEQUENCE: 354

```
Glu Val Gln Leu Val Glu Ser Gly Gly Asp Leu Val His Pro Gly Arg
1               5                   10                  15

Ser Leu Arg Leu Ser Cys Ala Ala Ser Gly Phe Pro Phe Asp Glu Tyr
            20                  25                  30

Ala Met His Trp Val Arg Gln Val Pro Gly Lys Gly Leu Glu Trp Val
        35                  40                  45

Ser Gly Ile Ser Trp Ser Asn Asn Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Phe Tyr Tyr Cys
                85                  90                  95

Ala Lys Ser Gly Ile Phe Asp Ser Trp Gly Gln Gly Thr Leu Val Thr
            100                 105                 110

Val Ser Ser
        115
```

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggtttcccct ttgatgagta tgcc           24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

```
Gly Phe Pro Phe Asp Glu Tyr Ala
1               5
```

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
attagttgga gtaataataa cata           24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

```
Ile Ser Trp Ser Asn Asn Asn Ile
1               5
```

<210> SEQ ID NO 359
<211> LENGTH: 24
<212> TYPE: DNA

<213> ORGANISM: Artificial Sequence
<220> FEATURE:
<223> OTHER INFORMATION: Synthetic

<400> SEQUENCE: 359

```
gcaaaatctg gaatctttga ctcc                                          24
```

<210> SEQ ID NO 360
<211> LENGTH: 8
<212> TYPE: PRT
<213> ORGANISM: Artificial Sequence
<220> FEATURE:
<223> OTHER INFORMATION: Synthetic

<400> SEQUENCE: 360

Ala Lys Ser Gly Ile Phe Asp Ser
1               5

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361

```
gaaatagtga tgacgcagtc tccagccacc ctgtctgtgt ctccagggga aagagccacc    60
ctctcctgca gggccagtca gagtgttagc agggacttag cctggtacca gcagaaacct   120
ggccaggctc ccaggctcct catccatggt gcatccacca gggccactgg tatcccagcc   180
aggttcagtg gcagtgggtc tggggcagag ttcactctca tcatcagcag cctgcagtct   240
gaagattttg cagttttatta ctgtcagcag tataacaact ggcctctcac tttcggcgga   300
gggaccaagg tggagatcaa a                                             321
```

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asp
            20                  25                  30

Leu Ala Trp Tyr Gln Gln Lys Pro Gly Gln Ala Pro Arg Leu Leu Ile
        35                  40                  45

His Gly Ala Ser Thr Arg Ala Thr Gly Ile Pro Ala Arg Phe Ser Gly
    50                  55                  60

Ser Gly Ser Gly Ala Glu Phe Thr Leu Ile Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagagtgtta gcagggac                                                   18

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

Gln Ser Val Ser Arg Asp
1               5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 ggtgcatcc                                                              9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Gly Ala Ser
1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
cagcagtata acaactggcc tctcact                                          27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Gln Tyr Asn Asn Trp Pro Leu Thr
1               5

<210> SEQ ID NO 369
<211> LENGTH: 354
<212> TYPE: DNA
<213> ORGANISM: Artificial Sequence
<220> FEATURE:
<223> OTHER INFORMATION: Synthetic

<400> SEQUENCE: 369

```
gaggtgcact tggtggagtc tgggggaggc ttggttcagc ctggagggtc cctgagactc      60
tcctgcgcag cctctgggtt caccttcagt agttatgaaa tgaactgggt ccgccagact     120
ccagggaagg ggctggagtg gatttcacac attagtagtc gtagtgttat aatatattat     180
gcagactctg tgaagggccg attcaccatc tccagagaca tgccaagaa ctcactgttt      240 ctgcaaatga acagtctgag agccgaagac acggctgtct atttctgtgc ggggattact     300 attttggta tccctgaata ctggggccag ggaaccctgg tcaccgtctc ctca            354
```

<210> SEQ ID NO 370
<211> LENGTH: 118
<212> TYPE: PRT
<213> ORGANISM: Artificial Sequence
<220> FEATURE:
<223> OTHER INFORMATION: Synthetic

<400> SEQUENCE: 370

```
Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Thr Pro Gly Lys Gly Leu Glu Trp Ile
        35                  40                  45

Ser His Ile Ser Ser Arg Ser Val Ile Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Ala Gly Ile Thr Ile Phe Gly Ile Pro Glu Tyr Trp Gly Gln Gly Thr
            100                 105                 110

Leu Val Thr Val Ser Ser
        115
```

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371

```
gggttcacct tcagtagtta tgaa                                             24
```

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

```
Gly Phe Thr Phe Ser Ser Tyr Glu
1               5
```

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
attagtagtc gtagtgttat aata 24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Ser Arg Ser Val Ile Ile
1               5

<210> SEQ ID NO 375
<211> LENGTH: 33
<212> TYPE: DNA
<213> ORGANISM: Artificial Sequence
<220> FEATURE:
<223> OTHER INFORMATION: Synthetic

<400> SEQUENCE: 375
gcggggatta ctattttggg tatccctgaa tac 33

<210> SEQ ID NO 376
<211> LENGTH: 11
<212> TYPE: PRT
<213> ORGANISM: Artificial Sequence
<220> FEATURE:
<223> OTHER INFORMATION: Synthetic

<400> SEQUENCE: 376

Ala Gly Ile Thr Ile Phe Gly Ile Pro Glu Tyr
1               5                   10

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gaaattgtgt tgacacagtc tccagccacc ctgtctttgt ctccagggga aagagccacc    60
ctctcctgca gggccagtca gagtgttagt agttactttg cctggtatca acagaaacct   120
ggccaggctc ccaggctcct catctatgat cgtccagca gggccacagg catcccaacc    180
aggttcagtg gcagtgggtc tgggacagac ttcactctca ccatcagcag cctagagcct   240
gaagattttg cagtttatta ctgtcagcaa cgaagcagct ggcctatcac cttcggccag   300
gggacacgac tggagattaa a                                             321

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr

```
            20                  25                  30
Phe Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Thr Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Ile
                85                  90                  95

Thr Phe Gly Gln Gly Thr Arg Leu Glu Ile Lys
            100                 105
```

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379
cagagtgtta gtagttac                                          18

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

Gln Ser Val Ser Ser Tyr
1               5

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381 gatgcgtcc                                                    9

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Asp Ala Ser
1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
cagcaacgaa gcagctggcc tatcacc                                27

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Gln Gln Arg Ser Ser Trp Pro Ile Thr
1               5

<210> SEQ ID NO 385
<211> LENGTH: 351
<212> TYPE: DNA
<213> ORGANISM: Artificial Sequence
<220> FEATURE:
<223> OTHER INFORMATION: Synthetic

<400> SEQUENCE: 385
gaggtgcagc tgttggagtc tgggggaggc ttcgtacagc cggggggtc cctgagactc      60 tcctgtgcag cctctggatt caccttagt tcctatgcca tgagctgggt ccgccaggct    120
ccagggaagg gctggagtg gtctcaatt attagttcta atggtcgtta cacatactat    180
gcagactccg tgaagggccg gttcaccatc tccagagaca attccaagaa cacgctgtat    240
ctccaaatga acagcctgag agccgaagac acggccgtct attactgtgc cactgtaact    300
ggggactggt tcgacccctg gggccaggga accctggtca ccgtctcctc a            351

<210> SEQ ID NO 386
<211> LENGTH: 117
<212> TYPE: PRT
<213> ORGANISM: Artificial Sequence
<220> FEATURE:
<223> OTHER INFORMATION: Synthetic

<400> SEQUENCE: 386

Glu Val Gln Leu Leu Glu Ser Gly Gly Gly Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Ser Ser Asn Gly Arg Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Val Thr Gly Asp Trp Phe Asp Pro Trp Gly Gln Gly Thr Leu
            100                 105                 110

Val Thr Val Ser Ser
        115

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387

```
ggattcacct ttagttccta tgcc                                           24
```

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Ser Ser Tyr Ala
1               5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389

```
attagttcta atggtcgtta caca                                           24
```

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Ser Ser Asn Gly Arg Tyr Thr
1               5

<210> SEQ ID NO 391
<211> LENGTH: 30
<212> TYPE: DNA
<213> ORGANISM: Artificial Sequence
<220> FEATURE:
<223> OTHER INFORMATION: Synthetic

<400> SEQUENCE: 391

```
gccactgtaa ctggggactg gttcgacccc                                     30
```

<210> SEQ ID NO 392
<211> LENGTH: 10
<212> TYPE: PRT
<213> ORGANISM: Artificial Sequence
<220> FEATURE:
<223> OTHER INFORMATION: Synthetic

<400> SEQUENCE: 392

Ala Thr Val Thr Gly Asp Trp Phe Asp Pro
1               5                   10

<210> SEQ ID NO 393
<211> LENGTH: 321
<212> TYPE: DNA
<213> ORGANISM: Artificial Sequence
<220> FEATURE:
<223> OTHER INFORMATION: Synthetic

<400> SEQUENCE: 393

```
gacatccagt tgacccagtc tccatccttc ctgtctgcat ctgtaggaga cagagtcacc    60
atcacttgtt gggccagtca ggacattgac atttctttag cctggtatca gcaaaaacca   120
```

| | | |
|---|---|---|
| gggaaagccc ctaagctctt gatctatgct gcatccactt tgcaaagtgg ggtcccttca | 180 |
| aagttcagcg gcagtggatc tgggacagat tcactctca caatcagcag cctgcagcct | 240 |
| gaagattttt caacttatta ctgtcaacaa cttaatagtt acccgatcac cttcggccaa | 300 |
| gggacacgac tggacattaa a | 321 |

```
<210> SEQ ID NO 394
<211> LENGTH: 107
<212> TYPE: PRT
<213> ORGANISM: Artificial Sequence
<220> FEATURE:
<223> OTHER INFORMATION: Synthetic

<400> SEQUENCE: 394
```

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Asp Ile Ser
            20                  25                  30

Leu Ala Trp Tyr Gln Lys Pro Gly Lys Ala Pro Lys Leu Leu Ile
        35                  40                  45

Tyr Ala Ala Ser Thr Leu Gln Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ser Thr Tyr Tyr Cys Gln Gln Leu Asn Ser Tyr Pro Ile
                85                  90                  95

Thr Phe Gly Gln Gly Thr Arg Leu Asp Ile Lys
            100                 105

```
<210> SEQ ID NO 395
<211> LENGTH: 18
<212> TYPE: DNA
<213> ORGANISM: Artificial Sequence
<220> FEATURE:
<223> OTHER INFORMATION: Synthetic

<400> SEQUENCE: 395
```
caggacattg acatttct                                                18

```
<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396
```

Gln Asp Ile Asp Ile Ser
1               5

```
<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397
``` gctgcatcc                                                           9

```
<210> SEQ ID NO 398
<211> LENGTH: 3
```

```
<212> TYPE: PRT
<213> ORGANISM: Artificial Sequence
<220> FEATURE:
<223> OTHER INFORMATION: Synthetic

<400> SEQUENCE: 398

Ala Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
caacaactta atagttaccc gatcacc                                              27

<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Gln Gln Leu Asn Ser Tyr Pro Ile Thr
1               5

<210> SEQ ID NO 401
<211> LENGTH: 267
<212> TYPE: PRT
<213> ORGANISM: Artificial Sequence
<220> FEATURE:
<223> OTHER INFORMATION: human PRLR ecto-mmH

<400> SEQUENCE: 401

Met His Arg Pro Arg Arg Gly Thr Arg Pro Pro Leu Ala Leu
1               5                   10                  15

Leu Ala Ala Leu Leu Leu Ala Ala Arg Gly Ala Asp Ala Gln Leu Pro
            20                  25                  30

Pro Gly Lys Pro Glu Ile Phe Lys Cys Arg Ser Pro Asn Lys Glu Thr
        35                  40                  45

Phe Thr Cys Trp Trp Arg Pro Gly Thr Asp Gly Gly Leu Pro Thr Asn
    50                  55                  60

Tyr Ser Leu Thr Tyr His Arg Glu Gly Glu Thr Leu Met His Glu Cys
65                  70                  75                  80

Pro Asp Tyr Ile Thr Gly Gly Pro Asn Ser Cys His Phe Gly Lys Gln
                85                  90                  95

Tyr Thr Ser Met Trp Arg Thr Tyr Ile Met Met Val Asn Ala Thr Asn
            100                 105                 110

Gln Met Gly Ser Ser Phe Ser Asp Glu Leu Tyr Val Asp Val Thr Tyr
        115                 120                 125

Ile Val Gln Pro Asp Pro Pro Leu Glu Leu Ala Val Glu Val Lys Gln
    130                 135                 140

Pro Glu Asp Arg Lys Pro Tyr Leu Trp Ile Lys Trp Ser Pro Pro Thr
145                 150                 155                 160

Leu Ile Asp Leu Lys Thr Gly Trp Phe Thr Leu Leu Tyr Glu Ile Arg
                165                 170                 175

Leu Lys Pro Glu Lys Ala Ala Glu Trp Glu Ile His Phe Ala Gly Gln
```

```
                    180                 185                 190
Gln Thr Glu Phe Lys Ile Leu Ser Leu His Pro Gly Gln Lys Tyr Leu
                195                 200                 205

Val Gln Val Arg Cys Lys Pro Asp His Gly Tyr Trp Ser Ala Trp Ser
            210                 215                 220

Pro Ala Thr Phe Ile Gln Ile Pro Ser Asp Phe Thr Met Asn Asp Glu
225                 230                 235                 240

Gln Lys Leu Ile Ser Glu Glu Asp Leu Gly Gly Glu Gln Lys Leu Ile
                245                 250                 255

Ser Glu Glu Asp Leu His His His His His His
                260                 265

<210> SEQ ID NO 402
<211> LENGTH: 472
<212> TYPE: PRT
<213> ORGANISM: Artificial Sequence
<220> FEATURE:
<223> OTHER INFORMATION: human PRLR ecto-mFc

<400> SEQUENCE: 402

Met His Arg Pro Arg Arg Gly Thr Arg Pro Pro Leu Ala Leu
1               5                   10                  15

Leu Ala Leu Leu Leu Ala Ala Arg Gly Ala Asp Ala Gln Leu Pro
                20                  25                  30

Pro Gly Lys Pro Glu Ile Phe Lys Cys Arg Ser Pro Asn Lys Glu Thr
            35                  40                  45

Phe Thr Cys Trp Trp Arg Pro Gly Thr Asp Gly Gly Leu Pro Thr Asn
        50                  55                  60

Tyr Ser Leu Thr Tyr His Arg Glu Gly Glu Thr Leu Met His Glu Cys
65                  70                  75                  80

Pro Asp Tyr Ile Thr Gly Gly Pro Asn Ser Cys His Phe Gly Lys Gln
                85                  90                  95

Tyr Thr Ser Met Trp Arg Thr Tyr Ile Met Met Val Asn Ala Thr Asn
            100                 105                 110

Gln Met Gly Ser Ser Phe Ser Asp Glu Leu Tyr Val Asp Val Thr Tyr
        115                 120                 125

Ile Val Gln Pro Asp Pro Pro Leu Glu Leu Ala Val Glu Val Lys Gln
    130                 135                 140

Pro Glu Asp Arg Lys Pro Tyr Leu Trp Ile Lys Trp Ser Pro Pro Thr
145                 150                 155                 160

Leu Ile Asp Leu Lys Thr Gly Trp Phe Thr Leu Leu Tyr Glu Ile Arg
                165                 170                 175

Leu Lys Pro Glu Lys Ala Ala Glu Trp Glu Ile His Phe Ala Gly Gln
            180                 185                 190

Gln Thr Glu Phe Lys Ile Leu Ser Leu His Pro Gly Gln Lys Tyr Leu
        195                 200                 205

Val Gln Val Arg Cys Lys Pro Asp His Gly Tyr Trp Ser Ala Trp Ser
    210                 215                 220

Pro Ala Thr Phe Ile Gln Ile Pro Ser Asp Phe Thr Met Asn Asp Glu
225                 230                 235                 240

Pro Arg Gly Pro Thr Ile Lys Pro Cys Pro Pro Cys Lys Cys Pro Ala
                245                 250                 255

Pro Asn Leu Leu Gly Gly Pro Ser Val Phe Ile Phe Pro Pro Lys Ile
            260                 265                 270

Lys Asp Val Leu Met Ile Ser Leu Ser Pro Ile Val Thr Cys Val Val
```

```
                   275                 280                 285
Val Asp Val Ser Glu Asp Asp Pro Asp Val Gln Ile Ser Trp Phe Val
            290                 295                 300

Asn Asn Val Glu Val His Thr Ala Gln Thr Gln Thr His Arg Glu Asp
305                 310                 315                 320

Tyr Asn Ser Thr Leu Arg Val Val Ser Ala Leu Pro Ile Gln His Gln
                325                 330                 335

Asp Trp Met Ser Gly Lys Glu Phe Lys Cys Lys Val Asn Asn Lys Asp
                340                 345                 350

Leu Pro Ala Pro Ile Glu Arg Thr Ile Ser Lys Pro Lys Gly Ser Val
                355                 360                 365

Arg Ala Pro Gln Val Tyr Val Leu Pro Pro Glu Glu Glu Met Thr
                370                 375                 380

Lys Lys Gln Val Thr Leu Thr Cys Met Val Thr Asp Phe Met Pro Glu
385                 390                 395                 400

Asp Ile Tyr Val Glu Trp Thr Asn Asn Gly Lys Thr Glu Leu Asn Tyr
                405                 410                 415

Lys Asn Thr Glu Pro Val Leu Asp Ser Asp Gly Ser Tyr Phe Met Tyr
                420                 425                 430

Ser Lys Leu Arg Val Glu Lys Lys Asn Trp Val Glu Arg Asn Ser Tyr
                435                 440                 445

Ser Cys Ser Val Val His Glu Gly Leu His Asn His Thr Thr Lys
                450                 455                 460

Ser Phe Ser Arg Thr Pro Gly Lys
465                 470

<210> SEQ ID NO 403
<211> LENGTH: 267
<212> TYPE: PRT
<213> ORGANISM: Artificial Sequence
<220> FEATURE:
<223> OTHER INFORMATION: monkey (mf) PRLR ecto-mmH

<400> SEQUENCE: 403

Met His Arg Pro Arg Arg Gly Thr Arg Pro Pro Leu Ala Leu
1               5                   10                  15

Leu Ala Leu Leu Ala Ala Arg Gly Ala Asp Ala Gln Leu Pro
            20                  25                  30

Pro Gly Lys Pro Glu Ile Phe Lys Cys Arg Ser Pro Asn Lys Glu Thr
                35                  40                  45

Phe Thr Cys Trp Trp Arg Pro Gly Thr Asp Gly Gly Leu Pro Thr Asn
50                  55                  60

Tyr Ser Leu Thr Tyr His Arg Glu Gly Glu Thr Leu Met His Glu Cys
65                  70                  75                  80

Pro Asp Tyr Ile Thr Gly Gly Pro Asn Ser Cys His Phe Gly Lys Gln
                85                  90                  95

Tyr Thr Ser Met Trp Arg Thr Tyr Val Met Met Val Asn Ala Thr Asn
                100                 105                 110

Gln Met Gly Ser Ser Phe Ser Asp Glu Leu Tyr Val Asp Val Thr Tyr
                115                 120                 125

Ile Val Gln Pro Asp Pro Leu Glu Leu Thr Val Glu Val Lys Gln
            130                 135                 140

Pro Glu Asp Arg Lys Pro Tyr Leu Trp Met Lys Trp Ser Pro Pro Thr
145                 150                 155                 160

Leu Ile Asp Leu Lys Thr Gly Trp Phe Thr Leu Leu Tyr Glu Ile Arg
```

```
                        165                 170                 175
Leu Lys Pro Glu Lys Ala Ala Glu Trp Glu Thr His Phe Ala Gly Gln
            180                 185                 190
Gln Thr Glu Phe Lys Ile Leu Ser Leu His Pro Gly Gln Lys Tyr Leu
        195                 200                 205
Val Gln Val Arg Cys Lys Pro Asp His Gly Tyr Trp Ser Ala Trp Ser
    210                 215                 220
Pro Ala Thr Phe Ile Gln Ile Pro Ser Asp Phe Ile Met Asn Asp Glu
225                 230                 235                 240
Gln Lys Leu Ile Ser Glu Glu Asp Leu Gly Gly Glu Gln Lys Leu Ile
                245                 250                 255
Ser Glu Glu Asp Leu His His His His His His
                260                 265

<210> SEQ ID NO 404
<211> LENGTH: 622
<212> TYPE: PRT
<213> ORGANISM: Artificial Sequence
<220> FEATURE:
<223> OTHER INFORMATION: full length human PRLR

<400> SEQUENCE: 404

Met Lys Glu Asn Val Ala Ser Ala Thr Val Phe Thr Leu Leu Leu Phe
1               5                   10                  15
Leu Asn Thr Cys Leu Leu Asn Gly Gln Leu Pro Pro Gly Lys Pro Glu
                20                  25                  30
Ile Phe Lys Cys Arg Ser Pro Asn Lys Glu Thr Phe Thr Cys Trp Trp
            35                  40                  45
Arg Pro Gly Thr Asp Gly Gly Leu Pro Thr Asn Tyr Ser Leu Thr Tyr
        50                  55                  60
His Arg Glu Gly Glu Thr Leu Met His Glu Cys Pro Asp Tyr Ile Thr
65                  70                  75                  80
Gly Gly Pro Asn Ser Cys His Phe Gly Lys Gln Tyr Thr Ser Met Trp
                85                  90                  95
Arg Thr Tyr Ile Met Met Val Asn Ala Thr Asn Gln Met Gly Ser Ser
                100                 105                 110
Phe Ser Asp Glu Leu Tyr Val Asp Val Thr Tyr Ile Val Gln Pro Asp
            115                 120                 125
Pro Pro Leu Glu Leu Ala Val Glu Val Lys Gln Pro Glu Asp Arg Lys
        130                 135                 140
Pro Tyr Leu Trp Ile Lys Trp Ser Pro Pro Thr Leu Ile Asp Leu Lys
145                 150                 155                 160
Thr Gly Trp Phe Thr Leu Leu Tyr Glu Ile Arg Leu Lys Pro Glu Lys
                165                 170                 175
Ala Ala Glu Trp Glu Ile His Phe Ala Gly Gln Gln Thr Glu Phe Lys
            180                 185                 190
Ile Leu Ser Leu His Pro Gly Gln Lys Tyr Leu Val Gln Val Arg Cys
        195                 200                 205
Lys Pro Asp His Gly Tyr Trp Ser Ala Trp Ser Pro Ala Thr Phe Ile
    210                 215                 220
Gln Ile Pro Ser Asp Phe Thr Met Asn Asp Thr Thr Val Trp Ile Ser
225                 230                 235                 240
Val Ala Val Leu Ser Ala Val Ile Cys Leu Ile Ile Val Trp Ala Val
                245                 250                 255
Ala Leu Lys Gly Tyr Ser Met Val Thr Cys Ile Phe Pro Pro Val Pro
```

-continued

```
                260                 265                 270
Gly Pro Lys Ile Lys Gly Phe Asp Ala His Leu Leu Glu Lys Gly Lys
                275                 280                 285

Ser Glu Glu Leu Leu Ser Ala Leu Gly Cys Gln Asp Phe Pro Pro Thr
290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
                340                 345                 350

Ser Cys Asp Ser Pro Ser Leu Leu Ser Glu Lys Cys Glu Glu Pro Gln
                355                 360                 365

Ala Asn Pro Ser Thr Phe Tyr Asp Pro Glu Val Ile Glu Lys Pro Glu
                370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
                420                 425                 430

Ile Thr Asp Val Cys Glu Leu Ala Val Gly Pro Ala Gly Ala Pro Ala
                435                 440                 445

Thr Leu Leu Asn Glu Ala Gly Lys Asp Ala Leu Lys Ser Ser Gln Thr
                450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
                500                 505                 510

His Lys Val Asn Lys Asp Gly Ala Leu Ser Leu Leu Pro Lys Gln Arg
                515                 520                 525

Glu Asn Ser Gly Lys Pro Lys Pro Gly Thr Pro Glu Asn Asn Lys
                530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
                580                 585                 590

Ala Asn Phe Thr Ala Thr Ser Ser Lys Cys Arg Leu Gln Leu Gly Gly
                595                 600                 605

Leu Asp Tyr Leu Asp Pro Ala Cys Phe Thr His Ser Phe His
610                 615                 620
```